(12) United States Patent
Poutiatine et al.

(10) Patent No.: US 8,357,114 B2
(45) Date of Patent: Jan. 22, 2013

(54) DRUG DISPENSING DEVICE WITH FLEXIBLE PUSH ROD

(75) Inventors: Andrew I. Poutiatine, San Anselmo, CA (US); Charles Rampersaud, San Francisco, CA (US); Thomas Schreck, Portola Valley, CA (US); William Kolosi, San Francisco, CA (US); Sascha Retailleau, San Francisco, CA (US)

(73) Assignee: AcelRx Pharmaceuticals, Inc., Redwood City, CA (US)

( * ) Notice: Subject to any disclaimer, the term of this patent is extended or adjusted under 35 U.S.C. 154(b) by 29 days.

(21) Appl. No.: 11/650,230

(22) Filed: Jan. 5, 2007

(65) Prior Publication Data

US 2007/0186923 A1    Aug. 16, 2007

Related U.S. Application Data

(60) Provisional application No. 60/756,937, filed on Jan. 6, 2006.

(51) Int. Cl.
*A61M 31/00* (2006.01)
(52) U.S. Cl. ........................................ 604/59
(58) Field of Classification Search ............... 604/59, 604/57; 221/15, 232; 700/231
See application file for complete search history.

(56) References Cited

U.S. PATENT DOCUMENTS

| | | | |
|---|---|---|---|
| 2,621,655 A * | 12/1952 | Olson | 604/62 |
| 3,444,858 A | 5/1969 | Russell | |
| 4,020,558 A | 5/1977 | Cournut et al. | |
| 4,229,447 A | 10/1980 | Porter et al. | |
| 4,237,884 A | 12/1980 | Erickson | |
| 4,474,308 A * | 10/1984 | Bergeron | 221/24 |
| 4,582,835 A | 4/1986 | Lewis et al. | |
| 4,671,953 A | 6/1987 | Stanley et al. | |
| 4,764,378 A | 8/1988 | Keith et al. | |
| 4,785,969 A | 11/1988 | McLaughlin | |
| 4,863,737 A | 9/1989 | Stanley et al. | |
| 4,873,076 A | 10/1989 | Fishman et al. | |
| 4,880,634 A | 11/1989 | Speiser et al. | |
| 4,950,234 A * | 8/1990 | Fujioka et al. | 604/60 |
| 5,080,903 A | 1/1992 | Ayache et al. | |
| 5,112,616 A | 5/1992 | McCarty | |
| 5,122,127 A | 6/1992 | Stanley | |
| 5,132,114 A | 7/1992 | Stanley et al. | |
| 5,178,878 A | 1/1993 | Wehling et al. | |

(Continued)

FOREIGN PATENT DOCUMENTS

| | | |
|---|---|---|
| EP | 2114383 | 7/2010 |
| GB | 2309966 | 8/1997 |

(Continued)

OTHER PUBLICATIONS

Brendenberg, "New Concepts in Administration of Drugs in Tablet Form—Formulations and Evaluation of a Sublingual Tablet for Rapid Absorption, and Presentation of an Individualised Dose Administration System", Comprehensive Summaries of Uppsala Dissertations from the Faculty of Pharmacy 287, ACTA Universitatis UPSALIENSIS UPPSALA.

(Continued)

*Primary Examiner* — Kevin C Sirmons
*Assistant Examiner* — Bradley Osinski

(57) ABSTRACT

Drug storage and dispensing devices for dispensing a drug dosage form are disclosed. Devices having a housing defining a nonlinear passageway and a flexible push rod to move within the nonlinear passageway are disclosed. Devices having a flexible push rod coupled to a rotation actuating member at at an end portion thereof are also disclosed.

33 Claims, 37 Drawing Sheets

U.S. PATENT DOCUMENTS

| | | | |
|---|---|---|---|
| 5,223,264 A | 6/1993 | Wehling et al. | |
| 5,236,714 A | 8/1993 | Lee | |
| 5,288,497 A | 2/1994 | Stanley et al. | |
| 5,288,498 A | 2/1994 | Stanley et al. | |
| 5,292,307 A | 3/1994 | Dolzine et al. | |
| 5,296,234 A | 3/1994 | Hadaway et al. | |
| 5,348,158 A | 9/1994 | Honan et al. | |
| 5,489,025 A | 2/1996 | Romick | |
| 5,489,689 A | 2/1996 | Mathew | |
| 5,507,277 A | 4/1996 | Rubsamen | |
| 5,507,807 A * | 4/1996 | Shippert | 623/8 |
| 5,657,748 A * | 8/1997 | Braithwaite | 128/203.15 |
| 5,660,273 A | 8/1997 | Discko, Jr. | |
| 5,694,919 A | 12/1997 | Rubsamen | |
| 5,710,551 A | 1/1998 | Ridgeway | |
| 5,724,957 A | 3/1998 | Rubsamen | |
| 5,735,263 A | 4/1998 | Rubsamen | |
| 5,752,620 A | 5/1998 | Pearson | |
| 5,785,989 A | 7/1998 | Stanley et al. | |
| 5,800,832 A | 9/1998 | Tapolsky et al. | |
| 5,827,525 A | 10/1998 | Liao et al. | |
| 5,850,937 A | 12/1998 | Rauche et al. | |
| 5,855,908 A | 1/1999 | Stanley et al. | |
| 5,945,651 A | 8/1999 | Chorosinski | |
| 5,950,632 A | 9/1999 | Reber et al. | |
| 5,954,641 A | 9/1999 | Kehr et al. | |
| 5,968,547 A | 10/1999 | Reder | |
| 5,981,552 A | 11/1999 | Alam et al. | |
| 5,995,938 A | 11/1999 | Whaley | |
| 5,997,518 A * | 12/1999 | Laibovitz et al. | 604/296 |
| 6,024,981 A | 2/2000 | Khankari et al. | |
| 6,039,251 A | 3/2000 | Holowko | |
| 6,116,414 A | 9/2000 | Discko, Jr. | |
| 6,171,294 B1 | 1/2001 | Southam et al. | |
| 6,190,326 B1* | 2/2001 | McKinnon et al. | 600/529 |
| 6,200,604 B1 | 3/2001 | Pather et al. | |
| 6,210,699 B1 | 4/2001 | Acharya | |
| 6,216,033 B1 | 4/2001 | Southam et al. | |
| 6,230,927 B1 | 5/2001 | Schoonen et al. | |
| 6,234,343 B1 | 5/2001 | Papp | |
| 6,248,789 B1 | 6/2001 | Weg et al. | |
| 6,264,981 B1 | 7/2001 | Zhang et al. | |
| 6,294,999 B1 | 9/2001 | Yarin et al. | |
| 6,310,072 B1* | 10/2001 | Smith et al. | 514/282 |
| 6,319,510 B1 | 11/2001 | Yates et al. | |
| 6,328,159 B1 | 12/2001 | Discko, Jr. | |
| 6,350,470 B1 | 2/2002 | Pather et al. | |
| 6,358,944 B1 | 3/2002 | Lederman et al. | |
| 6,391,335 B1 | 5/2002 | Pather et al. | |
| 6,417,184 B1 | 7/2002 | Ockert et al. | |
| 6,425,892 B2 | 7/2002 | Southam et al. | |
| 6,484,718 B1 | 11/2002 | Schaffer | |
| 6,488,953 B2 | 12/2002 | Halliday et al. | |
| 6,495,120 B2 | 12/2002 | McCoy et al. | |
| 6,500,456 B1 | 12/2002 | Capella et al. | |
| 6,509,036 B2 | 1/2003 | Pather et al. | |
| 6,541,021 B1 | 4/2003 | Johnson et al. | |
| 6,576,250 B1 | 6/2003 | Pather et al. | |
| 6,605,060 B1 | 8/2003 | O'Neil et al. | |
| 6,641,838 B2 | 11/2003 | Pather et al. | |
| 6,642,258 B1 | 11/2003 | Bourrie et al. | |
| 6,645,528 B1 | 11/2003 | Straub et al. | |
| 6,651,651 B1 | 11/2003 | Bonney et al. | |
| 6,660,295 B2 | 12/2003 | Watanabe et al. | |
| 6,680,071 B1 | 1/2004 | Johnson | |
| 6,682,716 B2 | 1/2004 | Hodges et al. | |
| 6,685,951 B2 | 2/2004 | Cutler et al. | |
| 6,689,373 B2 | 2/2004 | Johnson et al. | |
| 6,726,053 B1 | 4/2004 | Harrold | |
| 6,752,145 B1 | 6/2004 | Bonney et al. | |
| 6,759,059 B1 | 7/2004 | Pettersson et al. | |
| 6,761,910 B1 | 7/2004 | Pettersson et al. | |
| 6,762,684 B1 | 7/2004 | Camhi | |
| 6,764,696 B2 | 7/2004 | Pather et al. | |
| 6,776,978 B2 | 8/2004 | Rabinowitz et al. | |
| 6,793,075 B1 | 9/2004 | Jeter et al. | |
| 6,796,429 B2 | 9/2004 | Cameron | |
| 6,824,512 B2 | 11/2004 | Warkentin et al. | |
| 6,835,194 B2 | 12/2004 | Johnson et al. | |
| 6,855,310 B2 | 2/2005 | Rabinowitz et al. | |
| 6,881,208 B1 | 4/2005 | Phipps et al. | |
| 6,914,668 B2 | 7/2005 | Brestel | |
| 6,932,983 B1 | 8/2005 | Straub et al. | |
| 6,959,808 B2 | 11/2005 | Discko | |
| 6,961,541 B2 | 11/2005 | Overy et al. | |
| 6,963,289 B2 | 11/2005 | Aljadeff et al. | |
| 6,969,508 B2 | 11/2005 | Dugger, III et al. | |
| 6,974,590 B2 | 12/2005 | Pather et al. | |
| 6,999,028 B2 | 2/2006 | Egbert et al. | |
| 7,018,370 B2 | 3/2006 | Southam et al. | |
| 7,018,619 B2 | 3/2006 | Rabinowitz et al. | |
| 7,044,125 B2 | 5/2006 | Vedrine | |
| 7,044,302 B2 | 5/2006 | Conley et al. | |
| 7,070,762 B2 | 7/2006 | Rabinowitz et al. | |
| 7,070,764 B2 | 7/2006 | Rabinowitz et al. | |
| 7,070,765 B2 | 7/2006 | Rabinowitz et al. | |
| 7,072,738 B2 | 7/2006 | Bonney et al. | |
| 7,074,935 B2 | 7/2006 | Mathew et al. | |
| 7,078,018 B2 | 7/2006 | Rabinowitz et al. | |
| 7,078,019 B2 | 7/2006 | Rabinowitz et al. | |
| 7,090,830 B2 | 8/2006 | Hale et al. | |
| 7,090,866 B2 | 8/2006 | Johnson | |
| 7,119,690 B2 | 10/2006 | Lerch et al. | |
| 7,168,626 B2 | 1/2007 | Lerch et al. | |
| 7,169,378 B2 | 1/2007 | Rabinowitz et al. | |
| 7,198,172 B2 | 4/2007 | Harvey et al. | |
| 7,208,604 B2 | 4/2007 | Mathew et al. | |
| 7,215,295 B2 | 5/2007 | Egbert et al. | |
| 7,248,165 B2 | 7/2007 | Collins et al. | |
| 7,276,246 B2 | 10/2007 | Zhang et al. | |
| 7,295,890 B2 | 11/2007 | Jean-Pierre | |
| 7,306,812 B2 | 12/2007 | Zhang et al. | |
| 7,458,374 B2 | 12/2008 | Hale et al. | |
| 7,468,179 B2 | 12/2008 | Rabinowitz et al. | |
| 7,484,642 B2 | 2/2009 | Bonney et al. | |
| 7,500,444 B2 | 3/2009 | Bonney et al. | |
| 7,552,728 B2 | 6/2009 | Bonney et al. | |
| 2001/0020147 A1 | 9/2001 | Staniforth et al. | |
| 2002/0026330 A1 | 2/2002 | Klein et al. | |
| 2002/0071857 A1 | 6/2002 | Kararli et al. | |
| 2002/0110578 A1 | 8/2002 | Pather et al. | |
| 2002/0142050 A1 | 10/2002 | Straub et al. | |
| 2002/0160043 A1 | 10/2002 | Coleman | |
| 2003/0008005 A1 | 1/2003 | Cutler et al. | |
| 2003/0015196 A1 | 1/2003 | Hodges et al. | |
| 2003/0015197 A1 | 1/2003 | Hale et al. | |
| 2003/0017175 A1 | 1/2003 | Cutler et al. | |
| 2003/0022910 A1 | 1/2003 | Cutler et al. | |
| 2003/0035776 A1 | 2/2003 | Hodges et al. | |
| 2003/0052135 A1 | 3/2003 | Conley et al. | |
| 2003/0052787 A1 | 3/2003 | Zerhusen et al. | |
| 2003/0077300 A1 | 4/2003 | Wermeling et al. | |
| 2003/0088236 A1 | 5/2003 | Johnson et al. | |
| 2003/0091629 A1 | 5/2003 | Pather et al. | |
| 2003/0099158 A1 | 5/2003 | De La Huerga | |
| 2003/0130314 A1 | 7/2003 | Druzgala et al. | |
| 2003/0132239 A1 | 7/2003 | Konig et al. | |
| 2003/0171401 A1 | 9/2003 | Johnson et al. | |
| 2003/0173408 A1 | 9/2003 | Mosher et al. | |
| 2003/0185872 A1* | 10/2003 | Kochinke | 424/426 |
| 2003/0190290 A1 | 10/2003 | Ross et al. | |
| 2003/0232080 A1 | 12/2003 | Pather et al. | |
| 2004/0017567 A1 | 1/2004 | Loicht et al. | |
| 2004/0025871 A1 | 2/2004 | Davies et al. | |
| 2004/0034059 A1 | 2/2004 | Grarup et al. | |
| 2004/0037882 A1 | 2/2004 | Johnson et al. | |
| 2004/0080515 A1 | 4/2004 | Hagiwara et al. | |
| 2004/0092531 A1 | 5/2004 | Ghizh et al. | |
| 2004/0094564 A1* | 5/2004 | Papp | 221/25 |
| 2004/0096402 A1 | 5/2004 | Hodges et al. | |
| 2004/0120896 A1 | 6/2004 | Dugger et al. | |
| 2004/0133305 A1 | 7/2004 | Jean Pierre | |
| 2004/0157884 A1 | 8/2004 | Johnson et al. | |
| 2004/0158349 A1* | 8/2004 | Bonney et al. | 700/231 |
| 2004/0170567 A1 | 9/2004 | Sackler | |
| 2004/0180080 A1 | 9/2004 | Furusawa et al. | |
| 2004/0185003 A1 | 9/2004 | Rabinowitz et al. | |

| | | | |
|---|---|---|---|
| 2004/0191178 A1 | 9/2004 | Cutler et al. | |
| 2004/0202617 A1 | 10/2004 | Rabinowitz et al. | |
| 2004/0213855 A1 | 10/2004 | Pettersson et al. | |
| 2004/0248964 A1 | 12/2004 | Crooks et al. | |
| 2004/0253307 A1* | 12/2004 | Hague et al. | 424/464 |
| 2005/0038062 A1 | 2/2005 | Burns et al. | |
| 2005/0049464 A1 | 3/2005 | Lassers et al. | |
| 2005/0054942 A1 | 3/2005 | Melker et al. | |
| 2005/0064030 A1 | 3/2005 | Pather et al. | |
| 2005/0065175 A1 | 3/2005 | Gonzales et al. | |
| 2005/0075273 A1 | 4/2005 | Rabinowitz et al. | |
| 2005/0089479 A1 | 4/2005 | Rabinowitz et al. | |
| 2005/0101936 A1 | 5/2005 | Gonzales et al. | |
| 2005/0122219 A1 | 6/2005 | Petersen et al. | |
| 2005/0129737 A1 | 6/2005 | Johnson et al. | |
| 2005/0131337 A1 | 6/2005 | Phipps et al. | |
| 2005/0142197 A1 | 6/2005 | Moe et al. | |
| 2005/0142198 A1 | 6/2005 | Moe et al. | |
| 2005/0150488 A1* | 7/2005 | Dave | 128/200.14 |
| 2005/0163838 A1 | 7/2005 | Moe et al. | |
| 2005/0169989 A1 | 8/2005 | Agarwal et al. | |
| 2005/0171464 A1 | 8/2005 | Phipps et al. | |
| 2005/0176790 A1 | 8/2005 | Bartholomaus | |
| 2005/0258066 A1 | 11/2005 | Conley et al. | |
| 2006/0026035 A1 | 2/2006 | Younkes | |
| 2006/0031099 A1 | 2/2006 | Vitello et al. | |
| 2006/0039959 A1 | 2/2006 | Wessling et al. | |
| 2006/0045865 A1 | 3/2006 | Jacob et al. | |
| 2006/0062812 A1 | 3/2006 | Ross et al. | |
| 2006/0067978 A1 | 3/2006 | Heiler | |
| 2006/0069344 A1 | 3/2006 | Southam et al. | |
| 2006/0089858 A1 | 4/2006 | Ling | |
| 2006/0134200 A1 | 6/2006 | Vandoni et al. | |
| 2006/0216352 A1 | 9/2006 | Nystrom et al. | |
| 2006/0229570 A1 | 10/2006 | Lovell | |
| 2006/0233718 A1 | 10/2006 | Rabinowitz et al. | |
| 2006/0251587 A1 | 11/2006 | Rabinowitz et al. | |
| 2006/0292219 A1 | 12/2006 | Pather et al. | |
| 2007/0020186 A1 | 1/2007 | Stroppolo et al. | |
| 2007/0031502 A1 | 2/2007 | Pettersson et al. | |
| 2007/0036853 A1 | 2/2007 | Agarwal et al. | |
| 2007/0071806 A1 | 3/2007 | McCarty et al. | |
| 2007/0074722 A1 | 4/2007 | Giroux | |
| 2007/0104763 A1 | 5/2007 | Jobdevairakkam et al. | |
| 2007/0178052 A1 | 8/2007 | Rabinowitz et al. | |
| 2007/0185084 A1 | 8/2007 | McKinney et al. | |
| 2007/0190130 A1 | 8/2007 | Mark et al. | |
| 2007/0207207 A1 | 9/2007 | Tzannis et al. | |
| 2007/0260491 A1 | 11/2007 | Palmer et al. | |
| 2007/0286900 A1 | 12/2007 | Herry | |
| 2007/0299687 A1 | 12/2007 | Palmer et al. | |
| 2008/0147044 A1 | 6/2008 | Palmer et al. | |
| 2008/0164275 A1 | 7/2008 | Poutiatine et al. | |
| 2008/0166404 A1 | 7/2008 | Tzannis et al. | |
| 2008/0203107 A1 | 8/2008 | Conley et al. | |
| 2008/0268023 A1 | 10/2008 | Palmer et al. | |
| 2009/0010992 A1 | 1/2009 | Palmer et al. | |
| 2009/0048237 A1 | 2/2009 | Palmer et al. | |
| 2009/0131479 A1 | 5/2009 | Palmer et al. | |
| 2010/0105735 A1 | 4/2010 | Palmer et al. | |
| 2010/0130551 A1 | 5/2010 | Pushpala et al. | |
| 2010/0137836 A1 | 6/2010 | Palmer et al. | |
| 2010/0253476 A1 | 10/2010 | Poutiatine et al. | |
| 2010/0256190 A1 | 10/2010 | Palmer et al. | |
| 2011/0091544 A1 | 4/2011 | Palmer | |
| 2011/0288128 A1 | 11/2011 | Palmer et al. | |
| 2012/0035216 A1 | 2/2012 | Palmer et al. | |
| 2012/0232473 A1 | 9/2012 | Poutiatine et al. | |

FOREIGN PATENT DOCUMENTS

| | | |
|---|---|---|
| JP | 2000-142841 | 5/2000 |
| JP | 2003-525081 A | 8/2003 |
| JP | 2007-517636 A | 7/2007 |
| WO | 00/16750 | 3/2000 |
| WO | 00/57858 | 10/2000 |
| WO | 01/30288 | 5/2001 |
| WO | WO 01/64182 | 7/2001 |
| WO | 01/97780 | 12/2001 |
| WO | WO 02/32487 | 4/2002 |
| WO | WO 02/074372 | 9/2002 |
| WO | WO 02/078594 | 10/2002 |
| WO | WO 03/092575 | 11/2003 |
| WO | 2004/069198 | 8/2004 |
| WO | WO2004080515 | 9/2004 |
| WO | 2006/097361 | 9/2006 |

OTHER PUBLICATIONS

Chauvin, M., "Sufentanil Pharmacokinetics in Patients With Cirrhosis", Anesthes Analg, 1989, 68(1):1-4.
Farnsworth, S.T., et al., "Ocular Transmucosal Absorption and Toxicity of Sufentanil in Dogs", Anesth Analg, 1998, 86:138-140.
Gardner-Nix J., "Oral Transmucosal Fentanyl and Sufentanil for Incident Pain", J Pain Symptom Management, Aug. 2001, 22(2):627-630.
Gordon, D.B., Oral Transmucosal Fentanyl Citrate for Cancer Breakthrough Pain: A Review, Oncol Nurs Forum, Nov. 3, 2006, 33(2)257-264.
Haynes, G., "Plasma Sufentantil Concentration After Intranasal Administration to Paediatric Outpatients", Can J. Anaesth, 1993, 40(3):286.
Helmers, et al., 1989, Can J. Anaesth, 1989, 6:494-497.
Jackson K., et al., "Pilot Dose Finding Study of Intranasal Sufentanil for Breakthrough and Incident Cancer-Associated Pain", J Pain Symptom Manage, 2002, 23(6):450-452.
Kunz, K.M., "Severe Episodic Pain: Management With Sublingual Sufentanil", Journal of Pain and Symptom Management, 1993, 8:189-190.
Mathieu, N., et al., "Intranasal Sufentanil is Effective for Postoperative analgesia in Adults", Can J Anesth, 2006, 53(1):60-66.
Monk, J.P., "Sufentanil: A Review of Its Pharmacological Properties and Therapeutic Use", Drugs, 1988, 36:286-313.
Roy, S.D., "Transdermal Delivery of Narcotic Analgesics: pH, Anatomical, and Subject Influences on Cutaneous Permeability of Fentanyl and Sufentanil", Pharm Res, 1990, 7:842-847.
Sinatra, R.S., "Patient-Controlled Analgesia with Sufentanil: A Comparison of Two Different Methods of Administration", Journal of Clinical Anesthesia, 1996, 8:123-129.
Vercauteren M., "Intranasal Sufentanil for Pre-Operative Sedation", Anaesthesia, 1988, 43(4):270-273.
Weniberg, D.S., Sublingual Absorption of Selected Opioid Analgesics, Clin Parmacol Ther, Sep. 1988, 44(3):335-342.
Willens, J.S., "Pharmacodynamics, Pharmacokinetics, and Clinical Uses of Fentanyl; Sufentanil, and Alfentanil", Heart and Lung, 1993, 22:239-251.
Zhang, H., "Oral Mucosal Drug Delivery: Clinical Pharmacokinetics and Therapeutic Applications", Clinical Pharmacokinetics, 2002, 41(9):661-680(20).
International Search Report and Written Opinion dated Dec. 17, 2007 issued in PCT/2007/00527 (WO/2007/081947).
International Search Report and Written Opinion dated Feb. 4, 2008 issued in PCT/2007/00528 (WO/2007/081948).
Bredenberg et al; "In vitro and in vivo evaluation of a new sublingual tablet system for rapid or mucosal absorption using fentanyl citrate as the active substance"; *European Journal of Pharmaceutical Sciences*; 2003; 327-334.
KGH Drug Information Service; "Sublingual Sufentanil for Incident Pain"; *KGH Drug Information Bulletin*, vol. 37(4) 2, 2004.
Yeomans et al.; "Sublingual Sufentanil"; *Vancouver Hospital and Health Science Center Drug and Therapeutics Newsletter*, vol. 8(1) 2, 2001.
Berthold, et al., (2007) Oral Surg Oral med Oral Pathol Oral Radiol Endo, 84(2):119-24.
Coluzzi, et al., (2001) Pain, 91:123-30.
Dale, et al., 2002, Acta Anaesth Scand, 46:759-770.
Darwish, et al., 2008, Clin Drug Invest, 28(1):1-7.
Darwish, et al., 2007, Expert Opin Pharmacother, 8(13):2011-6.
Darwish, et al., 2006, Clinical Pharmacokinetics, 45(8):843-50.
Darwish, et al., 2006, Clinical Therapies, 28(5):707-14.
Darwish, et al., 2006, Clinical Therapies, 28(5):715-24.
Darwish, et al., 2005, Clinical Pharmacokinetics, 44(12): 1279-86.
Durfee, et al., 2006, American Journal Drug Delivery, 4(1):1-5(5).
Egan, et al., 2000, Anesthesiology, 92:665-73.

Geldner, et al., 1997, Paediatric Anaesthesia, 7:103-109.
Gerak, et al., 1998, Psychopharmacology, 137(2):164-74.
Gram-Hansen, et al., 1988, Int J Clin Pharmacol Ther Toxicol, 26(6):323-4.
Jackson, et al., 2006, Journal Clinical Psychopharmacology, 26(1):4-8.
James, et al., 2005, Clinical Radiology, 60:394-396.
Jeannet, et al., 1999, Eur J Paediatric Neurology, 3:73-77.
Kaplan, et al., 1998, J Clin Pharmacol, 38(1): 14-21.
Karl, et al., 1997, Journal of Clinical Psychopharmacology, 17(3):169-172.
Karl, et al., 1992, Anesthesiology, 76:209-215.
Karl, et al., 1993, Anesthesiology, 78(5):885-91.
Khalil, et al., 1998, Paediatric Anaesthesia, (8):461-465.
Kogan, et al., 2002, Paediatric Anaesthesia, 12:685-689.
Kontinen, et al, 1993, Canadian Journal of Anesthesia, vol. 40, 829-834.
Kroboth, et al, 1995, J Clin Psychopharmacol, 15(4):259-62.
Kunz, et al.,1993, J Pain Symp Manag, 8(4):189-190.
Lennernas, et al., 2004, Br J Clin Pharmacol, 59(2):249-253.
Lichtor, et al., 1999, Anesth Anal, 89(3):732-8.
Lim, et al., 1997, Can J Anaesth, 44(7):723-6.
Lipworth, et al., 1989, Eur J Clin Pharmacol, 37:567-571.
McCann, et al., 2001, Anesthesia & Analgesia, 93:98-105.
Naguib, et al., 2000, Anesth Analg, 91:473-9.
Odou, et al., 1999, Eur J Drug Metab Pharmacokinet, 24(1):1-7.
Odou, et al., 1998, Eur J Drug Metab Pharmacokinet, 23(2):87-91.
Okayama, et al., 1984, Eur J Clin Pharamcol, 26:151-155.
Reynolds, et al., 2004, Pain, 110:182-188.
Scavone, et al., 1987, J Clin Psychpharmacol, 7(5):332-4.
Scavone, et al., 1992, Eur J Clin Pharmacol, 42(4):439-43.
Scavone, et al., 1986, J Clin Pharmacol, 26:208-10.
Schreiber, et al., 2006, The American Journal of Emergency Medicine, 24:397-401.
Schwagmeier, et al., 1998, Br J Clin Pharmacol, 46:203-69.
Stopperich, et al., 1993, Anesth Prog, 40(4):117-21.
Tweedy, et al., 2001, J Clin Psychopharmacol, 21(3):268-72.
Viitanen, et al., 1999, Can J Anesth, 46(8):766-771.
Wheeler, et al., 2002, Paediatric Anesthesia, 12:594-599.
Yager, et al., 1988, Am J Dis Child, 142:931-2.
Zedie, et al., 1996, Clin Pharmacol Ther, 59:341-8.
Fentora Package Insert, 100-800mcg dose of fentanyl; buccal absorption with approximately 50% absorbed transmucosally remainder swallowed/absorbed via GI tract. (p. 4 of package insert).
ISR from WO 08/085764, Date mailed Jun. 23, 2008.
Sufenta Package Insert, 2006.
Darwish et al., 2007, J Clin Pharm 47: 56-63.
ACTIQ fact sheet printed Mar. 2004.
Office Action for U.S. Appl. No. 11/980,216, mailed Dec. 24, 2008.
Office Action for U.S. Appl. No. 11/650,227, mailed Dec. 9, 2008.
Office Action for U.S. Appl. No. 11/473,551, mailed Mar. 16, 2009.
Office Action for U.S. Appl. No. 11/429,904, mailed Mar. 5, 2009.
Henderson JM, et al.; Anesthesiology; 1988; 68:671-675.
Mendelson J, et al.; J Clin Pharmacol; 1997; 37:31-7.
Motwani JG, Lipworth BJ; Clin Pharmacokinet; 1991; 21(2):83-94.
Mystakidou K, et al.; Drug Deliv. 2006; 13(4):269-76.
Nath RP, et al.; J Clin Pharmacol; 1999; 39:619-23.
Portenoy RK, et al.; Pain; 1999; 79:303-12.
Reisfield G, Wilson G; Journal of Palliative Medicine; 2007; 10(2):465-475.
Roy, SD and Flynn, GL; Pharm Research; 1989; 6(2): 147-151.
Scholz J, et al.; Clin Pharmacokin ; 1996; 31:275-292.
Streisand JB, et al.; Anesthesiology; 1991; 75:223-9.
Streisand JB, et al.; Anesthesiology; 1998; 88:305-9.
Raza, et al., Can J Anaesth. Nov. 1989; 36(6):617-23.
Walder, et al., Swiss Med Wkly. Jun. 12, 2004; 134(23-24):333-46.
Pavlin, et al., Anesthesiology. Jan. 1996; 84(1):23-37.
Demeules, et al., Eur J Anaesthesiol Suppl. 2003; 28:7-11.
Bethune-Volters A, (2006) Anti-cancer drugs, vol. 17, No. 2, pp. 217-224.
Restriction Requirement for U.S. Appl. No. 11/825,212, mailed Dec. 9, 2009.
Office Action for U.S. Appl. No. 11/825,251, mailed Dec. 15, 2009.
Office Action for U.S. Appl. No. 11/650,227, mailed Dec. 15, 2009.
Office Action for U.S. Appl. No. 11/650,227, mailed Jul. 6, 2009.
Office Action for U.S. Appl. No. 11/825,251, mailed Sep. 21, 2009.
Office Action for U.S. Appl. No. 11/980,216, mailed Jul. 20, 2009.
Office Action for U.S. Appl. No. 11/974,092, mailed Sep. 30, 2009.
Office Action for U.S. Appl. No. 11/473,551, mailed Sep. 11, 2009.
Office Action for U.S. Appl. No. 11/429,904, mailed Aug. 20, 2009.
Office Action for U.S. Appl. No. 11/473,551, mailed Sep. 26, 2008.
Office Action for U.S. Appl. No. 11/429,904, mailed Sep. 17, 2008.
ISR WO 2007/133478; date mailed Aug. 5, 2008.
ISR WO 2008/002358; date mailed Aug. 21, 2008.
Abrams R, et al., Anesth Prog. 1993;40(3):63-6.
AHFS Drug Information, 28:08.08, 2157-2160, 2007.
Anlar S et al., Pharm Res, 11(2):231-6, 1994.
Bayrak F., et al., J Opiod Management, 3(2):74-78, 2007.
Bovill GJ, et al., Anesthesia, 61:502-506, 1984.
Brusset A, et al. Clin Drug Invest, 18(5):377-89, 1999.
De Castro J, et al., Acta Anesth Belgica, 107-128, 1976.
de Vries M et al., Critical Reviews in Therapeutic Drug Carrier Systems, 8(3):271-303, 1991.
Ellmauer S, Anesth, 43(3):143-158, 1994.
Enting H. R, et al., J. Pain and Symptom Management, 29(2):213-217, 2005.
Guay J, Can J Anaesth, 39(1): 14-20, 1992.
Halliburton JR, Anesthesiology, 61(5):502-506, 1984.
Hazardous Substances Data Bank (HSDB); (http://toxnet.nlm.nih.gov) Apr. 9, 2007; Name: Sufentanil; RN: 56030-54-7.
Helmers JH, et al., Eur J Anesth, 11(3):181-5, 1994.
Heshmati et al., Iran. J. Pharmacol. Therap., 5:131-133, 2006.
Ikinci G, et al., Int. J. Pharm, 277(1-2):173-8, 2004.
Kress, Clin. Therap., 31(6) 1177-1191, 2009.
Lehman K. A., et al., Acta Anaesthesiol Scand., 35:221-226, 1991.
Lehman K. A., et al., Acta Anaesthesiol Scand., 37:176-80, 1993.
Mather, Clin. Pharmacokinetics, 8: 422-446, 1983.
Molander L and Lunell E, Eur J Clin Pharmacol, 56(11):813-819, 2001.
Onsolis Package Insert Jul. 2009.
Portenoy RK, et al., Pain, 22(9):805-811, 2006.
Puig MM, et al., Int'l J Clin Pharmaco Ther and Toxicol, 27(5):229-34, 1989.
Roscow, CE, Pharmacotherapy, 4:11-19, 1984.
Savoia G, et al., Minerva Anesth, 67(9 Suppl 1):206-16, 2001.
Siepmann et al., Int J Pharm., 25; 201(2):151-64, 2000.
Smith R.B, et al., J Clin Pharmacol., 26(2):120-4, 1986.
Van de Walle J, et al., Acta Anaesth Belg, 27(3):129-38, 2009.
Office Action for U.S. Appl. No. 11/650,174, mailed Oct. 13, 2010.
Office Action for U.S. Appl. No. 11/650,227, mailed Aug. 5, 2010.
Office Action for U.S. Appl. No. 11/825,251, mailed Aug. 5, 2010.
Office Action for U.S. Appl. No. 11/825,212, mailed Mar. 24, 2010.
Office Action for U.S. Appl. No. 11/825,212, mailed Aug. 31, 2010.
Office Action for U.S. Appl. No. 11/980,216, mailed Jan. 5, 2010.
Office Action for U.S. Appl. No. 11/980,216, mailed Jul. 12, 2010.
Office Action for U.S. Appl. No. 11/974,092, mailed Mar. 31, 2010.
Office Action for U.S. Appl. No. 12/187,937, mailed Sep. 16, 2010.
ISR WO2010/059504 mailed Mar. 17, 2010.
ISR WO2010/107761 mailed Jun. 21, 2010.
Chelly, J. E. et al., "The safety and efficacy of a fentanyl patient-controlled transdermal system for acute postoperative analgesia: a multicenter, placebo-controlled trial," Anesth. Analg., 98:427-433 (2004).
Culling et al., "Haemodynamics and plasma concentrations following sublingual GTN and intravenous, or inhaled isosorbide dinitrate," Br. J. Clin. Pharm., 17:125-131 (1984).
Drug Information Bulletin [online], 37(4) (Sep./Oct. 2004), [Retrieved on Jun. 5, 2008.] Retrieved from the Internet: <URL: http://www.kgh.on.ca/pharmacy/diBulletinSeptOct2004.pdf>, 4 pages.
FDA Guidance for Industry: Container Closure Systems for Packaging Human Drugs and Biologics, pp. 1-E2 (1999).
Fentora®, 2008 Red Book, p. 174.
Griffin, D. et al., Reg. Anesth. Pain Med., vol. 10, American Society of Regional Anesthesia Spring Meeting (2010).

Infusion Pump Improvement Initiative, Center for Devices and Radiological Health, U.S. Food and Drug Administration, Apr. 2010, 7 pages.
Keohane, C. A. et al., "Intravenous medication safety and smart infusion systems," Journal of Infusion Nursing, 28(5):321-328 (Sep./Oct. 2005).
Kotey, G. A. et al., "Iontophoretic delivery of fentanyl for acute post-operative pain management," The European Journal of Hospital Pharmacy Science, 13(1):3-9 (2007).
Lin, L. et al., "Applying human factors to the design of medical equipment: patient-controlled analgesia," J. Clin, Monitoring and Computing, 14:253-263 (1998).
McInnes, F. et al., "Evaluation of the clearance of a sublingual buprenorphine spray in the beagle dog using gamma scintigraphy," Pharmaceutical Research, (2007), 6 pages.
Miaskowski, C., "Patient-controlled modalities for acute postoperative pain management," Journal of PeriAnesthesia Nursing, 20(4):255-267 (Aug. 2005).
Miller, R. D., "The pursuit of excellence. The 47th Annual Rovenstine Lecture," Anesthesiology, 110(4):714-720 (Apr. 2009).
Momeni, M. et al., "Patient-controlled analgesia in the management of postoperative pain," Drugs, 66(18):2321-2337 (2006).
Paradis et al., "Solid-phase microextraction of human plasma samples for determination of sufentanil by gas chromatography-mass spectrometry," Therapeutic Drug Monitoring, 24:768-774 (2002).
Rawal, N. et al., "Current practices for postoperative pain management in Europe and the potential role of the fentanyl HCl iontophoretic transdermal system," European Journal of Anaesthesiology, 24:299-308 (2007).
Rosati, J. et al., "Evaluation of an oral patient-controlled analgesia device for pain management in oncology inpatients," J. Support. Oncol., 5(9):443-448 (2007).
Rothschild, J. M. et al., "A controlled trial of smart infusion pumps to improve medication safety in critically ill patients," Crit. Care Med., 33(3):533-540 (2005).
Sanford et al., "A comparison of morphine, fentanyl, and sufentanil anesthesia for cardiac surgery: induction, emergence, and extubation," Anesthesia and Analgesia, 65:259-266 (1986).
Shojaei, A. H. et al., "Buccal mucosa as a route for systemic drug delivery: a review," Journal of Pharmacy and Pharmaceutical Sciences, 1:15-30 (1998).
Slatkin et al., "Fentanyl Buccal Tablet for Relief of Breakthrough Pain in Opioid-Tolerant Patients With Cancer-Related Chronic Pain," J. of Supportive Oncol., vol. 5, No. 7, Jul./Aug. 2007, pp. 327-334.
Vadivelu, N. et al., "Recent advances in postoperative pain management," Yale Journal of Biology and Medicine, 83:11-25 (2010).
Van Raders, P. et al., "Nurses' views on ease of patient care in postoperative pain management," British Journal of Nursing, 16(5):312-317 (2007).
Vasight, N. et al., "Formulation selection and pharmacokinetic comparison of fentanyl buccal soluble film with oral transmucosal fentanyl citrate," Clin. Drug Investig., 29(10):647-654 (2009).
Vercauteren, M. P. et al., "Epidural sufentanil for postoperative patient-controlled analgesia (PCA) with or without background infusion: a double-blind comparison," Anesth. Analg., 80:76-80 (1995).
Viscusi, E. R., "Patient-controlled drug delivery for acute postoperative pain management: a review of current and emerging technologies," Regional Anesthesia and Pain Medicine, 33(2):146-158 (2008).
Office Action for Japanese Patent Application No. 2009-544898, mailed Jul. 24, 2012.
Office Action for Japanese Application No. 2009-544899, mailed Aug. 1, 2012.
Written Opinion for International Application No. PCT/US2007/010822, mailed Aug. 5, 2008.
Written Opinion for International Application No. PCT/US2007/011337, mailed Aug. 21, 2008.
AcelRx Pharmaceuticals, Inc., "AcelRx Pharmaceuticals Reports Positive Results from a Clinical Trial of Sublingual Sufentanil/Triazolam NanoTabTM Combination (ARX-03) in Treating Procedural Pain and Anxiety," Jan. 12, 2009, pp. 1-2.
Ahmad, S. et al., "Fentanyl HCl iontophoretic transdermal system versus intravenous morphine pump after gynecologic surgery," Arch Gynecol Obstet 276:251-258 (2007).
Albert, J. M. et al., "Patient-Controlled Analgesia vs. Conventional Intramuscular Analgesia Following Colon Surgery," Diseases of the Colon & Rectum, 31(2):83-86 (1988).
Christie, J. M. et al., "Dose-titration, multi-center study of oral transmucosal fentanyl citrate for the treatment of breakthrough pain in cancer patients using transdermal fentanyl for persistent pain," J Clin Oncol., 16(10):3238-45 (1998).
Coda, B.A. et al., "Comparative efficacy of patient-controlled administration of morphine, hydromorphone, or sufentanil for the treatment of oral mucositis pain following bone marrow transplantation," Pain, 72:333-346 (1997).
Collins, L. M. C. et al., "The Surface Area of the Adult Human Mouth and Thickness of the Salivary Film Covering the Teeth and Oral Mucosa," J Dent Res, 66(8):1300-2 (1987).
Darwish, M. et al., "Absolute and Relative Bioavailability of Fentanyl Buccal Tablet and Oral Transmucosal Fentanyl Citrate," Journal of Clinical Pharmacology, 47:343-350 (2007).
Fisher, D.M. et al., "Pharmacokinetics of an Implanted Osmotic Pump Delivering Sufentanil for the Treatment of Chronic Pain," Anesthesiology, 99(4):929-37 (Oct. 2003).
Grass, J., "Patient-Controlled Analgesia," Anesth. Analg., 101:S44-S61 (2005).
Halliburton, J. R., "The Pharmacokinetics of Fentanyl, Sufentanil and Alfentanil: A Comparative Review," Journal of the American Association of Nurse Anesthetists, 56(3):229-233 (1988).
Hicks, R. et al., "USP Medication Safety Forum: Medication Errors Involving Patient-Controlled Analgesia," Joint Commission on Quality and Patient Safety, 34(12):734-742 (2008).
Striebel, H. W. et al., "Patient-controlled intranasal analgesia (PCINA) for the management of postoperative pain: a pilot study," J Clin Anesth, 8:4-8 (1996).
Striebel, H. W. et al., "Patient-controlled intranasal analgesia: a method for noninvasive postoperative pain management," Anesth Analg, 83:548-51 (1996).
Viscusi, E. R. et al., "An iontophoretic fentanyl patient-activated analgesic delivery system for postoperative pain: a double-blind, placebo-controlled trial," Anesth Analg., 102(1):188-194 (2006).
Viscusi, E. R. et al., "Patient-Controlled Transdermal Fentanyl Hydrochloride vs Intravenous Morphine Pump for Postoperative Pain: A randomized controlled trial," JAMA, 291(11):1333-1341 (2004).
International Preliminary Report on Patentability for International Application No. PCT/US2007/089017, dated Jul. 7, 2009.
International Search Report and Written Opinion for International Application No. PCT/US2011/037401, mailed Aug. 19, 2011.
Office Action for U.S. Appl. No. 11/985,162, mailed Dec. 20, 2010.
International Search Report and Written Opinion for International Application No. PCT/US2007/089018, mailed Oct. 15, 2008.
Office Action for U.S. Appl. No. 12/521,983, mailed Feb. 15, 2012.
Office Action for U.S. Appl. No. 12/580,930, mailed Oct. 21, 2011.
Office Action for U.S. Appl. No. 12/275,485, mailed Mar. 2, 2011.
Office Action for U.S. Appl. No. 12/275,485, mailed Nov. 23, 2011.
International Search Report and Written Opinion for International Application No. PCT/US2008/072445, mailed Oct. 20, 2008.
Office Action for U.S. Appl. No. 11/650,174, mailed Jun. 14, 2011.
Written Opinion for International Application No. PCT/US2007/000529, mailed Sep. 11, 2007.
International Preliminary Report on Patentability for International Application No. PCT/US2007/000529, dated Jul. 8, 2008.
Supplementary European Search Report for European Application No. EP07716450, mailed Apr. 6, 2011.
International Preliminary Report on Patentability for International Application No. PCT/US2007/000527, dated Feb. 24, 2009.
International Search Report and Written Opinion for International Application No. PCT/US2007/089016, mailed Jun. 17, 2008.
International Preliminary Report on Patentability for International Application No. PCT/US2007/089016, dated Jul. 7, 2009.

* cited by examiner

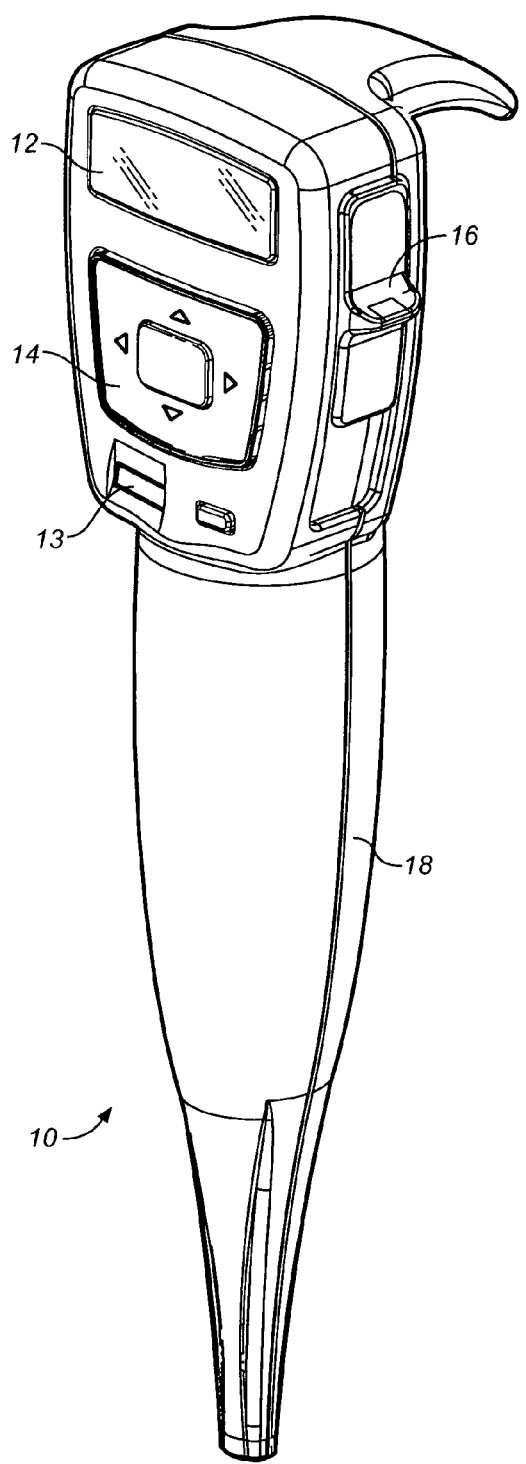
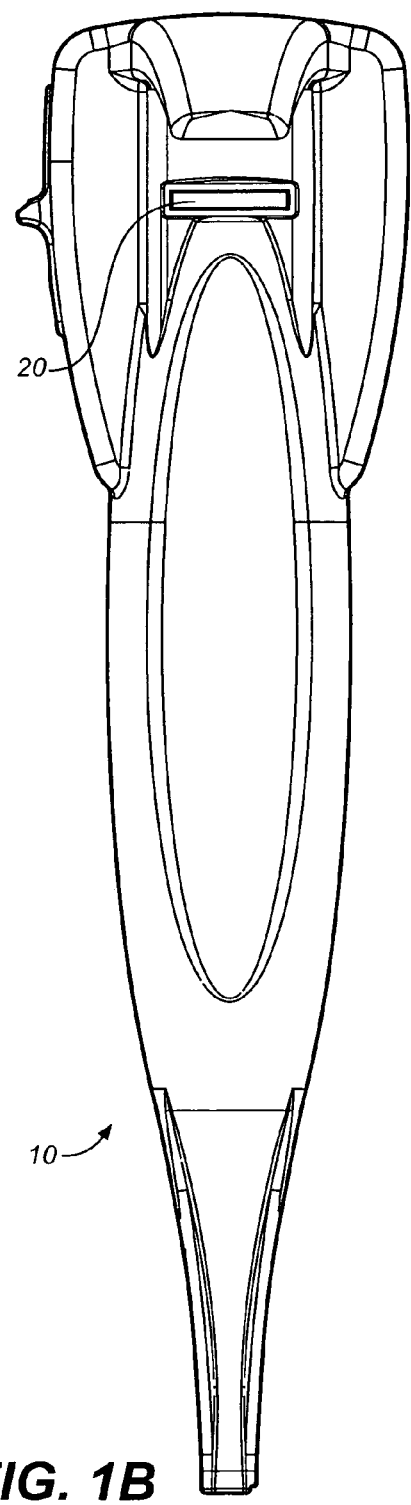
FIG. 1A
FIG. 1B

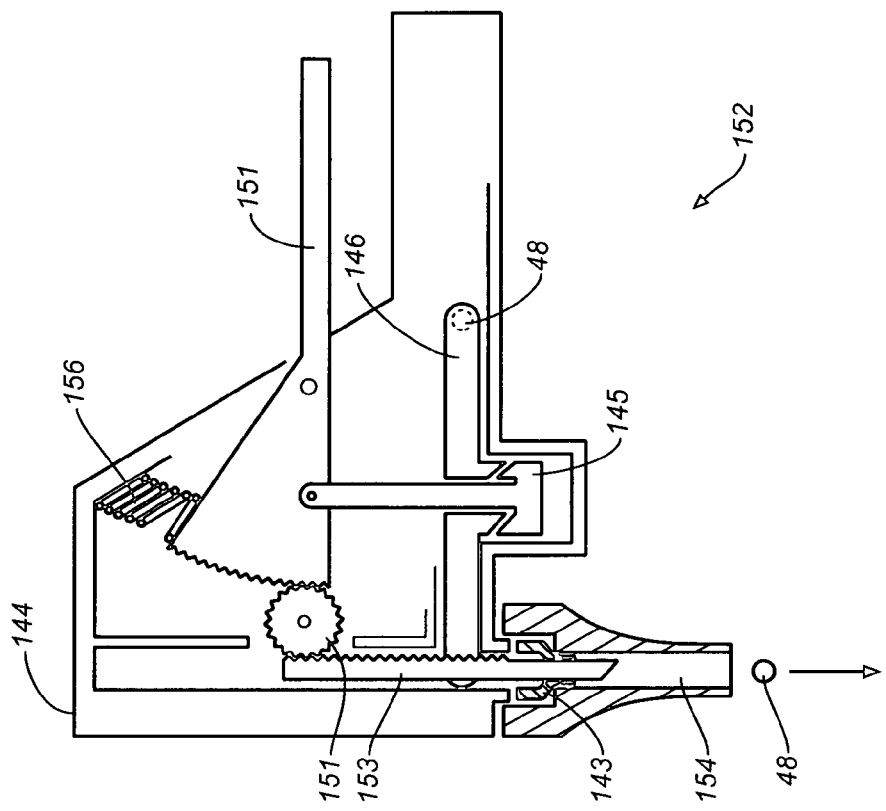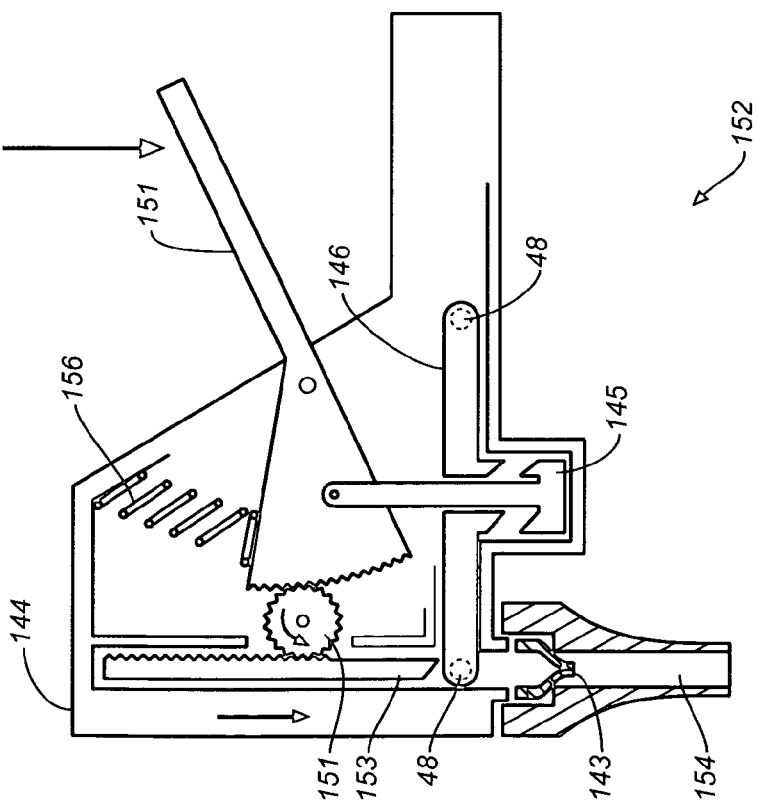

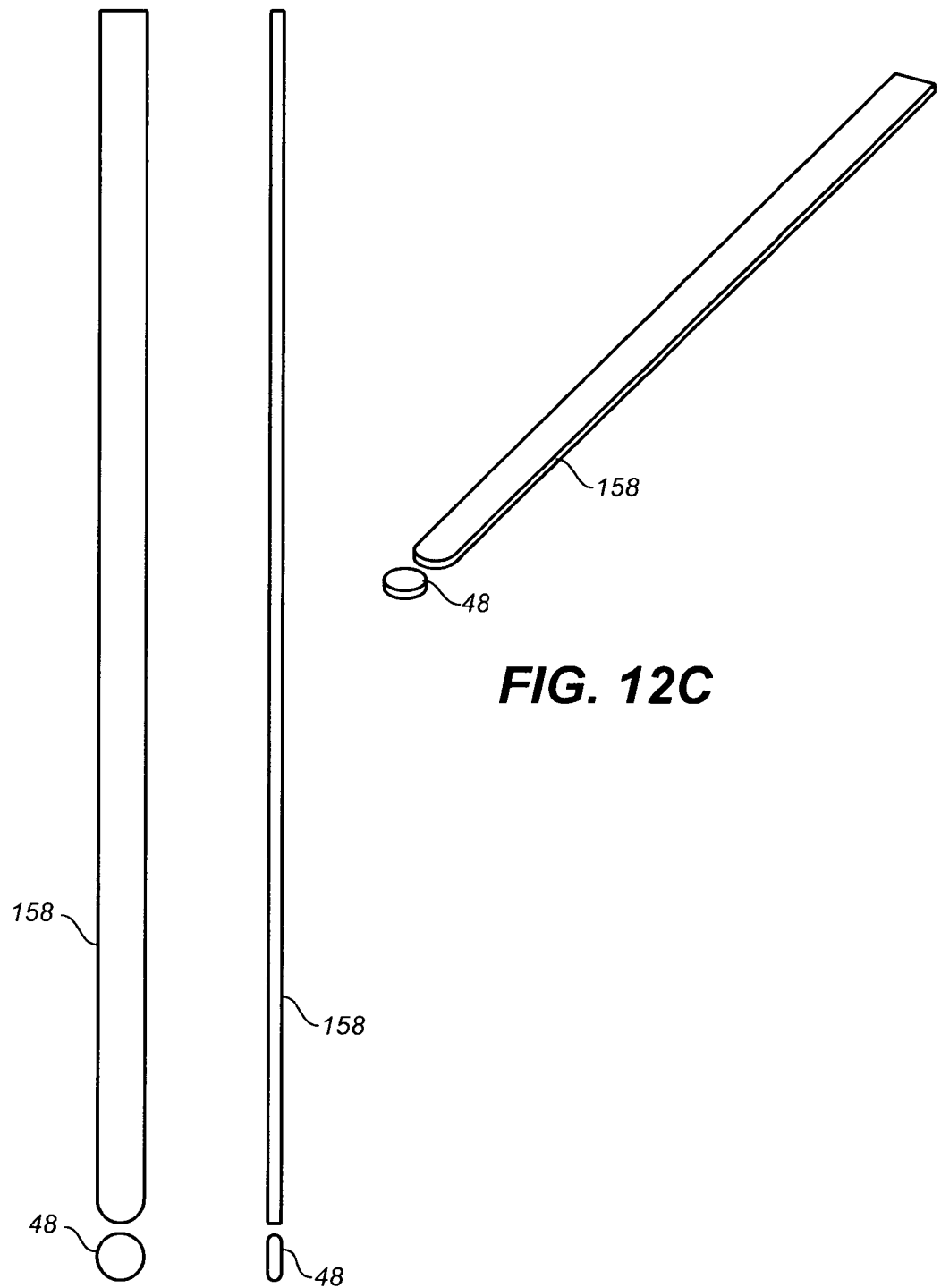
FIG. 12A  FIG. 12B

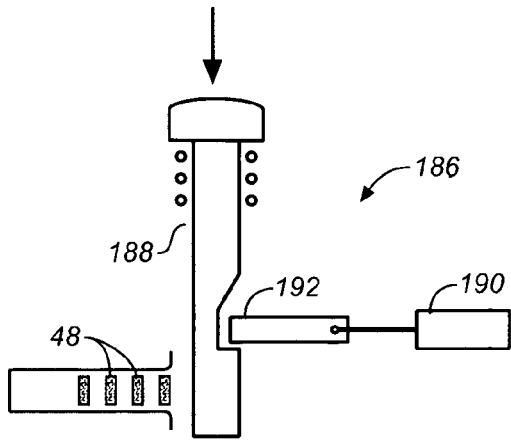
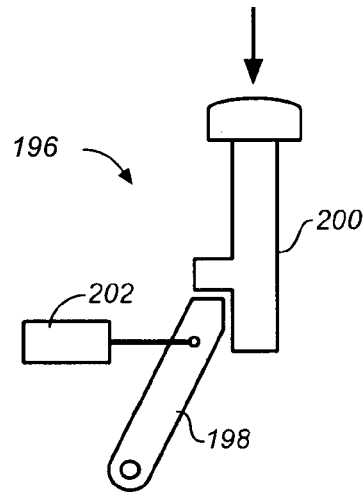
*FIG. 15A*  *FIG. 15B*
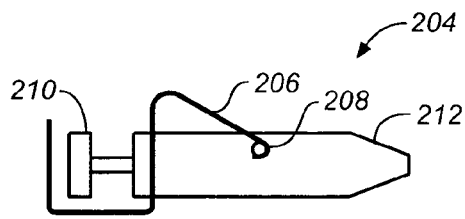
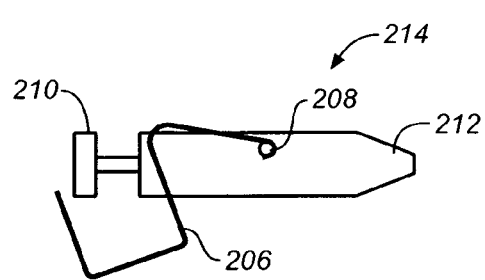
*FIG. 15C*  *FIG. 15D*
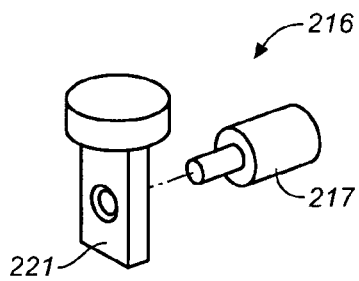
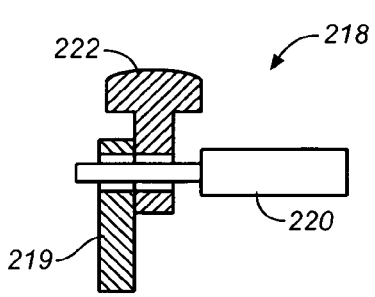
*FIG. 15E*  *FIG. 15F*

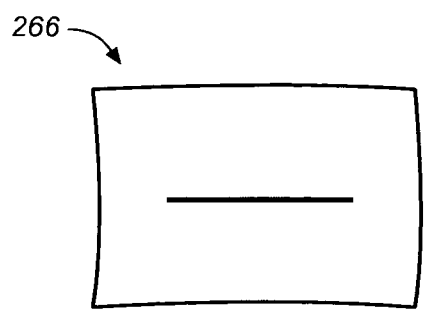
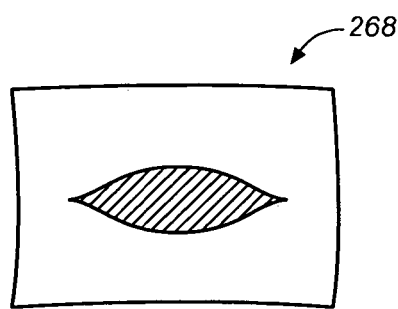
FIG. 19A  FIG. 19B
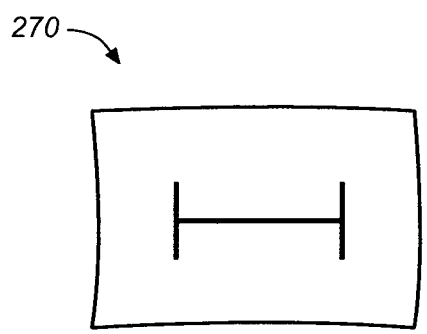
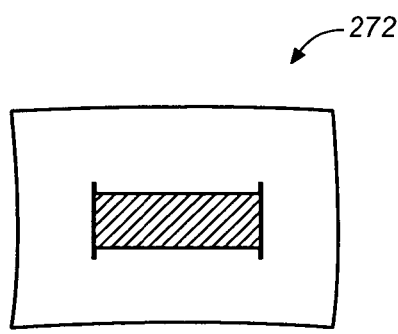
FIG. 19C  FIG. 19D
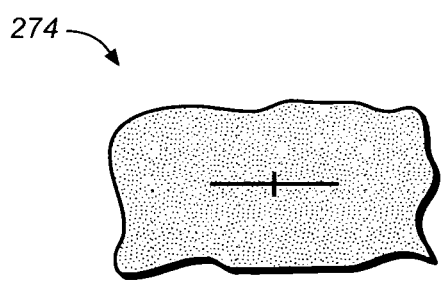
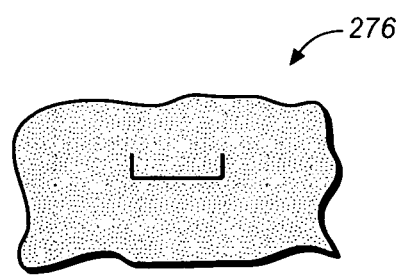
FIG. 19E  FIG. 19F

368

370

DRUG DISPENSING DEVICE WITH FLEXIBLE PUSH ROD

CROSS REFERENCE TO OTHER APPLICATIONS

This application claims the priority benefit of U.S. Provisional Application No. 60/756,937, filed Jan. 6, 2006, the disclosure of which is incorporated herein by reference in its entirety.

FIELD OF THE INVENTION

The present invention relates to dispensing devices for administration of drug dosage forms and systems comprising them. The invention further includes a dispensing device that provides a means for detecting the identity of the patient, a lock-out feature and a means to prevent unauthorized access to stored drugs.

BACKGROUND OF THE INVENTION

Currently, standard medical devices for repeated therapeutic administration of drugs in both the in-patient and out-patient setting including routes of administration, formulations and dosage control have clear limitations with regard to both efficacy and toxicity.

Controlled drug delivery and dispensing technology represents an area of active research and controlled drug delivery systems offer numerous advantages as compared to current drug delivery systems, which include improved safety, improved patient compliance and convenience.

U.S. Patent Publication No. 20050054942 discloses systems and methods for monitoring therapeutic drug concentration in the blood by detecting markers, upon exhalation by a patient after the drug is taken, using electronic sensor technology and a reporting system.

U.S. Pat. No. 6,824,512 discloses a closed loop system for monitoring drug dose, intake and effectiveness which includes a pill dispenser in data communications with at least one implantable medical device. The system includes high speed computers and databases relating to patient history and device information.

U.S. Pat. No. 6,190,326 discloses a system for collecting patient respiratory information which includes a base unit and a removable mouthpiece.

U.S. Pat. No. 6,039,251 discloses a method and system for controlling an in-home medical device, such as a drug delivery pump, wherein a control program or "prescription" for control of the device is encoded on a portable card. Data relating to the device can be saved to the card, and a security program is provided which ensures that only authorized patients can use the medical device. Remote access to the medical device is provided through a communication system between the controller for the medical device and a remotely located computer.

U.S. Pat. No. 5,752,620 discloses a pill dispenser, comprising a container constructed to hold a plurality of pills, with a pill release mechanism provided to dislodge the pill from the pill holder by pneumatic pressure and sensors located on the exit port to detect the presence of a dispensed pill, which is recorded by an attached computer. Optionally, a locking device is attached to the pill dispensing units to prevent unauthorized dispensation of medication.

U.S. Pat. No. 5,710,551 discloses a system for the remote monitoring of in-home self-medication to assure compliance with prescribed dosage schedules.

U.S. Pat. No. 5,945,651 discloses a medication dispensing system including a relatively small, microprocessor-controlled machine that assists in the accurate execution of a physician-prescribed medication regimen. The machine can be used as a stand-alone unit, or can be integrated into a centrally-controlled pharmaceutical network.

U.S. Pat. No. 5,995,938 discloses a medication compliance system having an output device and a computer in communication with the output device for use in printing a label.

The relevant art does not describe a dispensing device that does not require the opening and closing of a lid or other hinged aperture for delivery of drug dosage forms.

Although currently available drug dispensing devices have been effective in the administration of a variety of types of drugs, there remains a need for improved devices for self-administration of drugs that provide for safe and controlled access. There is a further need for drug delivery device which provides for improved safety and ease of use including, for example: a security feature that would prevent unauthorized access to the stored drugs, a lock-out feature to deter overdosing, a dose counting feature, a memory means for retaining information about dose delivery, a theft deterrent feature to theft in hospital, and an interface for exchanging information with another device such as a computer.

There is, therefore, substantial interest in the development of improved devices and systems, for drug delivery, for example for the treatment of acute, intermittent and breakthrough pain, in both the hospital and out-patient settings.

SUMMARY OF THE INVENTION

The present invention provides dispensing devices for dispensing a drug dosage form to a patient, wherein the device comprises a means to dispense multiple doses, a single dose at a time.

Application of dispensing device of the invention is not limited to any particular type of drug or patient population. As such, the dispensing devices of the present invention find utility in drug delivery to pediatric, adult and non-human mammalian subjects.

The present invention further provides dispensing devices for dispensing a drug dosage form to a patient, wherein the device comprises at least one cartridge filled with a plurality of individual drug dosage forms.

The drug dispensing devices of the invention may include a detecting means for detecting the identity of a patient or user. Such detecting means is typically proximal to the dispensing device and is designed to prevent accidental or intentional tampering, abuse, or access to the drug dosage form by unauthorized individuals.

In some embodiments, a dispensing device of the invention has a theft deterrent means to deter theft, e.g., in the hospital setting an exemplary theft deterrent means includes an RFID tag affixed to a patient and an RFID tag reader in the dispenser.

The drug dispensing devices of the invention also may include a programmable lock-out feature for locking the dispensing device, such that dispensing is not possible when the dispensing device is locked.

The drug dispensing devices of the invention may be capable of repeated dispensing of a drug dosage form. In such drug dispensing devices the dispensing mechanism provides a mechanical or electromechanical means for dispensing the drug dosage form.

The drug dispensing devices of the invention may provide a means for minimizing saliva influx into the dispensing device during administration of the drug to the patient.

In some embodiments of the present invention, a means for communication between a dispensing device of the invention and a computer network is provided. The drug dispensing devices of the invention may further include a bidirectional communication link with a local or remote computer system, wherein the computer system provides a signal that allows the dispensing device to dispense a drug dosage form.

In some embodiments the present invention provides a dispensing device for repeated dispensing of a drug dosage form to a patient, in which an access control means for controlling abuse or accidental or inadvertent misuse is provided. The dispensing device is designed such that only authorized persons, such as patients or healthcare professionals, can activate the device.

In some embodiments the present invention provides a dispensing device for repeated dispensing of a drug dosage form for oral transmucosal administration to a patient, e.g., wherein the dosage form is a Nanotab® having a size selected from the group consisting of, a volume of from about 0 to about 100 microliters, and a mass of from about 0.01 to 100 mg, a diameter of from about 1.0 to about 30.0 mm, a thickness of from about 0.25 to about 10.0 mm, and a density of from about 0.01 to 2.0 g/ml. The small-volume drug delivery dosage forms or nanotabs of the invention may have a volume of from about 0.1 to about 50, from about 0.5 to about 10.0, from 1.0 to about 25 or from about 3.0 to about 15.0 microliters, e.g., 5.0 microliters; a thickness of from about 0.25 to about 10.0 mm; from about 0.5 to about 3.0 mm, e.g., about 1.0 mm; and a diameter of from about 1.0 to about 30.0 mm, from about 1.0 to about 10.0 mm, e.g., about 2.5 mm. The dosage form is sufficiently small and can be physically fragile and thus may not be amenable to physical handling and is intended for delivery via a dispenser that allows for convenient administration. A typical dosage form is a substantially homogeneous composition which comprises active ingredients and one or more of bulking agents, binders, flavors, surfactants, mucoadhesins (also referred to herein as "bioadhesins"), lubricants, other excipients and factors that affect dissolution time. The present invention relates to small-volume oral transmucosal drug delivery dosage forms, dispensing devices to dispense such dosage forms and systems comprising them. The present invention provides formulations that produce a reduced saliva response when compared with other oral dosage forms, thus providing high absorption rates of the pharmaceutically active substance across the oral mucosa, and reduced delivery to the gastrointestinal tract, which is particularly useful for drugs with poor bioavailability in the GI tract.

In one exemplary embodiment the invention provides a method for the treatment of pain treatable by an oral transmucosal dosage form in a subject, by administering to the subject a therapeutically effective dose of a small-volume drug dosage form or Nanotab® using a dispensing device of the invention. The dispensing device may be operated using a mechanical method, an electromechanical method and/or both.

In some embodiments the invention provides a system for dispensing a drug dosage form or using a dispensing device as described hereinabove. The dosage form dispensing system includes a drug delivery device with a detecting means for detecting the identity of a patient, a drug dosage form provided in a cartridge or as individual dosage forms and a patient.

BRIEF DESCRIPTION OF THE DRAWINGS

FIG. 1A is a schematic depiction of an exemplary dispensing device of the invention wherein the device is designed to deliver drug dosage forms to the sublingual space of a patient under treatment, wherein a graphic display, a biometric patient identification reader, a dispensing button, a user interface, and a housing in which a dispensing cartridge is located are illustrated.

FIG. 1B is a schematic depiction of an exemplary dispensing device of the invention wherein the device is designed to deliver drug dosage forms to the sublingual space of a patient under treatment, wherein a docking connector is illustrated.

FIGS. 7A through 7D illustrate various stages of the lockout mechanism related to dispensing drug dosage forms.

FIG. 11A depicts an additional embodiment of a dispensing device of the invention, wherein a disc type dispensing mechanism at rest position is illustrated.

FIG. 11B depicts the dispensing mechanism of FIG. 9A at a dispensing position.

FIGS. 12A-12C depict an exemplary pushrod designed for dispensing a drug dosage form.

FIGS. 15A-15F are schematic depictions of exemplary lockout devices, such as a pushrod type device (15A), lockout on actuator type device (15B), safety button/latch type device (15C/15D), solenoid type device (15E), and another solenoid type lockout device (15E), respectively.

FIGS. 19A-F are schematic depictions of geometries of other exemplary slit type septum seals designed to maintain a uniform seal around a drug dosage form and a pushrod during delivery of the drug dosage form.

FIG. 22A depicts a system communication diagram comprising a radio frequency identification (RFID) tag, a dispensing device, a base station/dock and a healthcare provider personal computer. FIG. 22B depicts a system communication diagram comprising an RFID tag, a dispensing device, a fob (or portable handheld docking device) and a healthcare provider personal computer.

FIG. 23A is a schematic depiction of symmetric drug dosage forms including round discs with flat, concave, or convex faces, ellipsoids with flat, concave, or convex faces, spherical, polygons with 3 or more edges and flat, concave, or convex faces. or any other curved solid body.

FIG. 23B is a schematic depiction of asymmetric dosage forms.

DETAILED DESCRIPTION OF THE INVENTION

Figures 1C, 1D:
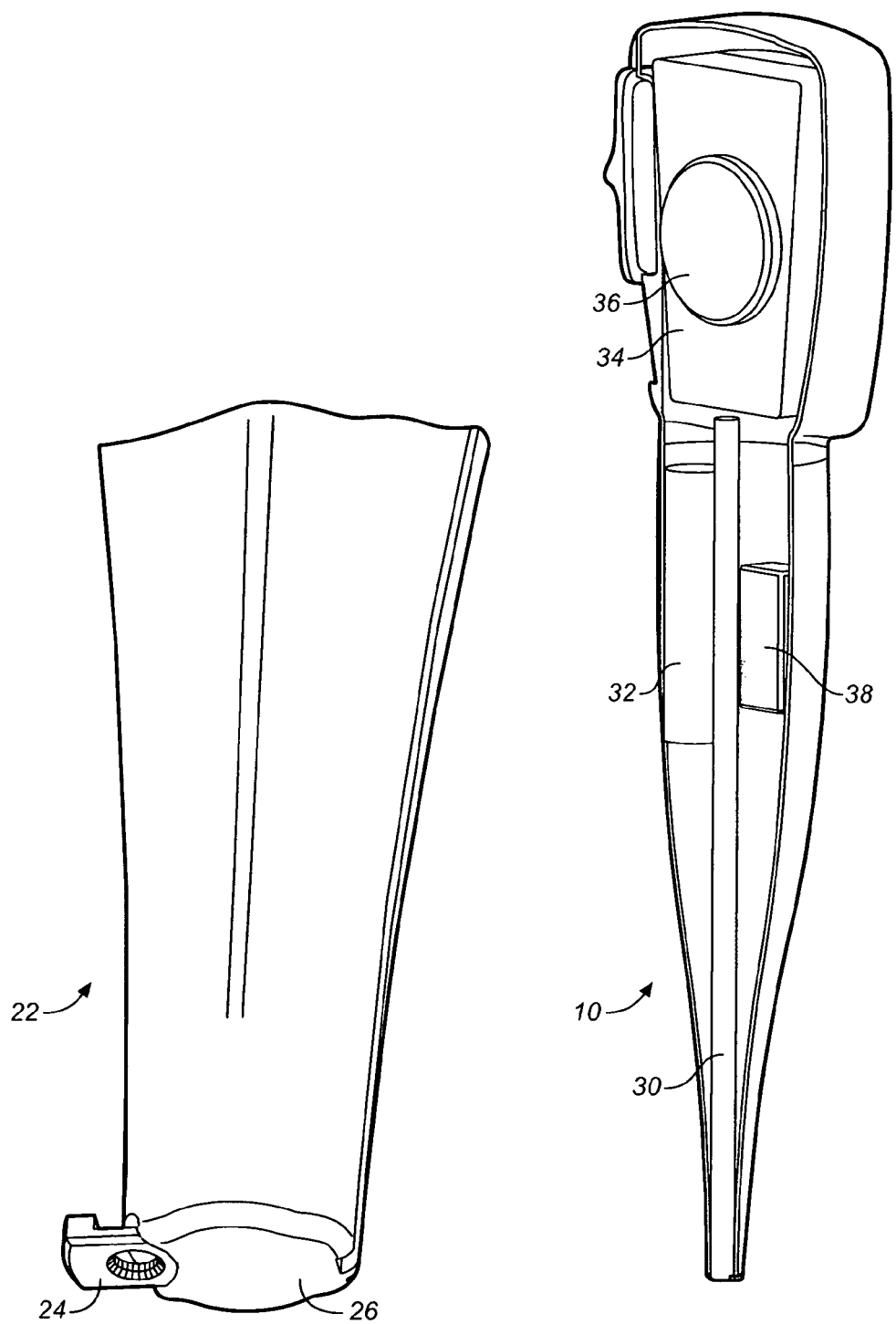
FIG. 1C is a schematic depiction of an exemplary dispensing device of the invention wherein the device is designed to deliver drug dosage forms to the sublingual space of a patient under treatment, wherein a dispensing shuttle mechanism and a dispensing end are illustrated.
FIG. 1D is a schematic depiction of an exemplary dispensing device of the invention wherein the device is designed to deliver drug dosage forms to the sublingual space of a patient under treatment, wherein a cartridge assembly; batteries; processor and pc board; antenna; and antagonist reservoir are shown.

The following disclosure describes the dispensing devices, systems and methods which constitute the present invention. A detailed disclosure of the devices, systems and methods of the present invention for administration of a drug dosage are provided herein below. The present invention generally encompasses: (1) drug dispensing devices; (2) a system that includes a dispensing device and a drug dosage forms; and (3) methods for operating the dispensing devices and systems.

The present invention is generally directed to dispensing devices for dispensing any of a number of types of dosage forms by way of a number of different routes of administration, methods of using such dispensing devices and systems comprising the same.

In one exemplary embodiment, the present invention provides a system, comprising: (1) dispensing devices for administration of small-volume dosage forms, such as a NanoTab®; (2) a small-volume oral dosage form, such as a NanoTab®; and (3) a patient.

In one aspect of this embodiment, a dispensing device of the invention may be used to deliver a small-volume dosage form for oral transmucosal delivery of a medication for the treatment of pain. In further aspects of this embodiment, the invention provides methods and systems for operating a dispensing device of the invention and uses thereof in the treatment of pain, such as acute pain, post-operative pain or break through pain. In one example of this embodiment, the dosage form is a NanoTab® comprising an opioid such as sufentanil or an analogue thereof wherein the dispensing device is used to administer the dosage form for the treatment of pain.

The invention is not limited to the specific devices, systems and methodology or syndromes described herein, as these may, of course, vary. It is also to be understood that the terminology used herein is for the purpose of describing particular embodiments only, and is not intended to limit the scope of the present invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug formulations and devices for containment, storage and delivery of such formulations.

All publications mentioned herein are incorporated herein by reference in their entirety for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

DEFINITIONS

The terms "formulation" and "drug formulation" or "drug dosage form" as used herein refer to a physical composition containing at least one therapeutic agent, which may be provided in any of a number of dosage forms for delivery to a subject. The dosage form may be provided to the patient as a lozenge, pill, capsule, membrane, strip, liquid, patch, film, gum, gel, spray or other form.

The term "drug" as used herein is generally meant to refer to any substance that alters the physiology of an animal. The term "drug" may be used interchangeably herein with the terms "therapeutic agent", "medication", "pharmacologically active agent" and the like. It will be understood that a "drug" formulation of the invention may include more than one therapeutic agent, wherein exemplary combinations of therapeutic agents include a combination of two or more drugs.

The term "subject" includes any subject, generally a mammal (e.g., human, canine, feline, equine, bovine, ungulate etc.), adult or child, in which treatment for a disorder is desired.

The term "transmucosal" delivery of a drug and the like is meant to encompass all forms of delivery across or through a mucous membrane. In particular, "oral transmucosal" delivery of a drug includes delivery across any tissue of the mouth, pharynx, larynx, trachea, upper respiratory tract or upper gastrointestinal tract, particularly including the sublingual, gingival and palatal mucosal tissues.

The term "oral transmucosal drug delivery" as used herein refers to a dosage form wherein drug delivery occurs substantially via the transmucosal route and not via swallowing followed by GI absorption. Such dosage forms are designed to provide for a dissolution rate that allows for maximal delivery via the oral mucosa, typically via placement of the dosage form in the sublingual location.

As used herein, "sublingual", means literally "under the tongue" and refers to a method of administering substances via the mouth in such a way that the substances are rapidly absorbed via the blood vessels under the tongue rather than via the digestive tract. Absorption occurs via highly vascularized buccal mucosa and allows a substance more direct access to the blood circulation, providing for direct systemic administration independent of gastrointestinal influences The term "treatment" or "management" of a medical disorder or condition is used herein to generally describe regression, suppression, or mitigation of symptoms of the medical disorder or condition so as to make the subject more comfortable as determined by subjective criteria, objective criteria, or both.

The term "diversion" is used here to generally describe the act or an instance of diverting the use of a dispensing device and/or drug dosage forms therein from the intended patient to any other unauthorized or unintended individual, whether it is accidental or intentional diversion.

"Device for containing and dispensing the dosage form" or "delivery device", "dispenser", "dispensing device" and the like are used herein to refer to any device adapted for storage and/or delivery of a formulation such as a dosage form, pill, dosage form, lozenge, gel, gum, liquid, strip or film.

"Operatively connected" as used herein means the components are provided in a device so as to function as intended to achieve an aim. For example, a memory device operatively connected to a CPU which is further operatively connected to a release mechanism may be meant to indicate that, upon actuation, the CPU communicates with the memory device to check the status or history of drug delivery, and then further communicates with the release mechanism (e.g., via a solenoid and a switch) to release and dispense a drug.

The term "fob" refers to a small, portable handheld, powered electronic docking device that can be used in conjunction with the dispenser to upload data, download data, control access to the dispenser, control access to the drug dosage forms, or enhance or otherwise alter the user interface of the dispenser. A fob may communicate and dock with a dispenser either in a wired or wireless fashion. A fob may be adapted to attach to a cord so as to allow the fob to hang from the neck of a healthcare professional such as a physician or caregiver, particularly in the hospital setting. A drug dispenser may communicate with the physician or care giver via the fob.

The term "reservoir" refers to a chamber or containment space within a delivery or storage device for storing a formulation to be delivered from the delivery device.

The terms "dispensing device", "drug dispensing device" and "drug delivery device" are used interchangeably herein with the term "dispensing device" and refer to a device that dispenses dosage forms, which are sufficiently small to facilitate controlled delivery and carry a therapeutic dose of medication to the patient. The dosage forms of the invention can be physically fragile and thus may not be amenable to physical handling. The dispensing device provides a mechanism for controlled and safe delivery of the medication formulated in the dosage forms of the invention.

The term "systems that include a drug dosage form and a dispensing device" as used herein refers to a drug dispensing system for delivery and monitoring of drug administration. A system of the invention may be used to monitor and deliver both efficacious and maximum dosages such that the amount of drug delivered, corresponding efficacy, and safety are enhanced over currently available systems. The system may have one or more features that provide for improved safety and ease of use over currently available systems including a security feature that prevents unauthorized access to the stored drugs, a theft deterrent feature that helps prevent theft, a dosing lock-out feature, a dose counting feature, a memory means for retaining information about dose delivery, and an interface for bidirectional exchange of information with a user or another device such as a computer.

The term "acute pain" is used herein with reference to pain that is typically present for less than one month, however, in some cases pain that is present for as long as three months may also be considered to be "acute" if the specific pain episodes are themselves of shorter duration.

The term "chronic pain" is used herein with reference to pain that is typically present for longer than one month.

Types of Dispensing Devices

Outpatient Acute Setting

One exemplary use of a dispensing device is to provide a rapid-acting dosage form that produces a therapeutic effect rapidly, may be used safely and conveniently, and provides a therapeutic effect for an appropriate period of time. The dispensing device of the invention may be used in the outpatient setting. In the outpatient setting, one embodiment of the dispensing device of the invention may exhibit the following structural and functional features: the dispensing device may be a standalone portable model; the dispensing device may be capable of up to several weeks of treatment; the dispensing device may be disposable, and/or non-refillable; the dispensing device may be child proof; the dispensing device may have a fixed lockout between doses; the dispensing device may exhibit a shutdown after a fixed period of time; the dispensing device may have an interface limited to a dispense button, sounds or tones, and LEDs; the dispensing device may monitor the temperature and shutdown if the drug dosage exceeds safe limits; a display; and the dispensing device may have a dose counter.

When used in the outpatient acute (home, office, field, etc.) setting, the dispensing device of the invention offers several features and advantages over the state of the art in outpatient drug administration. The dispensing device allows individuals to self administer drugs in accordance with physician, healthcare provider, or drug label guidelines. Some exemplary acute outpatient indications are post-operative pain, pain associated with physical trauma, anxiety, insomnia, hypertension, angina, coronary artery disease, depression, psychosis, constipation, nausea, addiction, ADHD, and others. See, e.g., U.S. application Ser. No. 11/429,904, expressly incorporated by reference herein. To effectively assist in the dispensing of drugs in the acute outpatient setting, the dispensing device may provide some or all of the following features: allow the patient to self administer the medication; record a dosing history; allow the dosing history to be read or transferred to a computer, network or other electronic device; deter tampering or diversion; deliver the drug dosage form to the appropriate location (e.g. sublingual, buccal, oral gastro-intestinal, rectal, ocular, nasal, inhalation, aural, transdermal or any other route of administration); and notify a pre-determined individual or individuals (by alert, alarm, cell phone message, text message, email, or other wired or wireless communication means) of an event like a dosing administration, a need for a refill of a prescription, a tamper attempt, a misuse of the device, a GPS location, an expiration of the drug contained in the device, a temperature or humidity event. The dispensing device of the invention may be used to dispense any medication in the outpatient acute setting, in any drug dosage form, affording any combination of the features set forth above. Some examples of uses for a device of the invention are in acute field care for first responders, military field medics, emergency rescue, etc.

For example, treatment of acute pain is often necessary "in the field" under highly sub-optimal conditions. First responders, such as paramedics or military field medics, often are required to treat severe acute pain in non-sterile situations, where needles used for IV or IM administration can result in unintended risk, such as infection, and so on. The dispensing devices, systems and methods of the present invention find utility in this setting as well as in circumstances such as when a subject is suffering from angina, which may be treated with nitroglycerine using a dispensing device of the invention.

Inpatient Setting

Another use for the dispensing device of the invention arises in the inpatient setting. For example, the need for rapid treatment of acute pain occurs in many different clinical situations, including post-operative recuperation, rheumatoid arthritis, failed back, end-stage cancer, etc. in the hospital settings. Post-operatively, for example, patients suffer from severe pain for the first few days followed by days of mild to moderate levels of pain.

One embodiment of the dispensing device for drug dosage forms in the inpatient setting may include the following structural and functional features: sufficient drug for 1-5 days of treatment; a dispensing device that is disposable or partially disposable; a dispensing device that may be rechargeable and may have a recharge station/dock/portable docking fob; a dispensing device that may have a graphic display on the device; a dispensing device that may have docking station or fob; a dispensing device that may have a keypad on the device; dock, or fob; a dispensing device that may be queriable regarding dosing history; a dispensing device that is typically capable of identifying authorized users and has controlled access; a dispensing device that may have a counter reset function; a dispensing device that is typically child proof; a dispensing device that may have a fixed or variable lockout time; a dispensing device that may be refillable; a dispensing device that may be capable of dosing feedback; a dispensing device that may connect up to a wireless or wired network, device, or computer for real-time update; a dispensing device that is typically theft deterrent; and may have a reusable head.

When used in the inpatient (hospital, clinic, etc.) setting, a dispensing device of the invention offers several features and advantages over the state of the art in patient drug administration. The dispensing device allows healthcare providers to provide drug dosage forms to a patient for self administration of PRN ("Pro Re Nata") medications. PRN refers to drugs that are taken as needed, such as for pain, nausea, constipation, anxiety, etc. To effectively operate in the inpatient setting, a PRN patient controlled dispensing device should allow the patient to self dose as needed, prevent the patient from over dosing, record the dosing history, allow for the dosing history to be read, downloaded, or otherwise transferred to a patient's records, deliver the drug dosage form to the appropriate location (e.g. sublingual, buccal, oral gastrointestinal, rectal, ocular, nasal, pulmonary, vaginal, aural, transdermal or any other route of administration) and prevent or deter unauthorized individuals from gaining access to the drugs. The dispensing device of the invention may be used to dispense any PRN medication in any drug dosage form in the inpatient setting affording any combination of the features set forth above, as described in U.S. application Ser. No. 11/473,551, which is expressly incorporated by reference herein.

A system comprising the dispensing device of the invention may have a portable dock which bidirectionally transmits information from the device to a network in a wired or wireless mode. Software for downloading or uploading data, such as dosing histories, to a computer system is also part of this embodiment of the invention.

Outpatient Chronic Setting

Yet another embodiment of a dispensing device of the invention is in the outpatient setting where chronic administration is needed for patients suffering from chronic conditions.

One embodiment of the dispensing device for delivering drug dosage forms in dispensing device may be capable of 1-2 years of treatment; the dispensing device may be rechargeable and may be part of a system which includes a recharging station/dock/portable docking fob; the dispensing device may have a graphic display and indicator lights on the dispensing device; the dispensing device may be part of a system which includes a dock, or fob; the dispensing device may include a keypad on the device; the dispensing device may include a dock, or fob; the dispensing device may record a dosing history; the dispensing device may allow the dosing history to be queried; the device may store one or more patient or user identifications; the dispensing device is typically theft deterrent, child proof and has controlled access, the dispensing device may have a resetable counter; the dispensing device may have fixed or variable lockout times; the dispensing device may be refillable; the dispensing device may be networked; and the dispensing device may have an alert function.

When used in the outpatient chronic (home, office, field, etc.) setting, the dispensing device offers several features and advantages over the state of the art in outpatient drug administration. The dispensing device allows individuals to self administer drugs in accordance with physician, healthcare professional, or drug label guidelines. Examples of chronic outpatient indications where a dispensing device of the invention finds utility include chronic pain, chronic breakthrough pain, anxiety, insomnia, hypertension, coronary artery disease, depression, psychosis, addiction, ADHD, high blood pressure, diabetes, and others. To effectively assist in the dispensing of drugs in the chronic outpatient setting the dispensing device may provide some or all of the following features: the dispensing device may allow the patient to self administer the medication; record a patients' dosing history; allow the dosing history to be read or transferred to a computer network or other electronic device; allow a physician or healthcare provider to modify the settings and programming either in person or remotely; automatically upload or transfer information at a pre-determined time, on a pre-determined schedule or upon a specific event taking place; deter tampering or diversion; deliver the drug dosage form to the appropriate location (e.g. sublingual, buccal, oral gastro-intestinal, rectal, ocular, nasal, inhalation, aural, transdermal or by any other route of administration); and notify a pre-determined individual or individuals (by alert, alarm, cell phone message, text message, email, or other wired or wireless communication means) of an event like a dosing administration, a need for a refill of a prescription, a tamper attempt, a misuse of the device, a GPS location, an expiration of the drug contained in the device, a temperature or humidity event. A dispensing device of the invention may be used to dispense any medication in the outpatient setting, in any drug dosage form, affording any combination of the features set forth above.

In some embodiments, the dispensing device includes a docking connector or wireless docking means and is capable of communicating with a system which includes software and access to a computer network. A system comprising this device has a stationary or portable docking station which bidirectionally transmits information from the device to a network by wired or wireless mode or the hook-up may be by way of a docking connector or a wireless docking means, together with a means of connecting to a phone line, a computer, or a network.

Physical Aspects of a Drug Dispensing Device of the Invention

There is a continuing, unfilled need for a drug dispensing device that can accurately dispense a given medication to the correct patient in a manner that is cost-effective, minimizes the risk of error, is resistant to accidental and intentional abuse and diversion, eliminates the need to handle the medication and is not labor-intensive.

In another embodiment, the present invention provides a drug dispensing device that greatly simplifies the logistics of dispensing single and multiple doses of a given medication under controlled conditions. One exemplary use of a drug dispensing device of the invention is in the administration of controlled substances such as opioids. In such cases, the dosage form contains a highly potent and controlled narcotic drug that must be contained and administered under controlled conditions. Storage and delivery of such a formulation requires a specially designed device. The device must safely store the dosage form, prevent or deter abuse or accidental or inadvertent misuse, readily and accurately allow dispensing of individual dosages only to the patient for whom the drug was prescribed in an efficacious and safe manner as well as provide a means for monitoring and reporting of the history of use. The drug dispensing devices of the present invention meets these needs.

In another embodiment, the dispensing device comprises a package that holds a single or multiple drug dosage forms, a distal orifice for delivery of the drug dosage form, an internal mechanism that segregates and releases the dosage forms, internal electronics that control the number of dosage forms that can be delivered in a given time period (lockout time), a security feature that limits access to the device to the patient and/or one or more healthcare professionals, a security feature that reduces likelihood of dispensing device theft, a queriable interface that allows for dispensing device use history information to be stored and retrieved, a means of preventing saliva from penetrating the device, and an external switch for the user to actuate the dispensing device. The dispensing device is typically handheld and may be capable of data communication by way of a docking station ("dock"). A fixed or portable dock may be incorporated to aid in charging the dispensing device and for data access by authorized healthcare professionals. The dispensing device is capable of shutting down if a user does not match patient ID, lockout period has not expired when a dosing attempt is made, or sensors indicate that the drug form is no longer good (due to humidity, heat or expiration). The dispensing device is capable of issuing alarms when functional issues arise. In one aspect of this embodiment, the drug dosage form and drug dispensing device are designed for oral transmucosal drug delivery, e.g., into the sublingual space.

In another embodiment, the dispensing device of the invention includes a detecting means for patient identification such as a fingerprint reader, an optical retinal reader, a voice recognition system, a face recognition system, a dental imprint recognition system, a visual recognition system, or a DNA reader. The dispensing device may employ one or more means to identify the user, enabling the system to determine if a dispensing request is being made in an authorized or unauthorized manner. It is important for effective delivery of many potential drugs and drug dosage forms to ensure that the dispensing device is not accidentally or intentionally used by an unauthorized individual to prevent accidental or intentional diversion of the drug. Such patient identification systems may recognize one or more users, for example, in an inpatient hospital setting the dispensing device could be programmed to recognize the patient to whom it is prescribed, as well as authorized healthcare providers such as nurses and physicians. In an outpatient home setting, for example, the dispensing device may only respond to the patient to whom it is prescribed. The dispensing device may employ any means of user identification, including fingerprint identification, RFID detection with the use of an active or passive RFID tag on bracelet, necklace, clip, belt, strap, adhesive patch, implant, or means of locating and affixing a tag, retina identification, DNA identification, voice recognition, password or code entry, physical key, electronic or magnetic key, personal area network identification using the human body or clothing as a data or signal conduit, optical scanner or face recognition, sonic, subsonic or ultrasonic identification, or any other means of identifying an individual and verifying their identity.

One method of patient identification is the use of a short distance ("near field") passive RFID tag attached to a bracelet, necklace, adhesive patch, clothing tag, orally mounted device, like an orthodontic retainer, belt, strap, some combination of these, or another location. When an RFID tag is used in the "near field", roughly defined as about 16% of the wavelength of the received signal, the tag behaves in the inductive mode of operation, coupling between the reader and tag antenna magnetically. The near field is characterized by at least two features: first is a rapid decline in field strength with distance, and second is a strong directionality of the signal. In the near field, the signal strength falls off very rapidly, with a signal strength loss of approximately 60 dB per decade in distance. For good inductive coupling between the transmitter antenna and the RFID tag antenna, the two antennas are oriented in parallel planes with the axes through the center of each antenna in close proximity. Strong signal strength (robust patient identification) is provided when the device is very close to the RFID tag. At the same time, a very poor signal is provided when the device is further away from the tag, which helps prevent unauthorized use by someone other than the patient who attempts to use the device. It is preferable to operate in this near field region with good antenna alignment. Furthermore, it is preferable to operate with a very short distance of adequate signal strength for a positive identification, so that it is very difficult to receive a signal if the device is not in the proper orientation and proximity to the RFID tag. To attain a short distance and a proper alignment between antennas, the dispensing device may be designed so as to properly locate the RFID reader antenna, mounted in the dispensing device, adjacent to an RFID tag antenna, mounted, for example, on a wrist band or bracelet, or a clothing tag on the collar, or an adhesive patch on the hand, arm, cheek, neck, or elsewhere. Furthermore, an RFID tag antenna on a wrist band or bracelet may be held in proper alignment and location by means of a small adhesive patch that prevents the bracelet from moving or rotation on the wrist.

In another embodiment, the dispensing device employs a high frequency RFID reader for use in the inpatient (hospital, clinic, etc.) setting, operating on or near the 13.56 MHz frequency band, and the patient is be fitted with a matching RFID tag and antenna on a disposable bracelet or wrist band, designed in such a way that if the bracelet or wrist band is removed the RFID tag, the antenna, or another component of the associated circuit will be damaged or destroyed, rendering the bracelet or wrist band non-functional. In one example, the range of the RFID communication is short, between 0 inches and 10 inches preferably, more preferably between 0 and 5 inches, and most preferably between 0 and 3 inches, and may additionally be directional, allowing proper use by the intended patient to be easy and reliable, while at the same time making unauthorized use by another individual difficult, very difficult, or impossible.

In another embodiment, the dispensing device of the invention for use in the outpatient setting (e.g. home, office, etc.) would include an electronic fingerprint sensor system and would be trained to identify the patient's fingerprint at the time of prescription or first use. When the intended patient doses herself, she would first use the fingerprint identification sensor to attempt identification. Once the dispensing device has successfully identified the patient as the authorized user of the device, the dispensing device would allow a single dosing, effectively unlocking itself for a brief period of time, for example 5 seconds. Once the dose has been delivered or the 5 seconds have elapsed the dispensing device would effectively re-lock itself, requiring another fingerprint identification prior to another dosing.

In another embodiment, the dispensing device of the invention allows for a heart rate measurement, and does not dispense a dose unless the patient's heart rate is within a pre-specified range. The dispensing device may have any of a number of a number of types of sensors for measurement of internal and external parameters including biometric parameters such as body temperature, respiratory rate, blood pressure, blood chemistry, saliva chemistry, breath chemistry, or any other biological state or detectable input, or include external parameters such as time, date, temperature, humidity, global position, etc.

In another embodiment, the dispensing device of the invention may have a dose counting feature that monitors and stores the history of drug usage, including a global dosing counter that counts all doses taken since the device was set up, and a resettable dosing counter that may be reset by authorized medical personnel, e.g., a nurse and tracks doses taken since the last reset. The dispensing device of the invention can count and display the number of doses which have been dispensed and the number of doses that are remaining to be dispensed.

In addition, in another embodiment, the dispensing device of the invention may have a memory means for retaining information about the dose delivered over time. The memory means may include RAM and/or ROM. A central processing unit (CPU) for processing information and controlling various functional elements of the device is also provided.

In another embodiment, the dispensing device of the invention may also have a convenience feature that can provide for ease of use. Exemplary convenience features include disposability, reusability, ease of refill, remote wired or wireless activation, rechargeable batteries, and multiple dose capability.

In another embodiment, the dispensing device of the invention may also have a drug expiration alert feature that can prevent inappropriate dosing of an expired drug; drug expiration information; an interface for exchanging information with another device such as a computer; a clock feature to track date and time for drug access control; and/or other communication capabilities that may be time dependent.

In another embodiment, the dispensing device of the present invention provides a drug delivery device that is capable of controlled delivery that is electrically monitored and controlled such that the patient receives a dose that is both safe and efficacious.

In another embodiment, the drug dispensing device of the present invention is an easily handled, portable, self powered, relatively inexpensive device that allows for timed lock-out periods to avoid overdosing, is child-proof and tamper proof, and is capable of multi-unit dosing, such that days, weeks or months of medication can be housed in the device.

In another embodiment, the drug dispensing device of the present invention may include the following structural components which are functionally connected: a drug reservoir, a dispensing tip, a manual or powered activation trigger or button, one or more communication port(s), an internal power supply, a user interface with input and output functions, a microprocessor, wireless communication capability, patient and user identification (e.g. fingerprint reader, RFID) capability, saliva ingress prevention, internal humidity and moisture control, an opioid antagonist reservoir, a refilling or other access port, one or more sensors to detect internal and external states, and biometric or access code input.

In another embodiment, the drug dispensing device of the invention may employ one or more sensors inside or outside of the dispensing device to monitor various inputs. Some inputs may be indicators of internal system states, such as the number of tablets in the device, the location of tablets within the device, the successful dispensing of a tablet, an unsuccessful dispensing attempt, the presence of a tablet at a specific location, the presence of a tablet cartridge, the identity of the cartridge, the position of the dispensing mechanism, the temperature or humidity within the device, or the sensing of any other internal configuration or state. Other inputs may be indicators of conditions external to the device, including temperature, humidity, acceleration, light, or proximity to a user, another person, or an object, among others. These inputs may be specific to a user or other person and may include direct or indirect interactions with the device, actuation or activation of a switch, button, or other input, body temperature, heart rate, respiratory rate, blood pressure, blood chemistry, saliva chemistry, breath chemistry, pupil dilation, or any other biologic state or detectable input. The sensors may employ any means of detecting an input. A range of sensors for detecting temperature, humidity, acceleration, saliva ingress, or other biometric input may serve as a means to allow the device to activate or shut down under predetermined or programmable conditions.

In another embodiment, the drug dispensing device may be powered by a battery, capacitor, fuel cell, or other power supply source, or may require no electrical power, but be manually activated.

In some embodiments, the drug dispensing device of the invention includes a battery that can be charged by a photovoltaic cell or manually by a hand-actuated crank or lever. A rechargeable battery or other power source may be recharged in a dock, with a recharging cable, or by other means.

FIG. 1A is a schematic depiction of one embodiment of a dispensing device 10 for delivering drug dosage forms to a patient. The dispensing device 10 includes a graphic display 12, a biometric patient identification reader 13, a user interface 14, a dispensing button 16, and a housing 18 in which a dispensing cartridge is located. The dispensing device 10 is constructed to hold a plurality of dosage forms. The graphic display 12 includes an LCD display that enables the dispensing device 10, for instance, to monitor and display dosing frequency, patient information, and/or schedule information. The user interface 14 may used for navigating and selecting menu items displayed on the graphic display 12. The dispensing button 16 may dispense single doses when pushed by a user, such as a patient. This allows post operative or otherwise incapacitated patients to operate the device without undue physical exertion. It also allows an attending nurse or physician to dispense a dose to the patent and monitor their dosing history. The dispensing button 16 may either actively dispense a dosage form or trigger a logic switch that will inform a processor within the device that a dispense request has been made. The patient identification reader 13 requires input of identification (e.g. fingerprint reader, optical retinal reader, voice recognition, dental recognition, face recognition system, or DNA reader, RFID) or an access code to prevent accidental or intentional diversion or abuse from unauthorized individuals.

In one exemplary embodiment, the dispensing device 10 may employ a high frequency RFID reader for use in the inpatient (hospital, clinic, etc.) setting, operating on or near the 13.56 MHz frequency band, wherein the patient is fitted with a matching RFID tag and antenna on a disposable bracelet or wrist band, designed in such a way that once the bracelet or wrist band is removed the RFID tag, the antenna, or another component of the associated circuit is damaged or destroyed, rendering the bracelet or wrist band non-functional. In one example, the range of the RFID communication is short, between 0 inches and 5 inches, and may additionally be directional, allowing proper use by the intended patient to be easy and reliable, but at the same time making unauthorized use by another individual difficult, very difficult, or impossible.

In another exemplary embodiment, the dispensing device 10 for use in the outpatient setting (e.g. home, office, etc.), the biometric patient identification reader 13 is an electronic fingerprint sensor system and would be trained to identify the patients' fingerprint at the time of prescription or first use. When the intended patient doses herself, she would first use the fingerprint identification sensor to attempt identification. Once the dispensing device 10 has successfully identified the patient, the patient identification reader 13 prevents the possibility of accidentally or intentionally switching devices with another patient and an accidental or inadvertent misuse of the device 10.

FIG. 1B is a schematic depiction of the dispensing device 10 for delivering drug dosage forms to a patient. In this embodiment, the dispensing device 10 includes a docking connector 20. The docking connector 20 can allow the dispensing device 10 to connect to another device, peripheral, or computer to retrieve, store, communicate data to the other device, peripheral, or computer.

FIG. 1C is a schematic depiction of one embodiment of a dispensing tip 22 of a dispensing device for delivering drug dosage forms to a patient. The dispensing tip includes a dispensing shuttle mechanism 24 near a dispensing end 26.

FIG. 1D is a cross-sectional schematic depiction of another embodiment of the dispensing device 10 for delivering drug dosage forms to a patient. The dispensing device 10 includes a cartridge assembly 30; one or more batteries 32; a processor and pc board 34; an antenna 36; and an antagonist reservoir 38. The dispensing device 10 may contain a shuttle mechanism, such as shuttle mechanism 24, to remove a drug dosage form from a stack and the dispensing end may have a slider mechanism to dispense single doses when the dispensing button is pushed.

The dispensing device of the present invention may comprise one or more of the following features: be hand held or portable; comprise a graphic display, interface buttons, scroll buttons and a dispensing button; comprise a biometric finger print reader or other means to identify and confirm that the correct patient is using the device; comprise an RFID reader; comprise a dose counting feature; comprise a memory means for retaining information about dosing history; comprise an interface for bidirectional exchange of information with another device such as a computer; comprise an LED, light, sound or tactile indicator that is activated when a dosage form is dispensed; be capable of dispensing a single dosage form at a time; not require the opening and closing of a lid or other hinged aperture in order to dispense a dosage form; comprise an antagonist reservoir; comprise an indicator, wherein the indicator notifies a patient when it is time to take a dose or comprise an indicator, wherein the indicator provides notification in the event of a potentially dangerous or non-efficacious dosing situation or comprise an indicator, wherein the indicator notifies the patient of the remaining time to the end of the lockout period.

In some embodiments, the dispensing device of the invention has the visual look of a pipette (as shown, for instance, in FIG. 1A) and therefore is not enticing to a child (as opposed to the ACTIQ lozenge which has the look of a lollipop).

In other embodiments, the dispensing device can be adapted to attach to a cord so as to allow the device to hang from the neck of the patient or to be affixed to the hospital bed, for example. This would help avoid misplacing the device or theft of the device, such as in the hospital setting. The dispensing device may also have a clip so that it can be attached to an article of clothing or to a hospital bed.

The dispensing device may employ one or more theft deterrent features to prevent or deter unauthorized theft of, or tampering with the device or the drug dosage forms therein. Such deterrents may be employed to prevent theft of, or tampering with the device within the hospital, clinic, or healthcare setting, within the home, office, or any other location where the device is intended or not intended to reside or function, whether temporarily or permanently. Exemplary deterrents include physical locks, tethers, cables, clamps, or other physical attachments, whether permanent or temporary, to another object or to a person.

An exemplary embodiment of a physical theft deterrent means is a flexible cable that locks to the dispensing device on one end and locks, by means of a loop, locking mechanism, or other attachment, to a hospital bed on the other end. In this embodiment the cable tether may be unlocked from either the drug dispensing device or from the hospital bed to enable patient ambulation or to enable disposal or reuse of the device by means of a key, combination, or other locking mechanism that affords controlled access.

The deterrent means may include alarms or notifications that may trigger an alert on the dispensing device, on a dock or other peripheral device; on a computer or by means of a wired or wireless network, or may alert other remote devices. The alarm or notification may be audible, tactile, visual, or may employ other means of notifying one or more individuals. In one embodiment such an alarm or notification may indicate that the dispensing device has been stolen or is in the process of being stolen. In addition to an alarm, information about the theft event may be transferred to or from the device, including the time, date, audio data, visual data, GPS or other location information, or any other information that aids in the prevention of or tampering with the dispensing device or tablets therein. Such deterrents may involve an activation of a feature of the dispensing device, including a loud siren alarm, an electric shock, a shutting down or destruction of one or more aspects of the device, the dispensing of an ink or other marker, or an action that renders the internal drug unusable or undesirable. The dispensing device of this invention may use one or more means to deter theft or tampering.

One exemplary embodiment of such a deterrent means can be exemplified by the case of the delivery of a sublingual opiate tablet in the inpatient (e.g. hospital or clinic, etc.) setting. In such a case the dispensing device includes a wireless proximity detection, like RFID or a detector for a wireless network, to detect when the dispensing device is removed from a predetermined proximity to a person, object, or physical location. Upon detecting that the dispensing device has been removed from a predetermined location or proximity, the dispensing device would shut down normal functionality, sound an audible alarm, send a wireless alert message to a remote device or network, and trigger the internal release of a liquid into the tablet cartridge in such a manner as to wet and/or inactivate all tablets, rendering them unusable.

In another exemplary embodiment, the dispensing device of the invention is used for delivery of a sublingual opiate dosage from in the outpatient (e.g. home, office, etc.) setting, an internal sensor or switch would detect when the dispensing device was opened, disassembled, damaged or lost power in an unauthorized or unintended fashion. The detection of this event would cause the internal micro processor to log an event record, if the system were able to, and trigger the internal release of a liquid opiate antagonist, like naloxone, into the tablet cartridge in such a manner as to wet all tablets, rendering them unusable as a opiate drug and unusable as a sublingual tablet dosage from.

In one exemplary embodiment, the dispensing device is a handheld device, with a control interface on one end and a dispensing device tip on the other. The control interface has a number of features, selected from an LCD monitor screen (for example, the graphic display 12 shown in FIG. 1A), a speaker for user feedback, various interface and/or scroll buttons (for example, the user interface 14 shown in FIG. 1A), a dispensing button (for example, the dispensing button 16 shown in FIG. 1A), and a biometric thumbprint reader (for example, the biometric patient identification reader 13 shown in FIG. 1A). The dispensing end may have a slider mechanism (for example, the user interface 14 shown in FIG. 1A) to dispense single doses when the dispensing button is pushed.

The dispensing device may employ one or more levels of interface for different types of authorized users, for example the patient, the nurse, the physician, pharmacist or other authorized medical or healthcare personnel. These different interfaces may include components such as keypads, buttons, graphical icons and instructions, lights, LED's, monochrome or color graphical or text displays, touch-screens, LCD's, sounds, tactile feedback, voice recognition interfaces, and other input and output devices and means. The activity, or mode, of the user interface may be determined by the mode of operation of the dispensing device, by a login or access activity by a user such as a password or code entry, by the connection or disconnection of the dispensing device from a dock, computer, or network, or by the detection of an authorized access key, such as a key, and/or RFID tag, or similar combination. Upon changing the interface mode, the functionality of the device may be changed, either activating, inactivating or changing the functionality of the various interface components described above. By allowing the device to have one or more interface modes, with differing functionality associated with each one, the device can be optimized for various uses.

In one exemplary embodiment, a dispensing device of the invention is used for administration of a sublingual tablet in the inpatient (hospital, clinic, etc.) setting. Such a device would contain a microprocessor, a memory means, an LCD text and graphical display, a keypad with several buttons for navigating a graphical menu and selecting functions, and a dispensing mechanism for dispensing a sublingual tablet.

Figure 2:
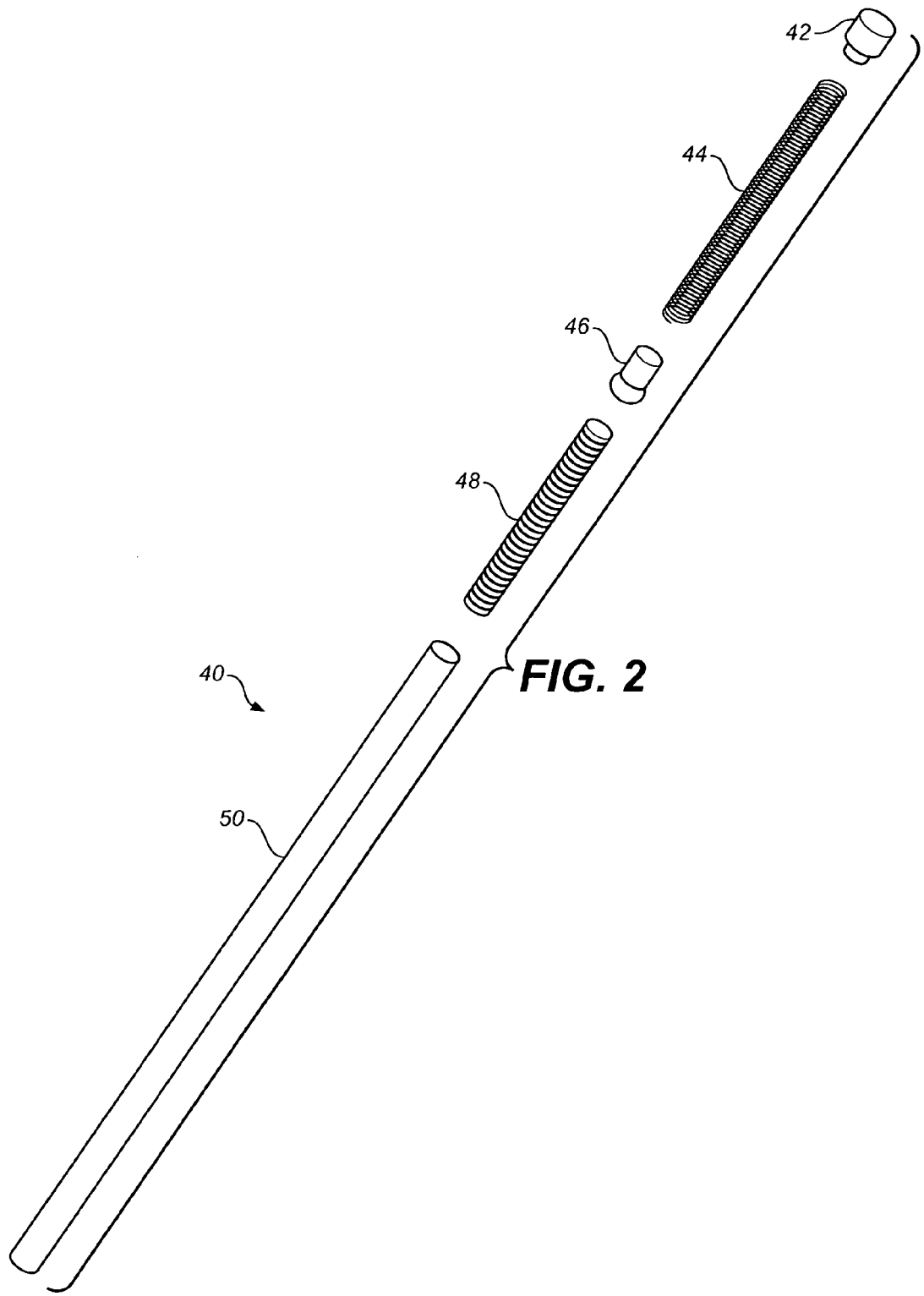
FIG. 2 is a schematic depiction of a cartridge assembly for use in a dispensing device for delivering drug dosage forms.

FIG. 2 is a schematic depiction of a cartridge assembly 40 for use in a dispensing device for delivering drug dosage forms. The cartridge assembly 40 includes a cap 42, a spring 44, a plunger 46, dosage forms 48, and a cartridge tube 50. To assembly, the drug dosage forms 48 are loaded into the cartridge tube 50, followed by the plunger 46, the spring 44 and the cap 42. Once this cartridge is assembled it is inserted into a drug dispensing device, such as dispensing device 10.

Figure 3A:
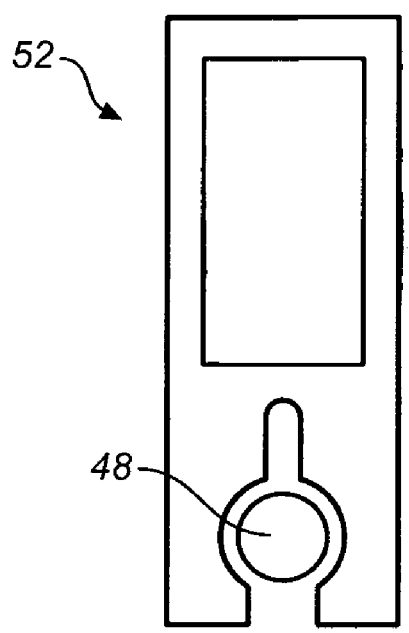
FIGS. 3A and 3B are schematic depictions of an exemplary dispensing device for delivering dispensing drug dosage forms, wherein an exemplary single dose applicator is shown.
Figure 3B:
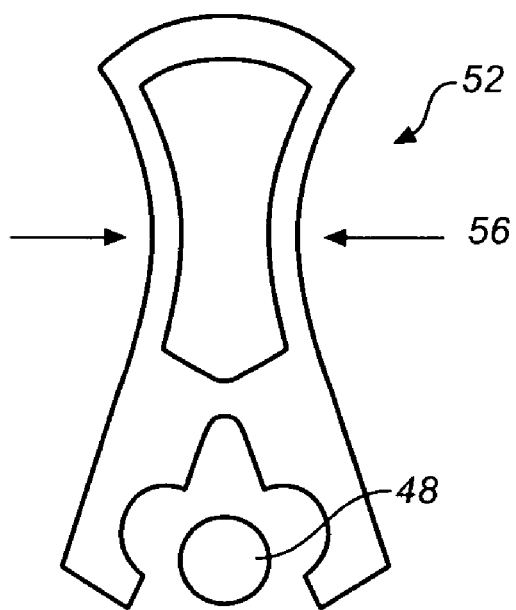

FIGS. 3A and 3B show one embodiment of a single dose applicator 52 of a dispensing device for delivering drug dosage forms. The dispensing device shown in FIG. 3A depicts the single dose applicator 52 that is ready to dispense a drug dosage form 48. In one aspect of this embodiment, a user pinches the single dose applicator 56, which opens the applicator and a drug dosage form 48 is dispensed as shown in FIG. 3B.

The drug dosage form dispenser of the invention may dispense drug dosage forms or it may dispense drug dosage forms attached to or contained within a disposable applicator with means of allowing manual application of said dosage form to a pre-determined location for drug delivery (e.g. the mouth, sublingual space, the eye, etc.). In one embodiment, a single dose applicator may be used for a variety of drug dosage forms, including a solid tablet, a liquid capsule, a gel capsule, a liquid, a gel, a powder, a film, a strip, a ribbon, a spray, a mist, a patch, or any other suitable drug dosage form. The single dose applicator (SDA) may contain the dosage form within, may have the drug dosage form attached or affixed to it, may afford a seal against moisture, humidity, and light, and may be manually manipulated by a patient, healthcare provider, or other user to place said dosage form in the proper location for drug delivery. The SDA may be of the form of a pair of forceps, a syringe, a stick or rod, a straw, a dropper, a sprayer or atomizer, or any other form suitable for the application of a single drug dosage form. After use, said SDA may be disposed of, so as to eliminate the risk of contaminating the dispenser with saliva, or other contaminants.

In another embodiment, a dispenser of the invention may contain a plurality of SDA's, in a cartridge or individually packaged, and may dispense a single SDA containing a single drug dosage form for use by the patient, healthcare provider, or user. The dispenser may dispense single SDA's in the same way and with the same features as would be advantageous for the dispensing of single drug dosage forms described in the invention.

FIG. 3A describes one exemplary embodiment of the SDA of the invention. When the applicator is positioned for delivery and is squeezed, as shown in FIG. 3B, a flexible hinged section deforms, allowing the dosage from to be released into the sublingual space. After applying the dosage form, the dispenser may be disposed.

The dispensing device may employ one or more levels of interface for different types of authorized users, for example the patient, the nurse, the physician or the pharmacist. These different interfaces may include components such as keypads, buttons, graphical icons and instructions, lights, LED's, monochrome or color graphical or text displays, touchscreens, LCD's, sounds, tactile feedback, voice recognition interfaces, and other input and output devices and means. The activity, or mode, of the user interface may be determined by the mode of operation of the dispensing device, by a login or access activity by a user such as a password or code entry, by the connection or disconnection of the dispensing device from a dock, computer, or network, or by the detection of a authorized access key, such as a key, and RFID tag, or similar action. Upon changing the interface mode, the functionality of the device will change, either activating, inactivating or changing the functionality of the various interface components described above. By allowing the device to have one or more interface modes, with differing functionality associated with each one, the device can be optimized for the various user's needs.

One exemplary embodiment of a dispensing device for inpatient (hospital, clinic, etc.) use includes a microprocessor, a memory means, an LCD text and graphical display, a keypad with several buttons for navigating a graphical menu and selecting functions, and dispensing button for dispensing a sublingual tablet. In this embodiment the dispensing device would have two interface modes: a patient mode and a medical personnel mode, e.g., a nurse mode. In a patient mode, only the dispensing button would work, and the display and keypad would be non-functional. In the medical personnel mode, the display and keypad would be functional and a nurse would be able to access the dosing history, the dosage strength, the patient ID, the remaining doses in the device, and any other information that the dispensing device would have for nurse access. A nurse may have an RFID tag that the dispensing device would recognize as a medical personnel access tag, shifting to the medical personnel interface mode when it is present and switching back to the patient interface mode when it is not present.

In another exemplary embodiment, the dispensing device of the invention is used for administration of a sublingual tablet in the inpatient (hospital, clinic, etc.) setting. The dispensing device includes a microprocessor, a memory means, a multi-color LED light, a dispensing button for dispensing a sublingual tablet, and a docking connector or wireless docking means. Additionally, there would be a portable handheld dock that contains a microprocessor, a memory means, a graphical and text display, a keypad, and a docking connector or a wireless docking means. When this dispensing device is used in the patient mode, the LED would display a one color, e.g., green, when patient dosing was allowed, and it would display another color, e.g., an amber color when patient dosing was not allowed because the dispensing device was in a timed lockout period, and the dispensing device would display a third color, e.g., a red color when the dispensing device malfunctioned. The patient would be able to self administer a sublingual tablet when the LED was green. In one scenario, a nurse or other authorized medical personnel would bring a portable dock into the patient's room and physically or wirelessly dock to the dispensing device, allowing the medical personnel interface mode to be operable. In the medical personnel interface mode, a nurse would be able to view the patient dosing history, the dosage strength, the patient ID, the remaining doses in the device, and any other information that the device would have for the nurse to access. Furthermore, a nurse could reset dosing counters on the device, query error conditions, deliver bolus doses if needed, etc. When the portable dock was disconnected from the dispensing device, the dispensing device would return to the patient interface mode.

In another exemplary embodiment, the dispensing device of the invention is used for administration of a sublingual tablet in the outpatient (home, office, etc.) setting. The dispensing device includes a microprocessor, a memory means, a dispensing button for dispensing a sublingual tablet, a small electronic speaker, and a docking connector or wireless docking means. Additionally there would be a stationary docking station that would contain a microprocessor, a memory means, a docking connector or a wireless docking means, and means of connecting to a phone line, a computer, or a network. In the patient dosing mode, the patient would depress the dispensing button when a dose was required. If the patient presses the dispensing button during the timed lockout period between doses, a tone would sound, informing the patient that he must wait before re-dosing and the dispensing device would not dispense a tablet. If the patient presses the dispensing button after the timed lockout period between dosing has expired, then the dispensing device would dispense a tablet and a confirmatory tone would sound, informing the patient that a dose had been dispensed. When the dispensing device is docked, either physically or wirelessly, to the stationary dock, the dispensing device would communicate with the patient's physician by means of a dock or other communication means to the physician's computer or other device, and exchange information, allowing the physician to view the patient's history, download information, reset a counter on the dispensing device, or enable or disable any other features on the device in a remote fashion. When the dispensing device is removed from the dock, the dispensing device would return to the patient interface mode, unless the physician had instructed the dispensing device to do otherwise.

A drug dosage dispensing device of the invention may deliver tablets or other dosage forms into the hand, the mouth, under the tongue, or to other locations appropriate for specific drug delivery needs. In one embodiment, the dispensing device delivers solid tablets to the sublingual space in the mouth for a sublingual delivery system. In this embodiment, the solid dosage forms inside the dispensing device should remain dry prior to dispensing, at which point a single tablet is dispensed from the dry device into the sublingual space, wherein a patient's saliva will wet the tablet and the tip of the device. A means of preventing saliva ingress into the dispensing device is desired to prevent saliva from entering the dispensing device and wetting the tablets, or to isolate any saliva that enters the dispensing device in such a manner that the tablets therein remain dry, or to absorb or adsorb any saliva that enters the dispensing device in such a manner that the tablets remain dry, or any combination of these methods.

A means of preventing saliva or other moisture from entering the dispensing device may include, but is not limited to, one or more flexible or rigid seals, one or more flexible or rigid wipers, one or more absorbent material components, a door or latch that is manually or automatically opened and closed, a positive air pressure and airflow, or a gap or prescribed distance maintained between the tablet delivery orifice and the mucus membrane tissues within the mouth that may transport the saliva.

FIGS. 4A-4D are schematic depictions of an exemplary dispensing device 58 for delivering drug dosage forms 48, wherein a means for minimizing saliva influx into the dispensing device 58 during the administration of the dosage forms 48 to the patient is provided. The dispensing device 58 includes a pusher/slider 60, a housing 62, a push rack 64, pinions 66, and a channel 68 in the housing and a spring 72.

Figure 4A:
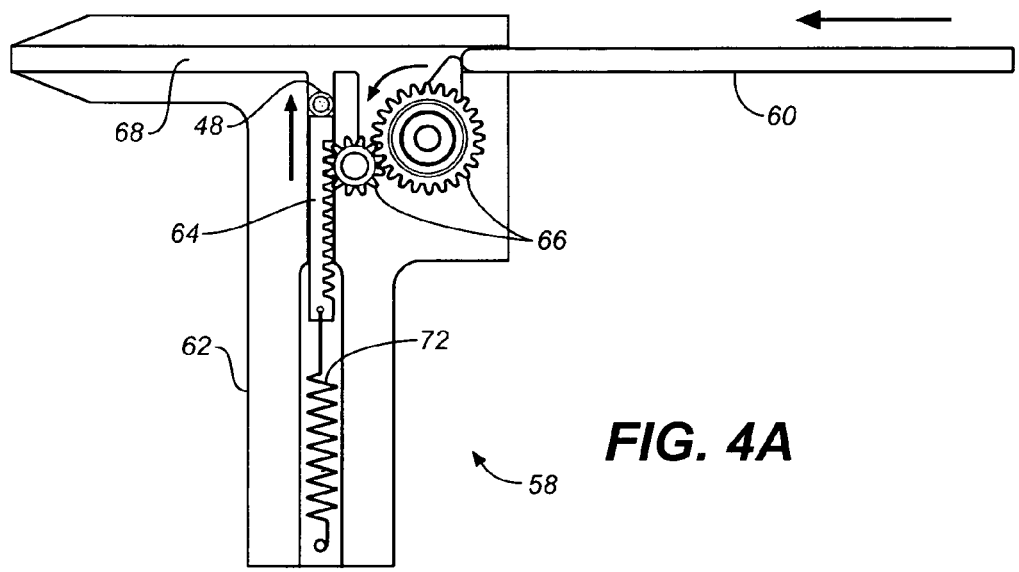
FIGS. 4A-4D are schematic depictions of an exemplary dispensing device for delivering drug dosage forms to the oral mucosa, wherein a means for minimizing saliva influx into the dispensing device during the administration of the dosage forms to the patient is shown.
Figure 4B:
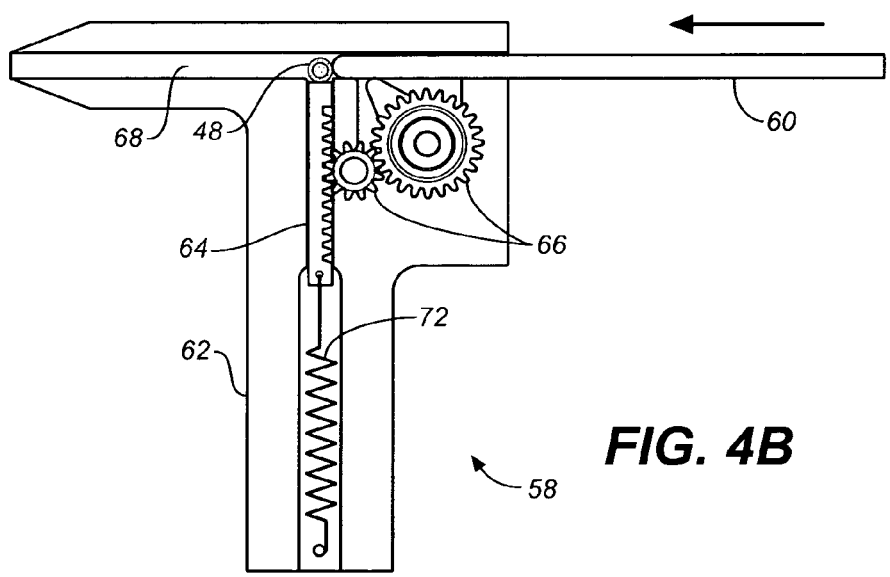
Figure 4C:
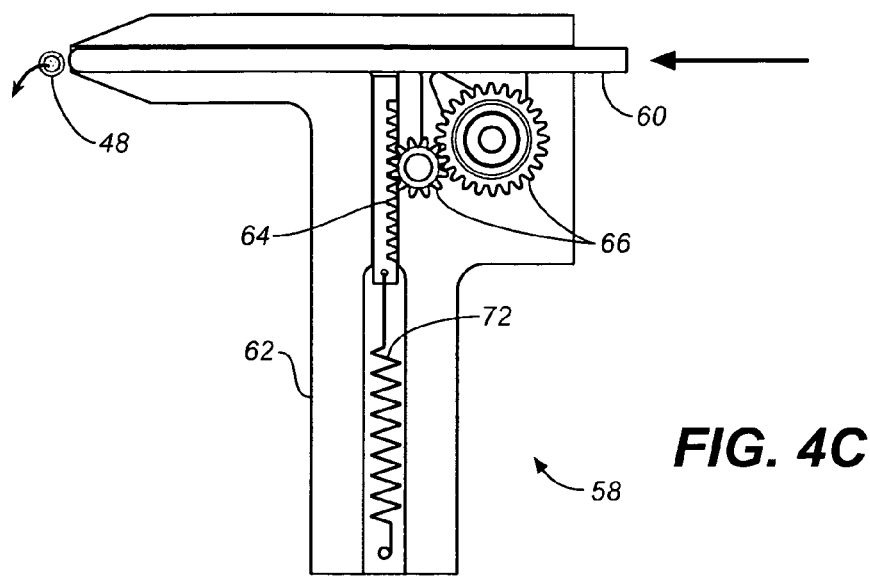
Figure 4D:
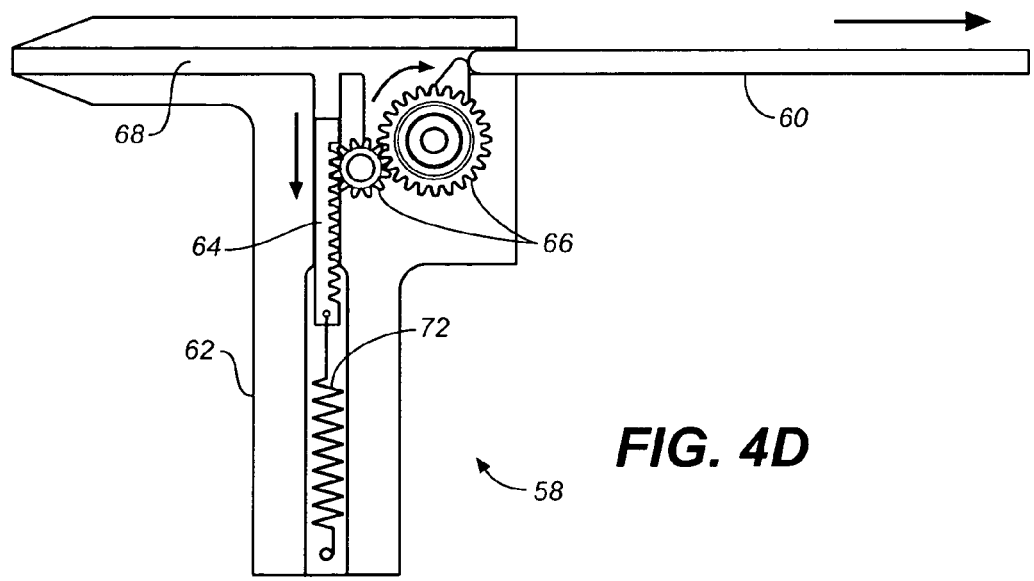

FIGS. 4A-4D depict a multiple stage dispensing of drug dosage forms 48 as a means to reduce saliva ingress into the dispensing device 58. In FIG. 4A, the pusher/slider 60 is ready to push rack 64 and pinions 66 housed in the housing 62 of the device 58. The channel 68 provides space for the pusher 60 to freely move within the channel 68. The drug dosage form 48 is sitting on top of the rack 64 and spring 72 provides necessary tension in moving and returning the rack 64 and mechanism. In the dispensing device 58 shown in FIG. 4B, the pusher/slider 60 is moving the rack 64 and pinions 66 housed in the housing 62 of the device 58. The drug dosage form 48 is pushed upward within the channel 68 by the force provided by the spring 72 on the rack 64. In the dispensing device 58 shown in FIG. 4C, the dosage form 48 is being dispensed from the end of the channel 68 and into a subject, such as human. Then the steps are repeated for successive dispensing of the dosage form 48 minimizing saliva ingress into the device 58 as shown in FIG. 4D. Saliva influx/ingress into the dispensing device 58 may be minimized by inclusion of seals, wipers, absorbents, desiccants, ejection type devices, air gaps, or combinations thereof, or any other means of minimizing saliva ingress in the device design. A means of allowing saliva to enter the device while preventing saliva from reaching the remaining tablets within the device may include one or more flexible or rigid internal wipers or seals, a drug dosage cartridge that contains a plurality of individually packaged or isolated drug dosage forms, a delivery pathway for the tablet from a drug dosage cartridge to the exit port that is tortuous or multi-staged in such a manner that saliva or moisture not capable of wicking up the delivery pathway.

Figure 5:
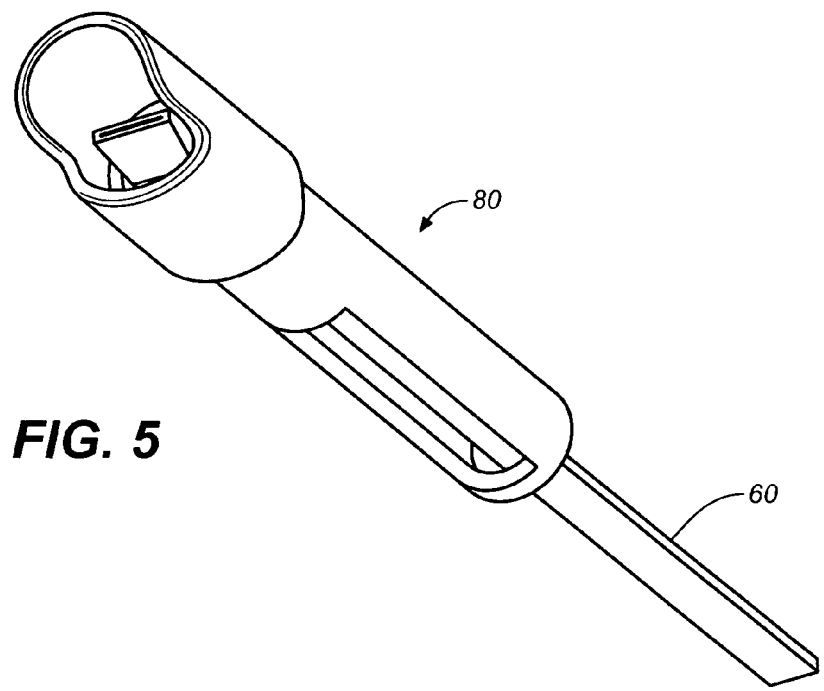
FIGS. 5 and 6 are schematic depictions of an exemplary geometry for a dispensing tip that prevents contact of one or more seals with the moist or wet surface.
Figure 6:
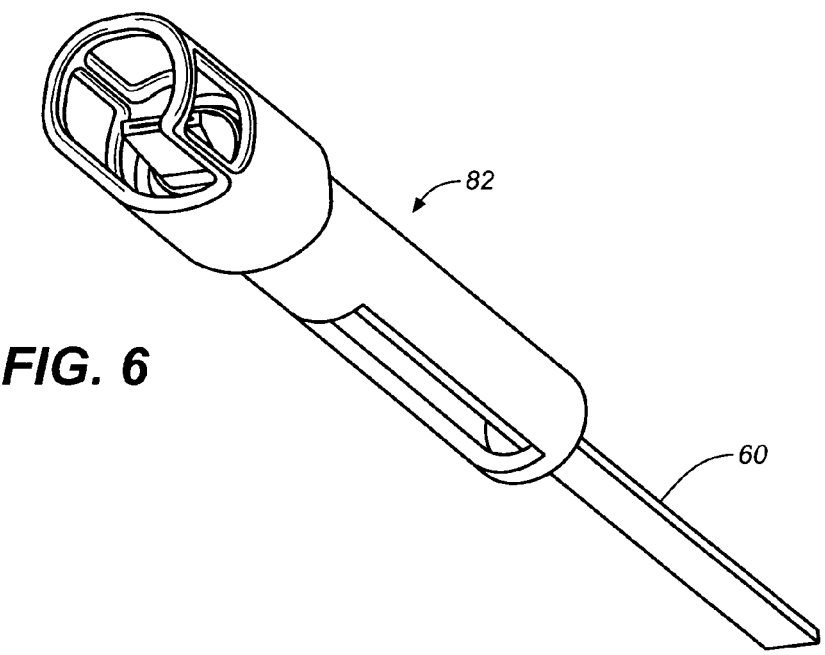

FIGS. 5 and 6 are schematic depictions of an exemplary geometry of a dispensing tip, wherein two means for keeping seals dry are shown. FIG. 5 depicts one example of dispensing device tip geometry 80 and FIG. 6 depicts another example of the tip geometry 82.

In one embodiment, the present invention provides a dispensing device which dispenses multiple dosages of a dosage form to the sublingual area, such that an efficacious dose is delivered while simultaneously providing a timed lock-out feature to prevent accidental overdosing. The dose and corresponding lock-out time may be adjusted dependent upon the size of the subject and the intended therapeutic goal.

The device or dispensing device of the present invention may comprise a timed lock-out feature, wherein the device comprises a means for setting a lock-out interval between dosing, selected from the group consisting of a fixed time interval, a predetermined time interval, a predetermined variable time interval, a time interval determined by an algorithm and a variable time interval communicated to the device from a remote computer or docking station.

The dispensing device may include a lockout feature that prevents dosing the drug in an unsafe or non-prescribed manner. This lockout feature may mechanically prevent the device from dispensing a dose by either locking the mechanism, disengaging a component of the mechanism, or by controlling the dispensing mechanism by means of a microprocessor and an algorithm during the lockout period. The lockout may be of a fixed period (10 minutes, for example), of a predetermined variable period, a "smart" variable period, or a "triggered" lockout based on an internal or external event or state. The fixed lockout would afford a fixed lockout period after each dose, wherein the device will not allow a subsequent dose to be delivered. The pre-determined variable lockout would afford a variable lockout period after dosing, following a pre-determined lockout schedule (for example, the lockout period may increase by one minute following each subsequent dose). The "smart" lockout would afford a variable lockout period based on an internal algorithm taking into account the dosing history, dosing requests, or any other data or inputs that the algorithm may use for determination. For example, the smart lockout may base the lockout period on the dosing history, taking into account the pharmacokinetics of the specific drug molecule, and how the body naturally clears or metabolizes the drug over time. The triggered lockout would respond to internal or external triggers, such as data from sensors (e.g. temperature, humidity, heart rate, respiratory rate, blood pressure), internal signals (date, time, or location from GPS), signals from external computers, networks, or other electronic devices, the presence of a physical, magnetic or electronic key, the receipt of a mechanical or electronic access signal such as a password, code, RFID signal, or any other wired or wireless signal. The dispensing device of the invention may employ one or more of the lockout described herein.

In one exemplary embodiment, the dispensing device has a smart lockout preventing dosing of a tablet for a period of time following an initial dose, based on the dosing history and an internal algorithm. In this embodiment the lockout time is calculated to predict the safe dosing interval knowing the history of drug doses the patient has already taken and the pharamcokinetics of the drug.

In another exemplary embodiment, the dispensing device is programmed to allow dosing for the 72 hour recovery period following a minor outpatient orthopedic surgery procedure. When the device is first prescribed to the patient, the internal clock in the device begins to track the elapsed time. When the elapsed time reaches 72 hours the device locks down, notifying the patient that the dispensing device has expired and will no longer allow dosed to be delivered.

Figure 7A:
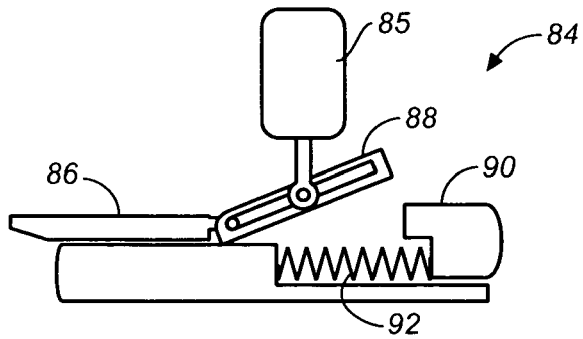
FIGS. 7A-7D are schematic depictions of an exemplary mechanical lockout means, wherein one exemplary locking mechanism is illustrated.
Figure 7B:
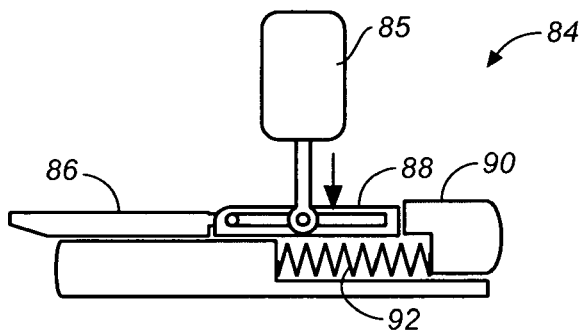
Figure 7C:
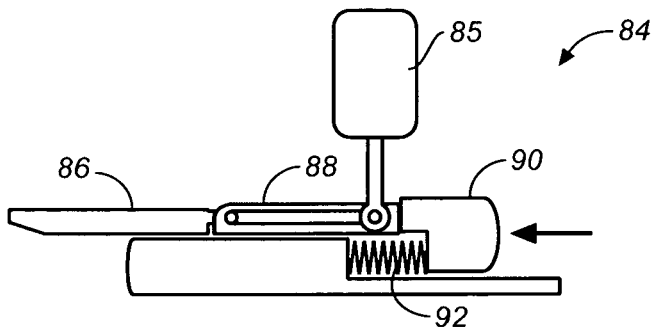
Figure 7D:
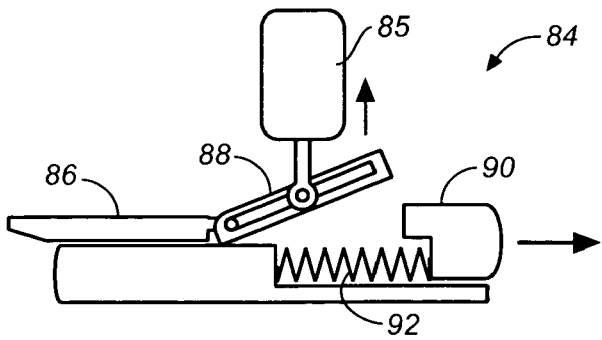

FIGS. 7A-7D are schematic depictions of one embodiment of a drug dispensing mechanism 84 which includes a lockout feature. The drug dispensing mechanism 84 includes a pushrod 86, a lock 88, a button/pusher 90, and a wedge 92. In use, the button/pusher 90 pushes the lock 88 into the pushrod 86. When the lock 88 is raised, the button/pusher 90 is unable to push it and the mechanism is locked. FIGS. 7A through 7D illustrate various stages of a lockout mechanism related to dispensing drug dosage forms. FIG. 7A depicts a situation where a predetermined lockout period has not passed and the dispensing mechanism 84 is still in locked position, with the lock 88 raised. In FIG. 7B, a predetermined lockout period has passed and the lock 88 is in the lowered position and the lockout mechanism allows the dispensing mechanism in dispensing position. FIG. 7C depicts a further step where the dispensing mechanism 84 operates with the button/pusher 90 pushing the lock 88 into the pushrod 86 to dispense drug dosage forms (not shown). FIG. 7D depicts a locked position for a predetermined lookout period for a next dispensing. The locking device may be attached to the drug dispensing device to prevent unauthorized dispensing of the medication. Sensors may be located on the exit port to detect the successful dispensing of a dosage form, which is recorded internally by the dispensing device, or by a wired or wirelessly attached dock or computer. The types of the locking devices may include the following: a movable push rod; a non-returning push rod; an electromechanical regulator; an optical sensor pair; a magnetic clutch; a lockout on actuator; a rack and pinion; a safety button latch; a solenoid; a collet on shaft; a keyed hub; a movable coupling; and a cam.

In another exemplary embodiment, the dispensing device is programmed to allow dosing for the 72 hour recovery period following a minor outpatient orthopedic surgery procedure. When the device is first prescribed to the patient, the internal clock in the device begins to track the elapsed time. When the elapsed time reaches 72 hours the device locks down, notifying the patient that the dispensing device has expired and will no longer allow dosed to be delivered.

The present invention may also provide a means for adjusting both the initial dose and subsequent doses, as well as the lock-out time. Patients can be evaluated to determine the appropriate dosing schedule and lock-out time following an evaluation of drug plasma concentration.

The dispensing device allows for a variable, pre-determined lockout schedule that may vary with length of the prescription, time of day, progression of ailment or symptoms, etc. and may utilize an algorithm to determine the lockout schedule and duration, based on prescription, medication, dosing history, and other patient specific information such as vital signs (e.g., respiratory rate or blood pressure determined by a non-invasive means), taken together with pharmacokinetics of the active drug agent.

If the patient does not achieve sufficient therapeutic benefit from a single administration, the advantage of the repetitive dosing feature with lock-out is that the patient can re-dose, thereby titrating their plasma levels of drug in a safe manner. This can be repeated until a therapeutic plasma level is achieved.

An initial dose and lock out time for a dispensing device of the invention is set upon initiation of treatment depending upon the age and weight of the patient and medical history. However, the initial dose and lock out time may subsequently be adjusted dependent upon patient response, duration of treatment and the like.

The initial timed lock-out period for a dispensing device of the invention is typically from about 1 minute to about 60 minutes, from 3 minutes to 40 minutes or from 5 minutes to 30 minutes, and in particular cases is set at any one minute interval from 1 to 60 minutes, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

The present invention provides a dispensing device with a programmable lock-out feature for locking the dispensing device when the device is locked. This prevents or deters abuse or accidental or inadvertent misuse. The lock-out feature operates by a means selected from the group consisting of a movable pushrod, a non-returning pushrod, an electromechanical regulator, an optical sensor pair, a magnetic clutch, a lockout on actuator, a rack and pinion, a safety button latch, a solenoid, a collect on shaft, a keyed hubs, lead screw, rotary actuator or mechanism, a movable coupling, and cams.

The present invention provides a dispensing device with an access control means for controlling abuse or accidental or inadvertent misuse other than by a healthcare professional. The dispensing device will not function if the cartridge is not loaded, locked-in, and activated by the healthcare professional.

The dispensing device of the invention may be used multiple times or be disposable such that it is discarded when all of the medication initially loaded into the device has been dispensed.

The invention further contemplates the use of a dispensing device of the invention for delivery of small volume dosage forms that are solids, liquids, suspensions, films, gels, sprays, mists, foams, tapes, patches, or pastes. Accordingly, the invention provides dispensing device which can provide for a pre-determined delay between doses in a liquid or gel dispensing device. The mechanism includes a liquid or gel reservoir that is slightly pressurized, for example by a propellant or a spring loaded plunger, a thin exit tube leading from the reservoir to a second cylinder chamber. The cylinder chamber may contain a dispensing piston attached to a rod, and a dispensing port that is much larger than the thin exit tube connecting to the reservoir. The dispensing port may include a valve to prevent unintended dispensing of the drug. The viscosity of the drug formulation, the pressure in the reservoir, and size of the thin exit tube may be designed such that the viscous drug formulation slowly flows from the pressurized reservoir to the cylinder chamber, driving the piston backward until the chamber is full. This process takes a period of time that may be pre-determined and coordinated with an appropriate lockout time between drug doses. When the cylinder chamber is full, the dispensing valve may prevent drug from escaping. To dispense drug from the cylinder, the rod is pressed. The actuation of the rod also opens the dispensing valve allowing the liquid or gel to be dispensed. In one approach, the dispensing port is much larger than the exit tube, such that the drug is preferentially driven out the dispensing port. Also, it is possible to dispense a drug using this system prior to the cylinder chamber being completely full. If the chamber fills at a constant rate, the amount of drug dispensed is proportional to the time that the chamber has been filled, up to the point that the chamber is completely filled. For this reason, if the dispensing device is actuated prematurely, the dispensing device will only dispense a partial bolus of liquid or gel.

In one embodiment, the dispensing device of the invention includes a means to produce an audible, visual, or tactile signal when the drug is administered (such as a click, beep or visual indication such as a light) to provide feedback to the patient that a dosage has been dispensed. In the example of a small sized dosage from such as a NanoTab® dosed sublingually, the patient may not be aware of the drug in their sublingual cavity, therefore another means of feedback may be necessary. The present invention provides a solution to meet this need.

A dispensing device of the invention may be manufactured in an array of colors that correlate to the array of unit doses to allow for easy identification of drug dose. The device may have other visual, audible, or tactile identifiers to communicate the dosage contained therein.

The dispensing device of the invention affords mechanical protection for the dosage forms contained therein, preventing breakage, chipping, hydration etc., thereby allowing for dispensing of the undamaged dosage forms contained therein. This is of particular importance for small fragile and friable dosage forms. The dispensing device can place an anisotropic or non-homogeneous dosage form under the tongue in a proper or predetermined orientation and in a repeatable fashion.

The dispensing device of the invention finds utility in the dispensing of one or more medications, and in some embodiments provides a plurality of dispensing devices which comprise more than one drug, drug dosage, drug form, etc. In a similar fashion the dispensing device may contain a plurality of dosage forms, in a plurality of cartridges, dispensed by means of multiple mechanisms and delivery channels, etc.

The dispensing device of the invention includes an architecture that allows refilling of the drug dosage form by an approved or authorized user (such as a doctor, nurse, pharmacist or other medical personnel), while denying access to unapproved individuals.

In other embodiments, the dispensing device of the invention includes a disposable tip that contacts the patient's body or mouth, so that the device may be used with multiple patients without the risk of cross contamination.

In another embodiment, the dispensing device of the invention includes a microprocessor (CPU) in communication with a memory means and a display means that enables the device to monitor and control dosing, dose frequency and schedule, and access to the doses and to store programmed and historical information.

In yet another embodiment, the dispensing device is adapted to have the ability to track and communicate the total number of doses remaining in the device to allow anticipation and scheduling of refilling. The dispensing device also may include the ability to record and track drug usage and communicate this, optionally via wireless protocols or by electronic docking, to a healthcare provider to monitor the patient's drug use.

In some embodiments, the dispensing device may be remotely programmed to allow physician oversight and care management. It may include a radio frequency identification (RFID) system, WiFi communication, or other remote operation system that provides a means of communication and control of the device to allow remote monitoring of error codes, dosing histories, patient use histories, remaining doses, battery levels, etc. Such a system may include a unique key for each device that must be proximal to the device for operation, so as to prevent accidental or intentional tampering, abuse, or access to the drug by an unauthorized individual. Such a remote operation system may also provide a unique key located at the patient's bedside, possibly in a stand or dock, or attached to the patient or his or her clothes, possibly on a bracelet, necklace, adhesive patch, or clip, to avoid accidental or intentional swapping of devices between patients or other accidental or intentional diversion.

In embodiments where a dispensing device of the invention is used to dispense a controlled substance such as an opioid, the dispensing device may be designed in such a way as to provide containment of an opioid antagonist in a configuration that prevents intentional diversion. The dispensing device may be equipped with a small liquid opiate antagonist reservoir that is held at slight pressure, and biased to dump the antagonist into the dosage form cartridge. The powered up system actively prevents the antagonist reservoir from flooding the cartridge by means of a valve or other controllable conduit. In the event of a power failure, major physical damage, or malicious tampering, the antagonist reservoir will dispense the opiate antagonist into the cartridge, rendering the dosage forms unsuitable for use. In this embodiment, the dispensing device provides, for example, in a liquid form, in a separate reservoir that will mix with the drug formulation in the event of a power or system failure, device damage or tampering.

In some embodiments, a spoiling agent is used in place of the antagonist. If the dispensing device is forced open, the spoiling agent will contact and contaminate the drug formulation, making it unsuitable for any non-approved use.

To protect the drug dosage forms from exposure to moisture either from humidity, saliva ingress, or accidental exposure to other water based liquids, the dispensing device and the container or cartridge which houses the dosage form within the device may contain a desiccant. A mechanism to prevent saliva ingress includes inclusion of a desiccant, seals, absorbents, adsorbents wipers, and sensors. A desiccant is a sorbant, in the form of a solid, liquid, or gel that has an affinity for water, and absorbs or adsorbs moisture from the surrounding, thus controlling the moisture in the immediate environment. Any commercial desiccant which typically, take the form of pellets, canisters, packets, capsules, powders, solid materials, papers, boards, tablets, adhesive patches, and films, and can be formed for specific applications, including injection moldable plastics find application in practicing the present invention. There are many types of solid desiccants, including silica gel (sodium silicate, which is a solid, not a gel), alumino-silicate, activated alumina, zeolite, molecular sieves, montmorillonite clay, calcium oxide and calcium sulfate, any of which may be used in practicing the present invention. Different desiccants will have different affinities to moisture or other substances, as well as different capacities, and rates of absorption or adsorption. Also, different types of desiccants will come to equilibrium at different relative humidities in their immediate surroundings. As a means for protecting the dosage forms and the internal portions of a dispensing device of the invention from moisture, one or more desiccants may be employed at the dispensing tip, in or adjacent to the dosage form, e.g., tablet, delivery pathway, in or adjacent to the dosage form, tablet container or cartridge, in or adjacent to other components of the dispensing device, formed as an injection molded component of the dispensing device, or in any other location within or without the device.

Disposable And Reusable Drug Dispensing Devices of the Invention

When the desired use of the dispensing device of the invention has been completed, and the dispensing device is no longer needed, it may be either fully disposable, partially disposable and partially reusable, or it may be fully reusable. In one exemplary application, the dispensing device may be used to place a sublingual tablet under the tongue of a patient, and then afford a means of locking the patient out from self-administering another sublingual tablet until a safe lockout time has elapsed between dosing, a means for recording the dosing history, and a means for communicating this history to a user, a computer, another electronic device, or a network.

Because many of the components of the dispensing device of the invention are of high value, and the dispensing end may pose a contagious disease hazard, it may be advantageous to dispose of the dispensing end and reuse the end containing the microprocessor, the memory means, battery, etc. A reusable dispensing device dispenser would require a replenishable power source, such as a rechargeable battery, replaceable battery, refillable fuel cell, or other means of replenishing the system power. The dispensing device may consist of any combination of the following: fully disposable or reusable tip portion, fully disposable or reusable cartridge portion, fully disposable or reusable head portion, fully disposable or reusable head and tip combination, a fixed or portable dock for access and data transfer, a recharge station, a diagnostic station, and a keyed assembly and disassembly station.

In one exemplary embodiment the dispensing device for inpatient (hospital, clinic, etc.) use consists of a disposable tip portion, a disposable drug cartridge portion, and a reusable head portion. The disposable tip portion would contain the delivery tip, a dispensing mechanism, a means to connect and lock to a reusable head, and means to prevent saliva from entering beyond the tip. The disposable drug cartridge would contain a plurality of drug dosage forms, a means for being inserted into a reusable head or a disposable tip, and a means for ordering and containing the dosage forms. The reusable head would contain a microprocessor, a memory means, a power supply such as a battery, a user interface including buttons, a keypad, a display, and LED lights, a means to be recharged between uses and a means for allowing a disposable cartridge to be inserted into the head, a means for attaching and locking to a disposable tip. During setup when an authorized user, e.g., a nurse, is preparing the dispensing device for use by a patient, the nurse would open a new disposable tip from a package, would obtain a new drug filled cartridge from the hospital drug dispensing system, and would obtain a recharged reusable head from a recharging station. The nurse would insert the drug cartridge into the reusable head or disposable tip, then would assemble and lock the disposable tip to the reusable head, thus enclosing the disposable drug cartridge inside the assembled device. The nurse would then show the patient how to use the device and give the device to the patient for self dosing. During disassembly, when the patient had completed his therapy with the dispensing device, the nurse would unlock the reusable head from the disposable body, revealing the drug cartridge (container) within. The nurse would dispose of the drug cartridge and any remaining drug in accordance with hospital protocols, dispose of the disposable tip in a sharps or biohazard container, and would wipe down the reusable head with an antiseptic wipe, then place the head on a recharging station for recharging the battery and future reuse.

The present invention provides exemplary dispensing devices with a singulator dispensing mechanisms including a reusable single dose applicator. The singulator dispensing mechanisms may include the following; a reusable single dose applicator; a foil blister; rotating stations; a disk with ejectors; a ribbon peeler; a ribbon picker; disk singulators; a flexible disk; an arc or helical type single dose applicator; a pushrod stack ejector; and a rotating stack ejector.

The ability of the dispensing device to recognize a specific cartridge may include mechanical, optical (e.g. bar code), electronic (e.g. microchip), magnetic, radio frequency, chemical, or other means of detecting and identifying the cartridge. In one exemplary embodiment of the invention, the cartridge may contain a physical keying detail on the cartridge that is physically detected by a sensor or switch or a series of sensors or switches in the dispensing device. When the cartridge is loaded into the dispensing device, the sensor or switch array can read a mechanical key and identify the cartridge and its contents and/or other information.

In another exemplary embodiment, the cartridge is manufactured with a unique electronic microchip and the dispensing device is equipped with a microchip reader, such that upon loading of the cartridge into the dispensing device the dispensing device reads the information on the microchip identifying the cartridge and its contents and/or other information.

In some embodiments, the cartridge may be modified such that upon a successful or unsuccessful loading attempt into a dispensing device, the dispensing device passes information to the cartridge that it has been loaded or a loading attempt was made. Such a system may include a cartridge with a physical, electronic, optical, magnetic, chemical, or other means of recording information from the dispensing device to the cartridge.

Once the dispensing device has identified the cartridge, or attempted to identify the cartridge, the dispensing device may alter its functionality or cease its functionality based on this information. For example, if the device detects and identifies a cartridge that contains a sublingual opioid dosage form, of a specific strength and duration of action for the treatment of post operative pain, the dispensing device may institute a specific lockout protocol between doses, a specific patient identification protocol, a dosage history recording protocol, and it may alter its user interface appropriately, among other things.

Furthermore, an identification or keying feature on a cartridge may be modified in the event of drug access inside or outside of the dispensing device such that the dispensing device may identify that the cartridge has been opened prior to loading into the dispensing device. In this fashion the dispensing device may detect if a cartridge that is being loaded has been tampered with or previously used.

Functional Aspects of the Drug Dispensing Device of the Invention

Figure 8A:
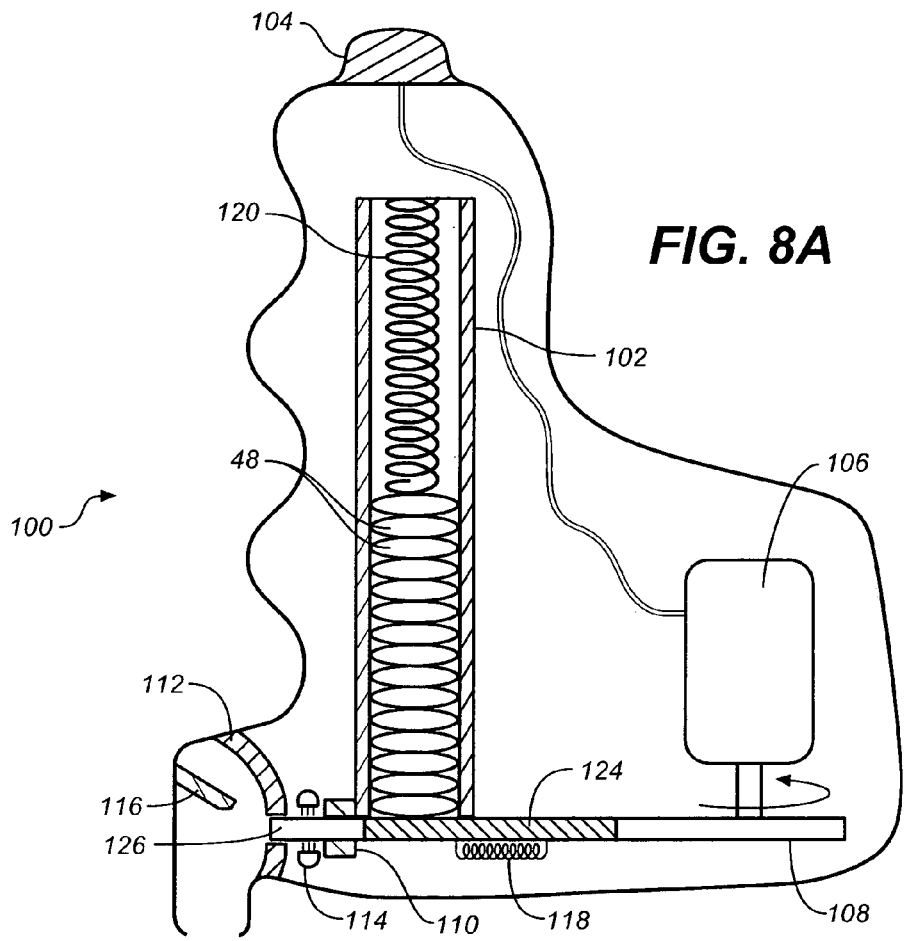
FIG. 8A is a schematic depiction of an exemplary dispensing mechanism for a dispensing device for delivering drug dosage forms, wherein a column type dispensing mechanism at a rest position is illustrated. The dispensing mechanism comprises one or more of a cartridge assembly, an activation button, a motor, a cam, a desiccant agent, seals, a delivery sensor, a spring clip, and a spring.
Figure 8B:
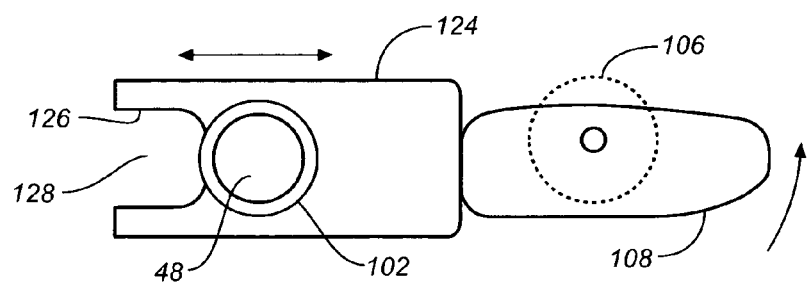
FIG. 8B is a schematic depiction of the dispensing device of FIG. 8A wherein the positions of the dispensing mechanism, motor and cam are at a rest position.

FIG. 8A is a schematic depiction of an exemplary dispensing mechanism for a dispensing device 100 for delivering small-volume oral transmucosal drug dosage forms, wherein a column type dispensing mechanism at a rest position. The dispensing mechanism includes one or more cartridge assembly 102, an activation button 104, a motor 106, a cam 108, desiccant 110, one or more seals 112, a delivery sensor 114, a spring clip 116, and a spring 118. The dispensing device 100 of the invention provides for dispensing of dosage forms based on a stack or plurality of dosage forms 48 contained in the tubular cartridge or magazine 102, with a spring 120 at one end wherein a loading force is applied to the stack of dosage forms. FIG. 8B is a schematic depiction of the dispensing device of FIG. 8A wherein the positions of the dispensing mechanism, motor and cam are at a rest position. The assemblies 102 and dosage form stack 48 rest upon the slider 124 which is perpendicularly movable to the axis of the dosage form stack 48. The slider 124 is a thin blade, with a thickness equal to or less than that of a single dosage form, on axis with the dosage form stack. The slider 124 slides between the end of the dosage form cartridge 102 and a solid face such that the spring 120 pushes the stack so as to place the first dosage 48 against the solid face on the other side of the slider 124. The slider 124 includes a receiving portion 128 sized to accept the first dosage 48 opposite the cam. Exemplary cartridge dispensing mechanisms include column type, ribbon/tape type, disc type, helical type, barrel type, index/spring-load type, hopper type, conveyor type, continuous tablets type, shrink wrap type, snap-out type, track type, barrel lock type, adhesive tape, pocket tape type, a single dose applicator, and foil on stack type.

A dispensing device of the present invention may dispense a dosage form by manual actuation of a button, lever, slider, wheel, or other actuator or by a mechanism selected from the group consisting of mechanical actuation, electro-mechanical actuation, spring loaded actuation, pneumatic actuation, hydraulic actuation, magnetic actuation, gravitational force activation, thermal actuation, combustive actuation, phase change expansion or contraction actuation, sonic actuation, and absorbent actuation. The device may dispense a dosage form by means of a microprocessor controlled actuator.

The dispensing mechanism for dispensing a drug dosage form may comprise a mechanical or electromechanical means for dispensing the drug dosage form.

Figure 23A:
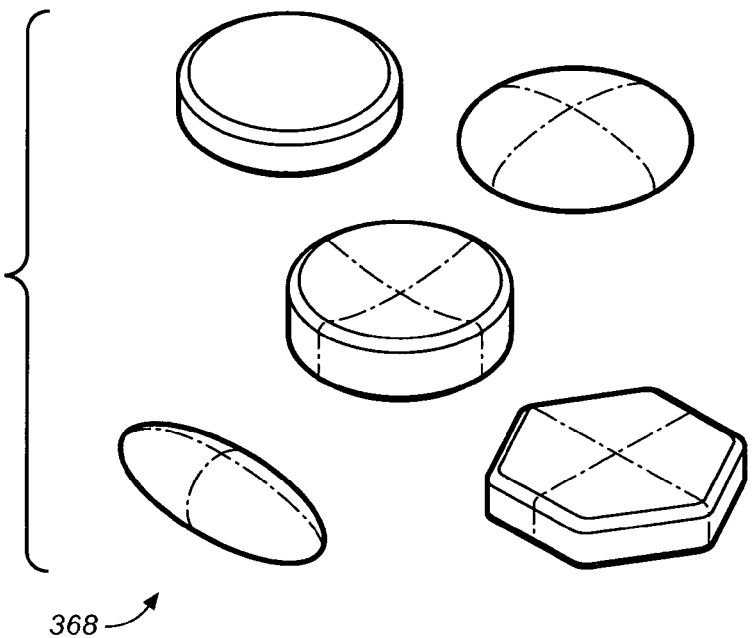
FIGS. 23A and 23B provide depictions of exemplary drug dosage form shapes.
Figure 23B:
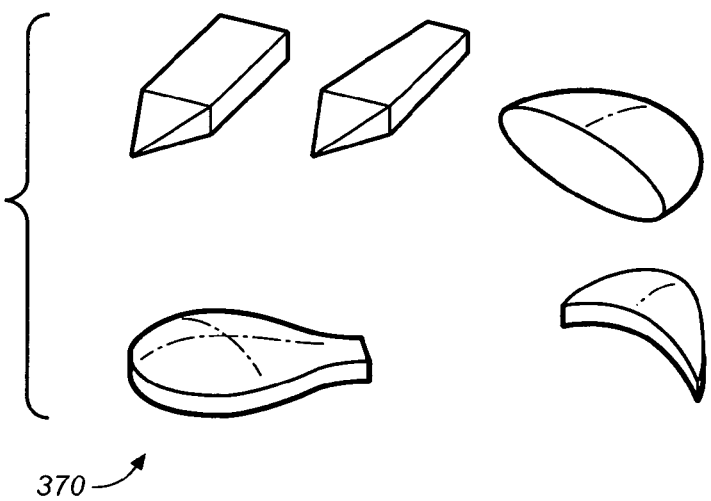

The drug dosage dispenser of the invention may contain a means of dispensing a drug dosage form that consists of a push rod, a track or passage connecting a drug dosage cartridge with an outlet or exit from the dispenser, and one or more seals within the dispenser or at the exit of the dispenser, or any combination of these features. FIGS. 4A-4D show an exemplary dispensing device with a push rod design, which serves to push a drug dosage form, for example a tablet through a delivery channel that is designed to delivering the drug dosage form. The push rod and drug dosage form may contain features or forms that allow for optimal handling and delivery of the drug dosage form, including interfacing with the delivery track or passage and the seal or seals through which the drug dosage form is delivered. FIGS. 4A-4D are schematic depictions of an exemplary dispensing device for delivering drug dosage forms to the oral mucosa, wherein a means for minimizing saliva influx into the dispensing device during the administration of the dosage forms to the patient is shown. FIGS. 5 and 6 are schematic depictions of an exemplary geometry for a dispensing tip that prevents contact of one or more seals with the moist or wet surface. FIGS. 23A and 23B provide depictions of exemplary drug shapes. FIGS. 19A-F are schematic depictions of geometries of another exemplary slit type septum seals designed to maintain a uniform seal around a drug dosage form and a pushrod during delivery of the drug dosage form.

Figure 8C:
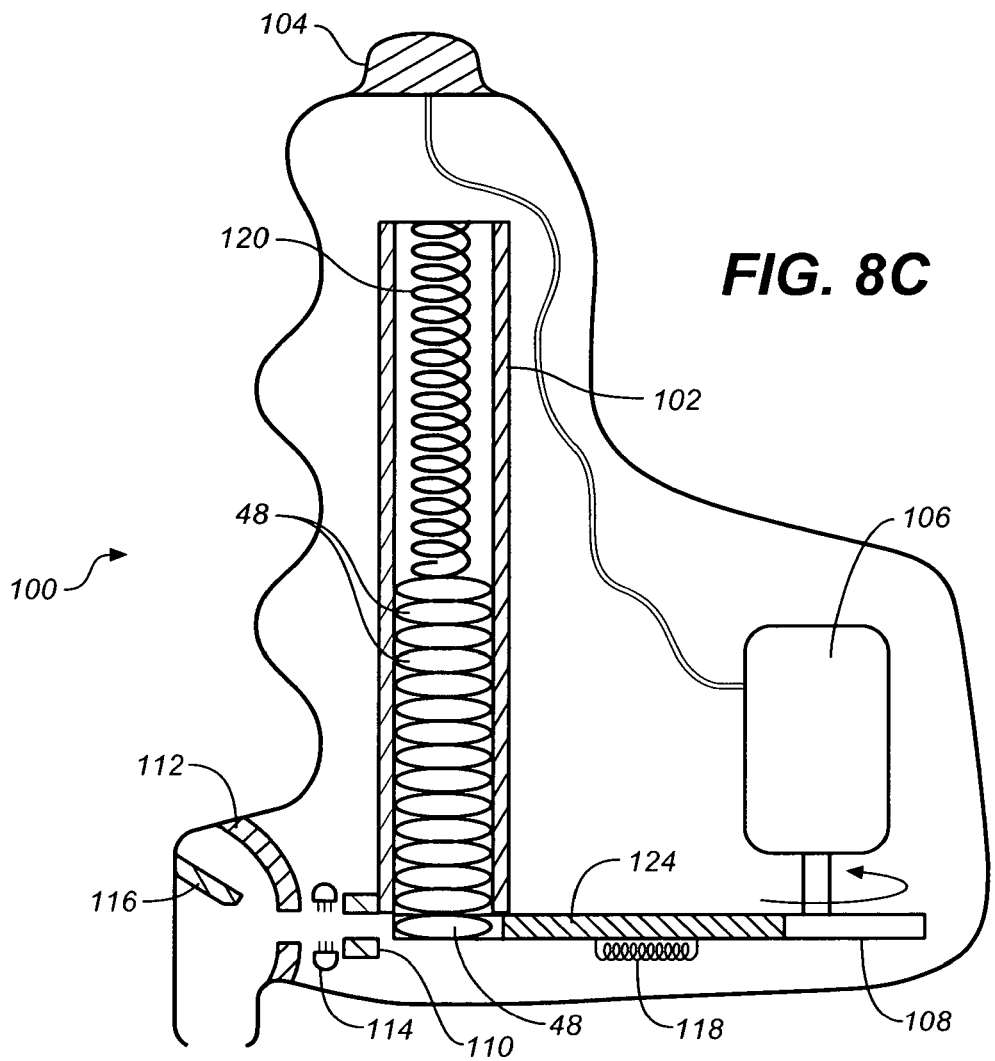
FIGS. 8C and 8D are a schematic depiction of the dispensing device of FIG. 8A wherein the positions of the dispensing mechanism, motor and cam are at a retrieval position.
Figure 8D:
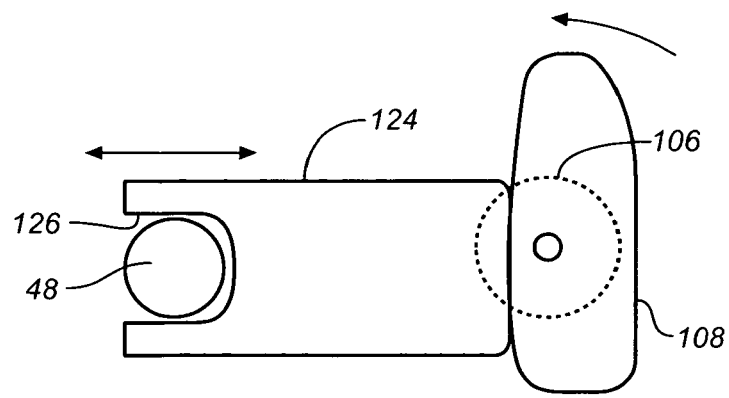

FIGS. 8C and 8D are a schematic depiction of the dispensing device 100 with the dispensing mechanism at a retrieval position. In the retrieval position, the motor 106 turns the cam 108, retracting the slider 124, and allowing placement of the first dosage 48 in the receiving portion 128. FIG. 8C shows the slider 124 retracted by means of a rotation of the cam 108, and displacement by the spring 118. In this position a dosage form 48 is pushed by the spring 120 into the receiving cup 126 portion of the slider 124.

Figure 8E:
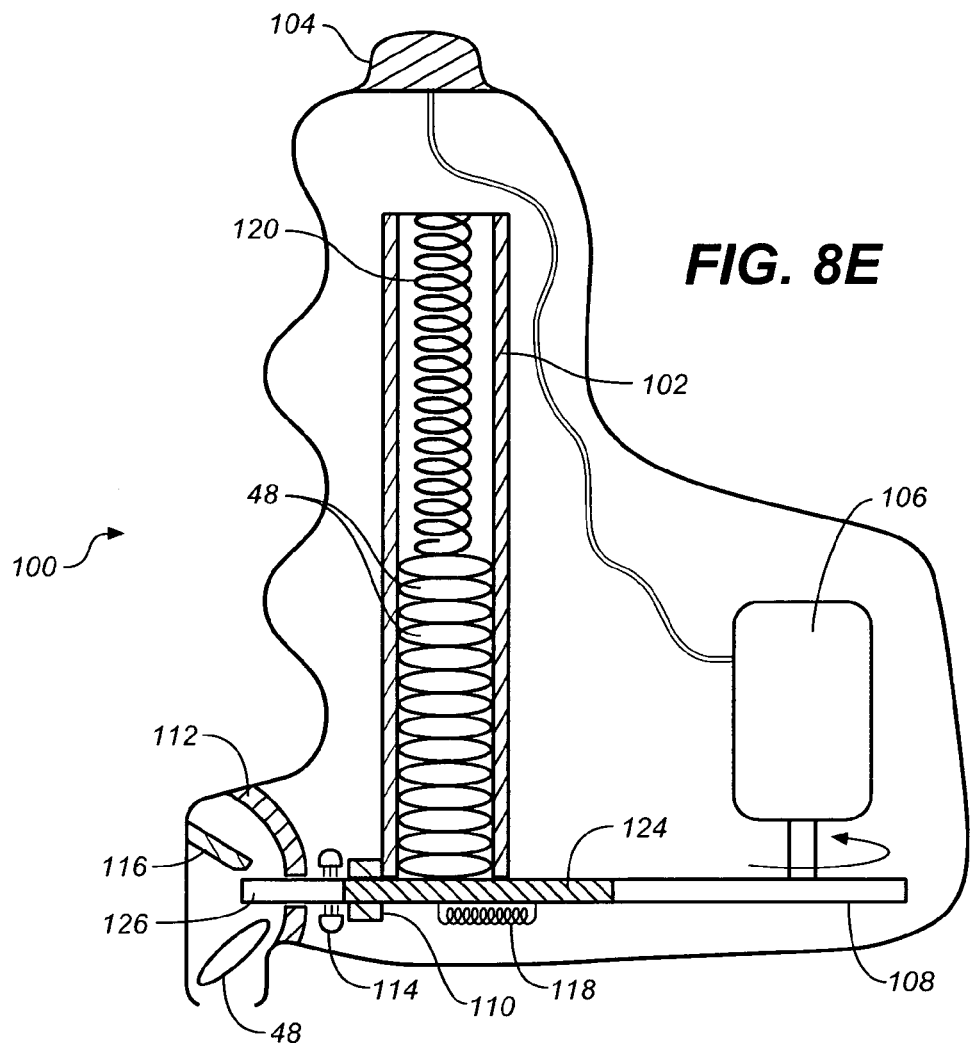
FIGS. 8E and 8F are a schematic depiction of the dispensing device of FIG. 8A wherein the positions of the dispensing mechanism, motor and cam are at a dispensing position.
Figure 8F:
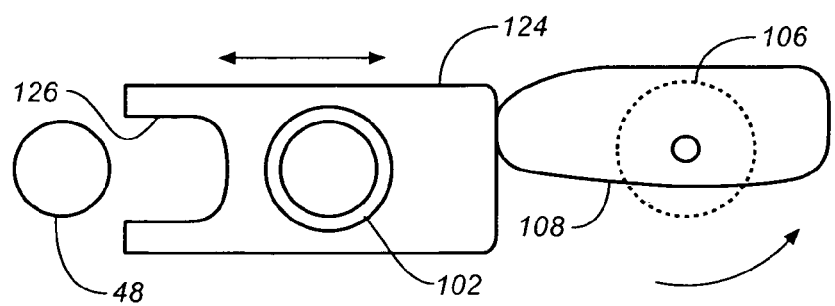

FIGS. 8E and 8F are a schematic depiction of the dispensing device 100 with the dispensing mechanism at a dispensing position for delivering drug dosage forms. In the dispensing position, the motor 106 turns the cam 108, extending the slider 124 with the first dosage form 48, and allowing dispensing of the first dosage 48. FIG. 8E shows the cam 108 rotated so as to drive the slider 124 forward and dispense a dosage form 48 past the sensor 114 and through the seal 112. The slider 124 continues to move until such a point as the dosage form that has been removed from the stack is free to fall from the cup 126 or is forcibly pushed from the cup 126 by the spring clip 116 and dispensed.

Figure 8G:
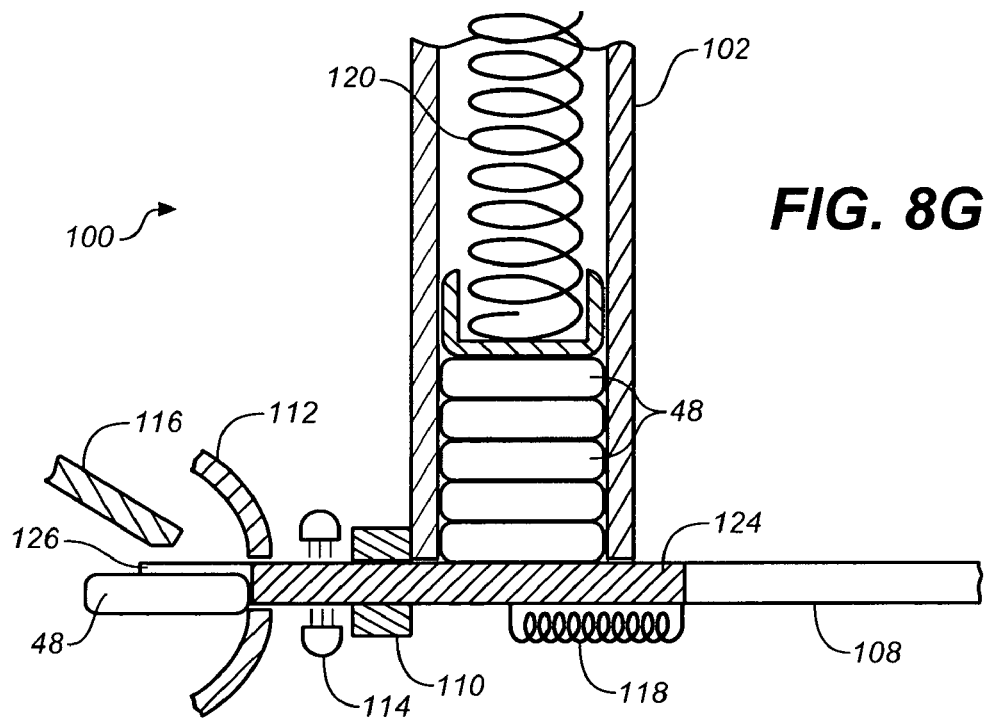
FIGS. 8G and 8H are depictions of the optical sensing mechanism for detecting delivery of drug dosage forms of the dispensing device. The dispensing mechanism comprises one or more cartridge assembly, cam, desiccant, seals, delivery sensor, and a spring clip.
Figure 8H:
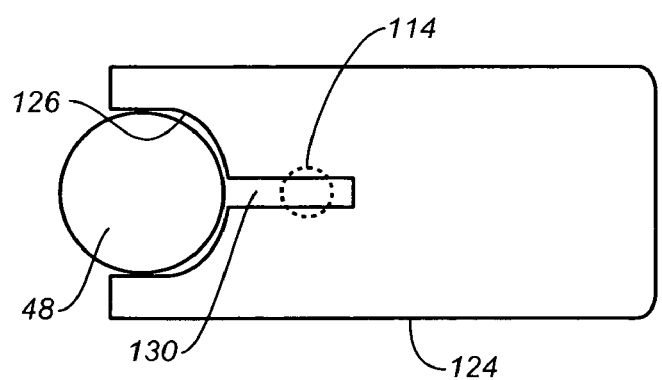

FIGS. 8G and 8H are depictions of the optical sensing mechanism for detecting delivery of drug dosage forms of the dispensing device 100, wherein the position of a slider 124 and a drug dosage form 48 are illustrated. In this embodiment, the slider 124 includes a slot 130 for the delivery sensors 114, so that the delivery sensors 114 will detect the passing and delivery of drug dosage forms 48. When the slider 124 pushes a dosage form 48 past the optical sensors 114, the optical sensors 114 record an interrupted signal, indicating that a dosage form is present in the cup of the slider 124. If a dosage form 48 were not present in the cup of the slider 124 then the optical sensors 114 would not record an interrupted signal, indicating that a dosage form 48 was not present.

In yet another embodiment of the invention, a long tape or array of dosage forms sealed between a flexible blister layer and a foil or otherwise breakable layer is provided. A pusher is positioned above a dosage form, and upon actuation pushes against the blister, forcing the dosage form through the foil or breakable layer, dispensing the dosage form.

Figure 9C:
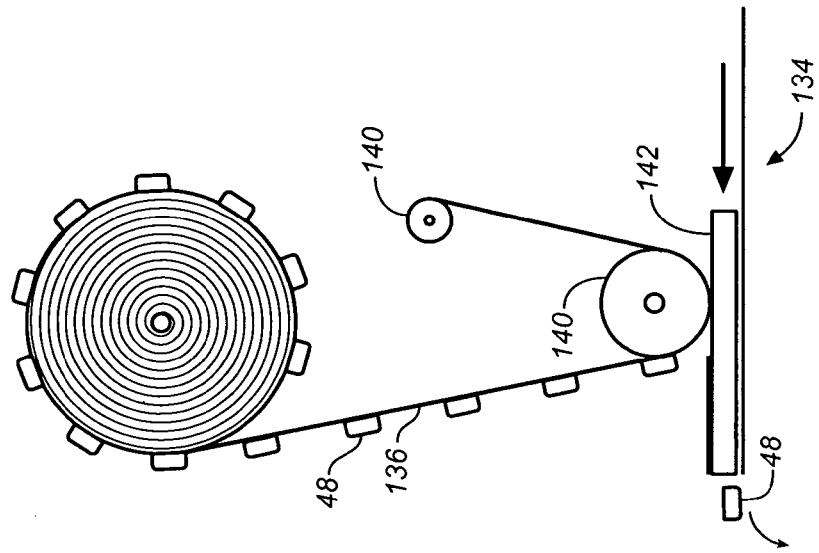
FIG. 9C depicts the dispensing mechanism of FIG. 9A at a dispensing position.
Figure 9B:
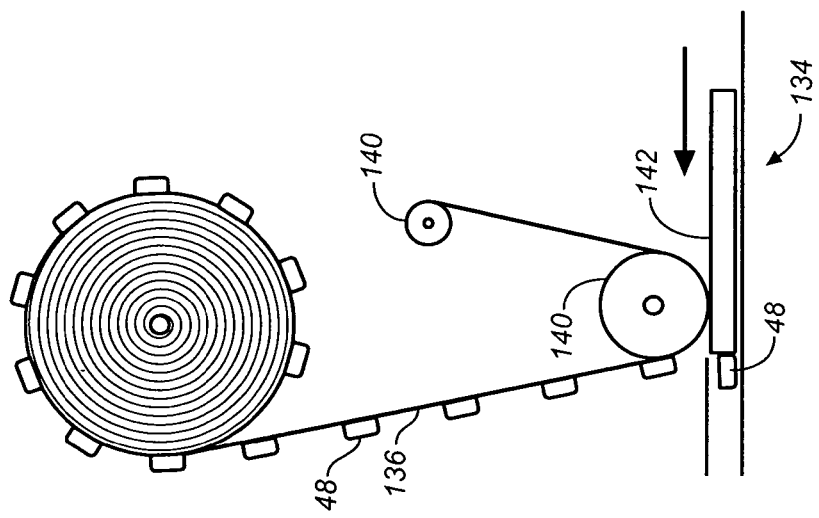
FIG. 9B depicts the dispensing mechanism of FIG. 9A at a retrieval position.
Figure 9A:
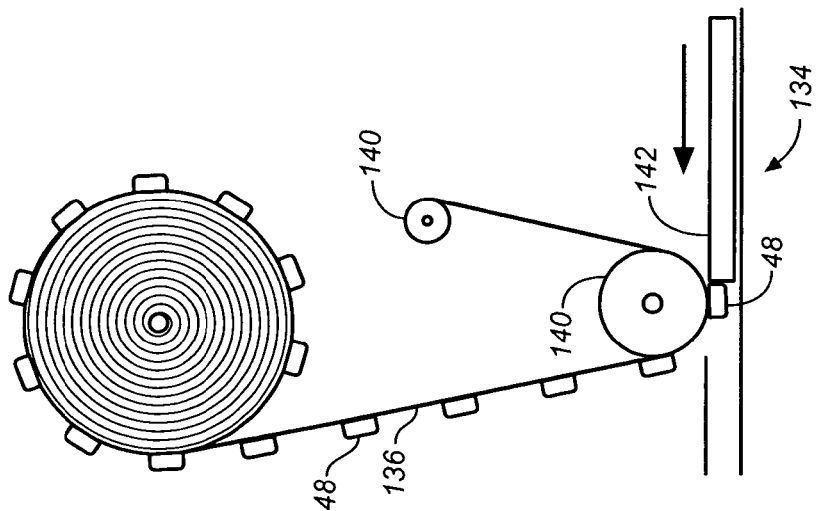
FIG. 9A depicts an additional embodiment of a dispensing device of the invention dispensing mechanism, wherein a ribbon type dispensing mechanism at a rest position is illustrated.

FIGS. 9A, 9B and 9C depict an additional embodiment of the dispensing devices of the invention, wherein a ribbon type dispensing mechanism 134 is illustrated. FIG. 9A depicts the dispensing mechanism at the rest position, FIG. 9B depicts the dispensing mechanism at retrieval position, and 9C depicts the dispensing mechanism at dispensing position. The mechanism includes a long tape or array of dosage forms adhered to one face with an adhesive. To dispense a dosage form 48, the tape 136 is rolled rollers 140 such that the surface with the dosage forms 48 adhered to it forms a convex shape, causing the dosage forms 48 to peel off of the adhesive. In the embodiment shown, a peeler blade 142 may be incorporated to assist in removing the dosage form 48 from the adhesive.

Figure 10:
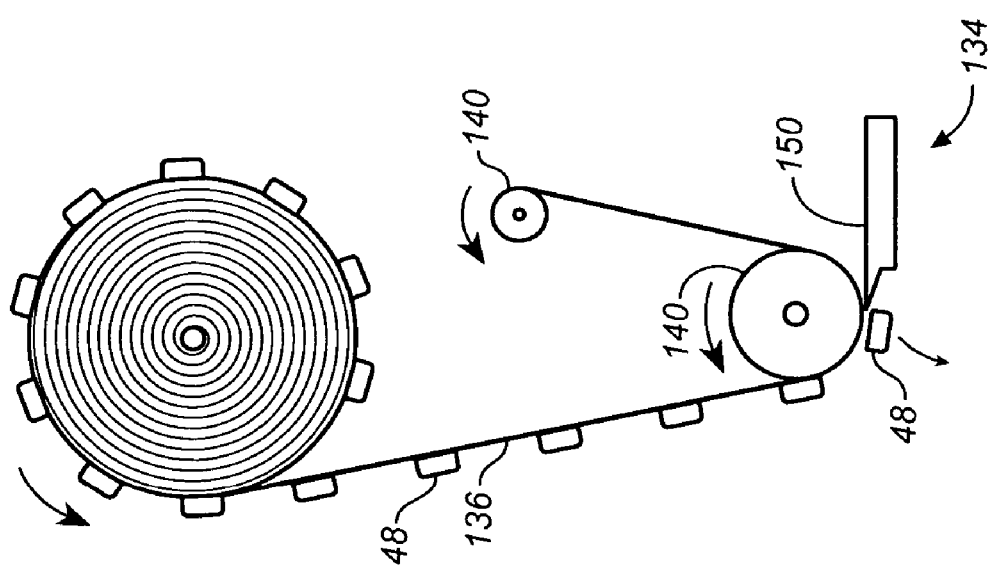
FIG. 10 depicts an additional embodiment of a dispensing mechanism of a dispensing device of the invention, wherein a ribbon type dispensing mechanism using a different type of a pushrod at dispensing position is illustrated.

FIG. 10 depicts an additional embodiment of the dispensing mechanism 134, wherein a different shape of a peeler blade 150 is shown. In another embodiment, gas pressure may be used to assist in removing the dosage form 48 or force a single dosage form 48 from the dispensing mechanism 134.

To dispense a dosage form 48 the tape 136 is rolled on a roller 140 such that the surface with the dosage forms adhered to it forms a convex shape, causing the dosage forms 48 to peel off of the adhesive. A peeler blade may be incorporated to assist in removing the dosage form from the adhesive tape 136. A peeler blade 150 may be incorporated to assist in removing the dosage form 48 from the adhesive FIGS. 11A and 11B depict yet another embodiment of the dispensing devices of the invention, wherein a disc type dispensing mechanism 152 utilizing a disk cartridge 146 is shown at a rest position (FIG. 11A) and at a dispensing position (FIG. 11B). The dispensing mechanism 152 includes a lever handle 150 with teeth that engage a gear 151, a rack/pusher 153, and a channel 154 in a housing, and a spring 156. The channel 154 provides space for the rack/pusher 153 to freely move within the channel 154. In FIG. 11A, the rack/pusher 153 is ready to push a dosage form 48. As the lever handle 150 is pushed, the spring 156 is compressed and the gear 151 rotates and the rack/pusher 153 engages the drug dosage form 48. The drug dosage form 48 is pushed within the channel 154. FIG. 11B shows the dosage form 48 being dispensed from the end of the channel 154 and into a subject, such as human. Then the steps are repeated for successive dispensing of the dosage form 48.

The dispensing mechanism 152 consists of the following: a dispensing trigger 150, a return spring 156, a gearing reduction 151, a pusher 153, a disk cartridge 146, a circular cam/ratchet 145, a dosage form 48, a housing 144, and a seal 143. When the trigger 150 is depressed, driving the gearing reduction 151, the pusher 153 is driven through a disk cartridge 146 in such a manner that the pusher 153 drives a single dosage 48 from the disk cartridge 146. The disk cartridge 146 is fabricated with individual dosage compartments arrayed around the perimeter of the disk, and sealed with foil on both faces so as to individually seal and package the dosage forms 48. As the pusher 153 is driven through the disk cartridge 146, it breaks the foil seals on each face, pushing the dosage form 48 out of the disk cartridge 146, through a seal 143, and delivering it from the dispenser housing 144.

FIG. 11B depicts an additional means of dispensing drug dosage forms, wherein a disc type dispensing mechanism in a dispensing position 154 is illustrated. This figure depicts the pusher 153 in a dispense position after it has pushed a dosage form 48 out of the disk cartridge 146 and through the seal 143. After the dosage form is delivered from the housing 144, the return spring 156 returns the mechanism and a circular cam/ratchet 145 indexes the disk cartridge 146 by rotating it so that the next dosage form 48 is in position for the next delivery.

A disk delivery and indexing mechanism may be employed to deliver a drug dosage form from a dispenser of the invention. A disk delivery mechanism may be manually or electromechanically actuated, and my use lead screws, gears, mechanisms, linkages, rotary drives or any other means of advancing that enables the delivery mechanism to deliver a dosage form. The indexing ratchet may be achieved by means of a circular cam, an escapement, a lead screw, a gear train, a linkage, a stepper motor or other motor drive or any other means of indexing a disk.

A dispensing device may be pre-filled with a number of drug dosage forms in such a manner that the device is purchased and stored with the dosages in the device, or it may be filled on site at a pharmacy, or it may be filled on the hospital floor by a nurse or other healthcare professional. The dosage forms may be packaged as a group of tablets in a bottle, vial, or other container, or they may be packaged in a controlled orientation in a drug cartridge. The drug cartridge may contain the doses in any configuration, including a stack, a row, a circular disk, a circular-arc disk, a strip, ribbon, tape, helix, or an array or combination of any of the above, for example a multitude of stacks of doses arranged in a geometric array. The invention further provides additional methods of dispensing drug dosage forms which may include combinations of these or other mechanisms. For example, a system may contain a shuttle to remove a dosage form from a stack, and a pusher to forcibly push the dosage form out of the system.

FIGS. 12A-12C depict an exemplary pushrod 158 designed for dispensing a drug dosage form 48. The pushrod may be made from any suitable material, for example, stainless steel.

Figure 13:
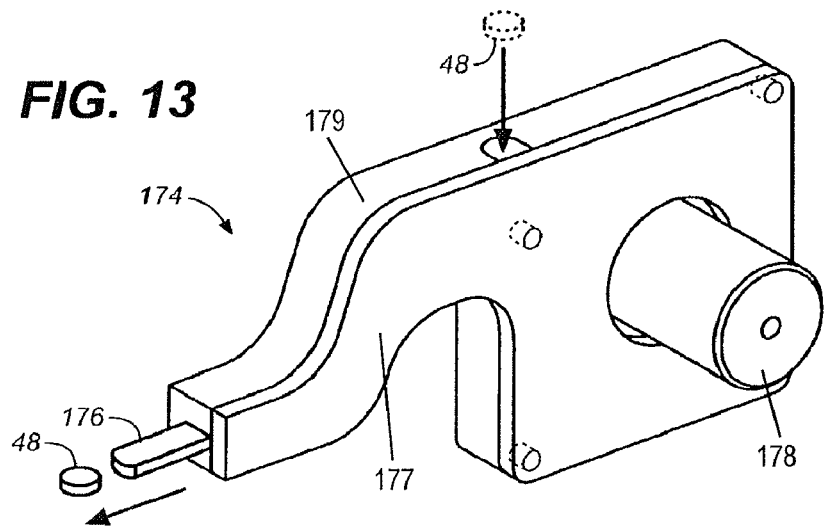
FIGS. 13 and 14 depict additional exemplary pushrod dispensing devices of the invention for dispensing a drug dosage form, wherein the pushrods are designed to be flexible and to afford different geometry.
Figure 14:
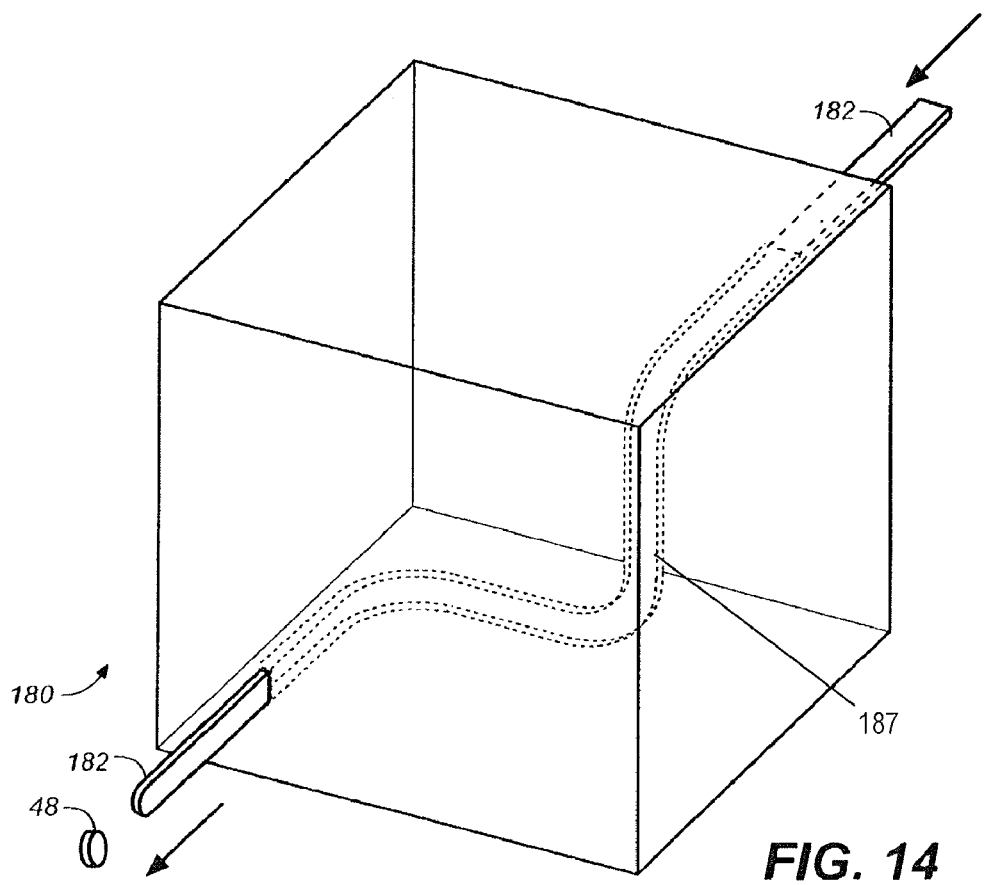

FIGS. 13 and 14 depict other exemplary dispensing mechanisms with pushrods for dispensing drug dosage forms, wherein the pushrods are designed to be flexible. FIG. 13 shows dispensing mechanism 174 for singulating and advancing a drug dosage form 48 through a nonlinear or linear pathway (defined by a housing 179) by means of a flexible shaft 176 attached to an advancing mechanism, such as a rotation hub 178. such that advancing or retracting the flexible shaft within the nonlinear or linear pathway allows for the dispensing of a tablet or other dosage form 48 through the nonlinear pathway. In some embodiments, the pathway defined by the housing 179 includes an "S-shaped" portion 177. FIG. 14 shows dispensing mechanism 180 for singulating and advancing a drug dosage form 48 through a nonlinear pathway 187 or linear pathway by means of a flexible shaft 182 attached to an advancing mechanism, such as a rotation hub, such that advancing or retracting the flexible shaft within the nonlinear or linear pathway allows for the dispensing of a tablet or other dosage form 48 through the nonlinear pathway.

In a related approach, the drug delivery device of the invention comprises a tubular cartridge containing the stack, a spring pushing the stack, a solid face, and a slider or pusher, similar to the embodiment described above. In this embodiment, the slider or pusher lacks a hole, but rather retracts from beneath the dosage form stack such that the spring can push the dosage forms up against the solid face. During actuation the pusher, which has a thickness equal to, larger than, or less than that of a single dosage form, pushes the first dosage form in the stack perpendicular to the cartridge and dispenses it out of the side slot.

In another embodiment of the invention, dosage forms are dispensed by moving a dosage form stack which is mounted with a pusher at one end and an elastomeric diaphragm retaining the opposite end of the dosage form stack. The diaphragm contains an orifice or hole or slot at the location of the first dosage form. Upon actuation, the pusher pushes the stack and a single dosage form emerges from the diaphragm hole, at which point the pusher retracts slightly to allow the elastomeric diaphragm to re-seal and close again. The elastomeric diaphragm may be a seal or wiper type seal.

FIGS. 15A-15F are schematic depictions of exemplary lockout mechanisms. FIG. 15A depicts a pushrod type lockout mechanism 186. When a pushrod 188 is pressed, a solenoid 190 reacts to a signal to move a return lock 192 in a locking position, to prevent a dispensing device from dispensing drug dosage forms 48 during a lockout period. FIG. 15B depicts an actuator type lockout mechanism 196. When a pushrod 200 is pressed in a lockout mechanism 196, a lock 198 moves in response to the pushrod's 200 movement with the help of solenoid 202 to lockout on actuator. FIGS. 15C and 15D depicts a safety button/latch type lockout mechanisms 204 and 214, respectively. In the figures, a latch 206 locks a pushrod 210 in a locked position. A patient pushes the dispenser 212 to reveal button 208 to unlock the latch 206. FIG. 15E depicts a solenoid type I lockout mechanism 216, wherein solenoid moves to lock the device. Another solenoid type lockout mechanism 218 is shown in FIG. 15F. Solenoid 220 moves upon a button 222 being pressed and locks the device.

Figure 16A:
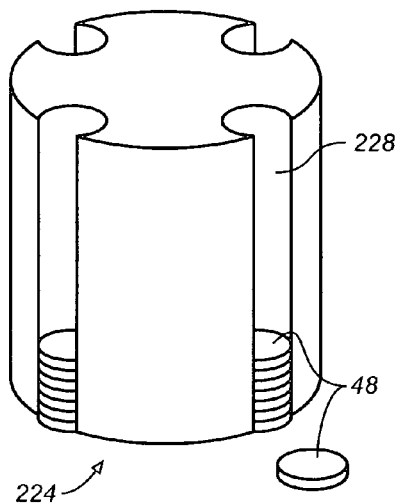
FIGS. 16A-16D provide schematic depictions of exemplary drug cartridges including barrel, index/springload, snap-out, and track type, respectively.
Figure 16B:
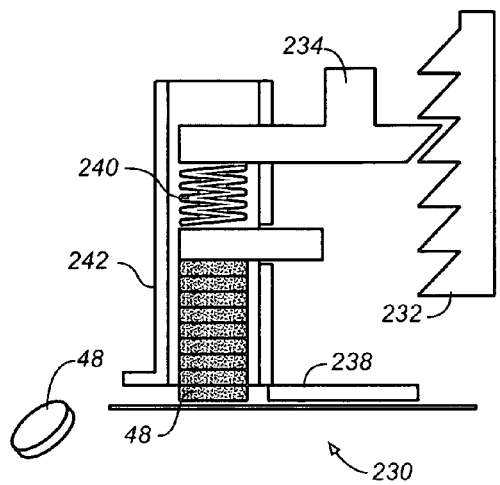
Figure 16C:
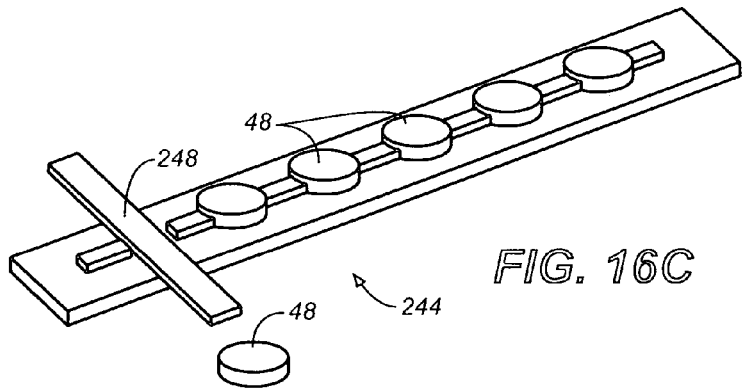
Figure 16D:
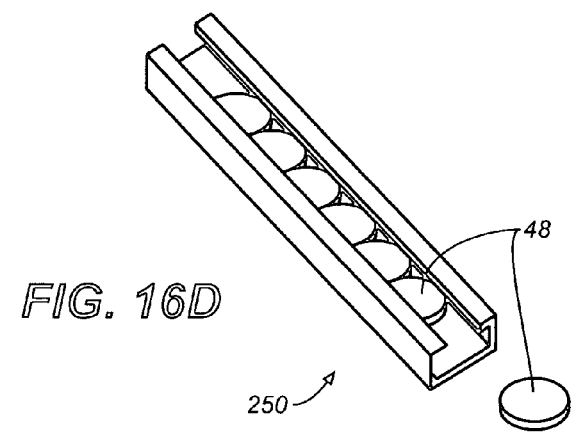

FIGS. 16A-16D provide schematic depictions of exemplary drug cartridges including barrel type cartridge 224, index/springload type cartridge 230, snap-out type cartridge 244, and track type cartridge 250. FIG. 16A depicts a barrel type cartridge 224 which dispenses drug dosage forms 48 stacked in each barrel 228 and rotates upon each actuation. FIG. 16B depicts an index/springload type cartridge 230. When a pusher 234 is pressed upon a rack 232, a spring 240 is used to minimize compression exerted on the drug dosage forms 48 stacked in the cartridge 242 and a pushrod 238 pushes the dosage forms 48 to dispense. FIG. 16C depicts a snap-out type cartridge 244. In the cartridge 244, a stick holding drug dosage forms 48 is moved toward a pushrod 248 and the pushrod 248 pushes the drug dosage form 48 and snaps on the stick when dispensing is completed. FIG. 16D depicts a track type cartridge 250. Drug dosage forms 48 stacked in the track are dispensed.

Figure 17A:
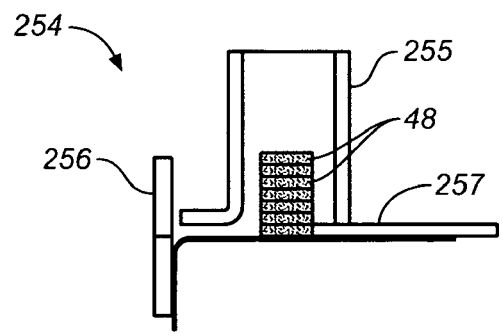
FIGS. 17A and 17B are schematic depictions of dispensing devices of the invention showing a drug dosage form being pushed through a seal by a pushrod, wherein the geometry of the seal is tailored to the shape of the dosage form and pushrod.
Figure 17B:
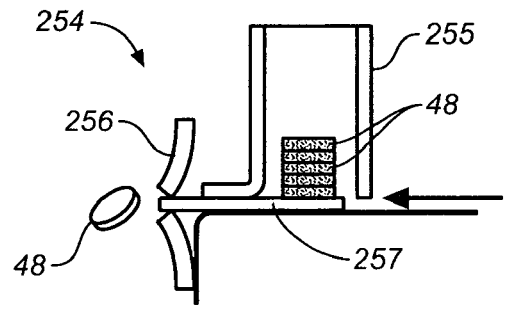

FIGS. 17A and 17B are schematic depictions of a drug dosage form being pushed through a seal by a pushrod, wherein the geometry of the seal is tailored to the shape of the dosage form and pushrod. FIG. 17A depicts a dispenser 254 comprising drug dosage forms 48, a cartridge 255, septum or seal 256, and a pushrod 257, wherein the drug dosage forms are stacked for dispensing. In the dispenser 254 in FIG. 17B 256, drug dosage forms 48 are being pushed through the septum 256 by the pushrod 257, wherein the geometry of the septum 256 is tailored to the shape of the dosage form 48 and the pushrod 257.

Figure 18:
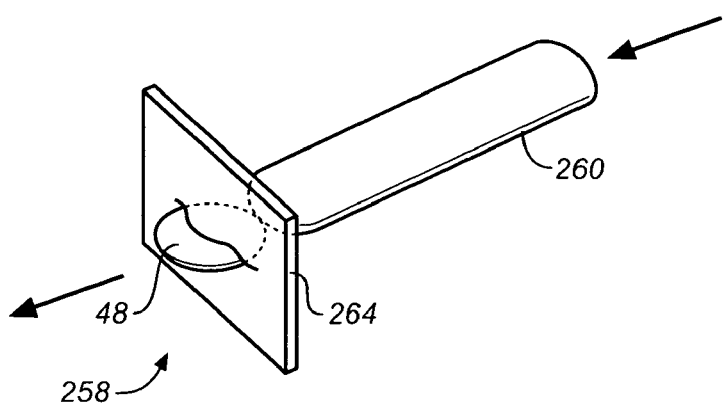
FIG. 18 is a schematic depiction of the geometry of an exemplary pushrod, drug dosage form, and septum-type seal. The exemplary slit type septum seal is designed to maintain a uniform seal around a drug dosage form and a pushrod during delivery.

FIG. 18 is a schematic depiction of geometry 258 of an exemplary pushrod 260, drug dosage forms 48, and septum-type seal 264. The exemplary slit type septum seal 264 is designed to maintain a uniform seal around the drug dosage form 48 and the pushrod 260 during delivery. Additionally, the means for transporting the drug dosage forms through the seals, wipers, doors, absorbents, etc. may include the use of a push rod or shuttle that is specifically designed to limit saliva ingress and manipulate the tablet through the components.

FIGS. 19A-19F are schematic depictions of the geometry 266, 268, 270, 272, 274 and 276 respectively, of other exemplary slit type septum seals designed to maintain a uniform seal around a drug dosage form and a pushrod during delivery of the drug dosage form. The exemplary slit type septum seal is designed to maintain a uniform seal around a drug dosage form and a pushrod during delivery. Additionally, the means for transporting the drug dosage forms through seals, wipers, doors, absorbents, etc. may include the use of a push rod or shuttle that is specifically designed to limit saliva ingress and manipulate the tablet through the components.

The preferred means of actuating a drug delivery device of the invention is a mechanical means such as manual actuation of a button, lever, slider, wheel, or other actuator. However, a drug delivery device of the invention may rely on alternate means of actuating, including mechanical actuation, electromechanical actuation, spring loaded actuation, pneumatic actuation, hydraulic actuation, magnetic actuation, gravitational force activation, thermal actuation, combustive actuation, phase change expansion or contraction actuation, sonic actuation, and absorbent actuation.

The device can use a variety of mechanical or electromechanical methods to expel the dosage form, e.g., into the oral or sublingual space. For example the dosage form can be forcibly expelled by means of a spring, compressed air, or other mechanism once activated.

The present invention provides exemplary architectures including reusable options. The present invention provides exemplary architectures including reusable options. The reusable device may be cleaned, recharged, reloaded, or have its memory cleared after treatment and be used again. The drug dosage dispenser of the invention may contain a plurality of components that are assembled such that one or more components are reusable, to allow for reuse of expensive or high value components and reduce wastep, and one or more components are disposable, to allow easy disposal of dirty or contaminated components, components that pose a contagious disease hazard, or components that contain unused or contaminated drug. In one such exemplary embodiment, a dispenser system, a disposable drug dosage form cartridge would be loaded into a disposable delivery portion of a dispenser. A reusable portion of the dispenser would then be joined to the disposable portion in such a manner as to afford a tamper deterrent lock between the components. The reusable portion of the dispenser would detect the proper assembly of the cartridge and disposable portion of the dispenser, confirming proper assembly and allowing normal use of the dispenser to ensue. Improper or incomplete assembly would result in the reusable portion of the dispenser locking and displaying an error code or indication for error diagnosis.

The assembly of two or more components of the dispenser may contain a locking mechanism to prevent or deter tampering or diversion of the drug within. The locking mechanism may be afforded by means of a solenoid, a motor, a piezoelectric actuator, a pneumatic or hydraulic actuator, a shape-memory actuator, a latch, a pin, a snap, a cam, a slider, a linkage, or any other mechanical or electromechanical means. Furthermore, the locking means may be locked or unlocked by means of a physical key, a combination, an electronic key, a magnetic key, pass code, PIN, encrypted or unencrypted logic signal, a wireless signal, RFID, finger print identification, or other means of mechanical or electromechanical unlocking of a lock.

After use of the dispenser, and upon disassembly, the reusable portion or portions, may be retained for future use, while the disposable portion or portions may be disposed of.

Figure 20A:
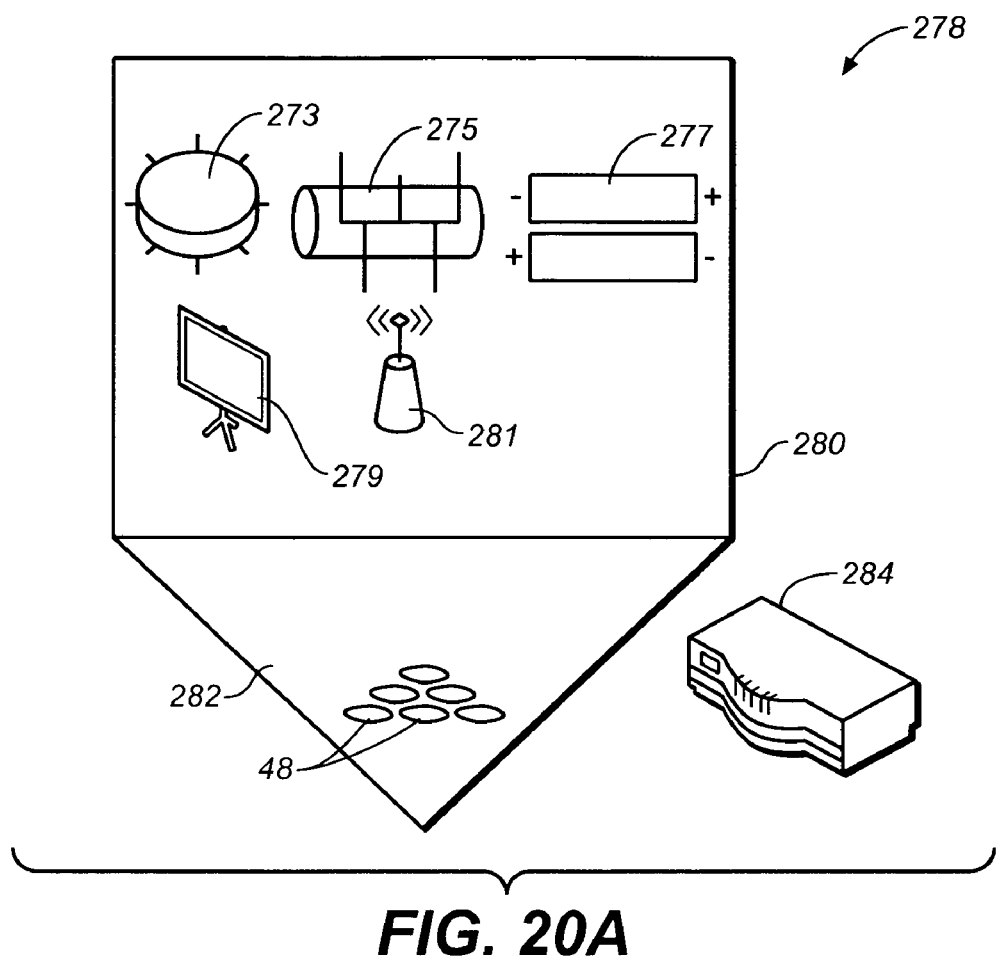
FIG. 20A is a schematic depiction of an exemplary architecture having a reusable head, disposible body, and recharge station.

FIG. 20A is a schematic depiction of an exemplary architecture 278 having a reusable head. The reusable option includes the following: a reusable head 280, a body 282, and a recharge station 284. This embodiment 278 is comprised of the following: a reusable head 280 containing a power supply 277, a microprocessor and printed circuit board (PCB) 275, an actuator 273, a user interface 279, a user identification means 281; a disposable body 282 containing a disposable drug dosage cartridge 48; and a recharging station 284. In this embodiment the reusable head 280 is lockably connected and disconnected from a disposable body 284. After use, the disposable body 282, the drug dosage form, and the cartridge 48 are disposed of, while the reusable head 280 is cleaned and docked in the recharge station 284 to recharge the power supply. The power supply 277 may be a rechargeable or replaceable battery, a fuel cell, or any other means of powering the device. The actuator 273 may be a motor, solenoid, linear actuator, piezo-electric actuator, shape memory actuator, hydraulic or pneumatic actuator or any other means of actuating a mechanism. The user interface 279 may be include a graphical or numeric display, a keypad, buttons, switches, dials, sliders, lights, LED's, LCD's, speakers, microphones, buzzers, or any other means of communication to or from a user. The user identification means 281 may be an RFID tag reader, a Wi-Fi system, a fingerprint reader, a voice recognition system, an image or facial recognition system, a local area network that communicates by way of the human body, a DNA recognition system, a retinal scanner, or any other means of identifying an individual user or patient. The drug dosage cartridge 48 may be a stack, disk, tape, single dose applicator, an may contain a single dose or a plurality of doses. The PCB 275 may include a processor, a memory means, a power regulator, a recharge cycle, a patient identification means, graphic drivers, and any other components or systems to affect the performance of the dispenser device 278. The dispensing mechanism may be contained in the disposable body 282 or in the reusable head 280 or partially in both locations. The recharge station 284 may recharge the power supply, may perform a diagnostic on the reusable head 280, or may serve as an informational dock, either wired or wireless, to communicate between the dispenser device and another device, computer or network.

Figure 20B:
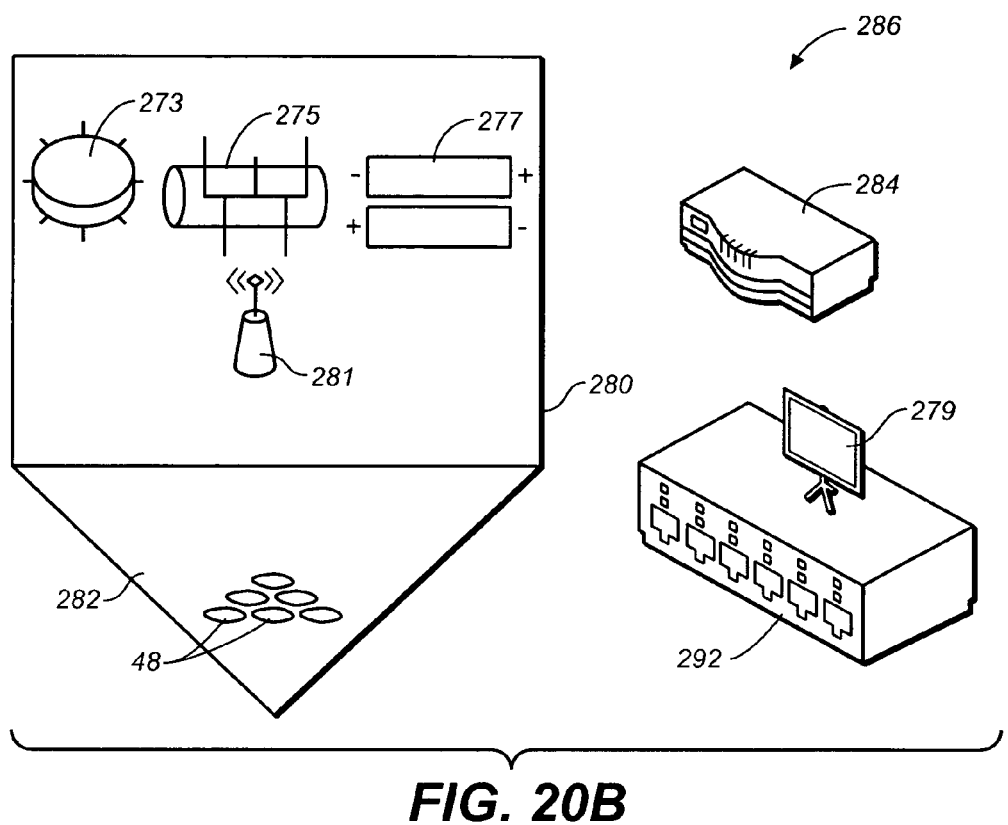
FIG. 20B is a schematic depiction of an exemplary architecture having a reusable head, a disposible body, a docking station, and a docking station.

FIG. 20B is a schematic depiction of an exemplary architecture 286 having a reusable head 280 containing an actuator 273, a PCB 275, a power supply 277, and a user identification means 281, a disposable body 290, containing a drug dosage cartridge and drug dosage forms 48, a docking station 292 containing a communication means and user interface 279, and a recharge station 284. The reusable option includes the following: the reusable head 280, a disposable body 282, docking station 284, and the docking station 292.

Figure 20C:
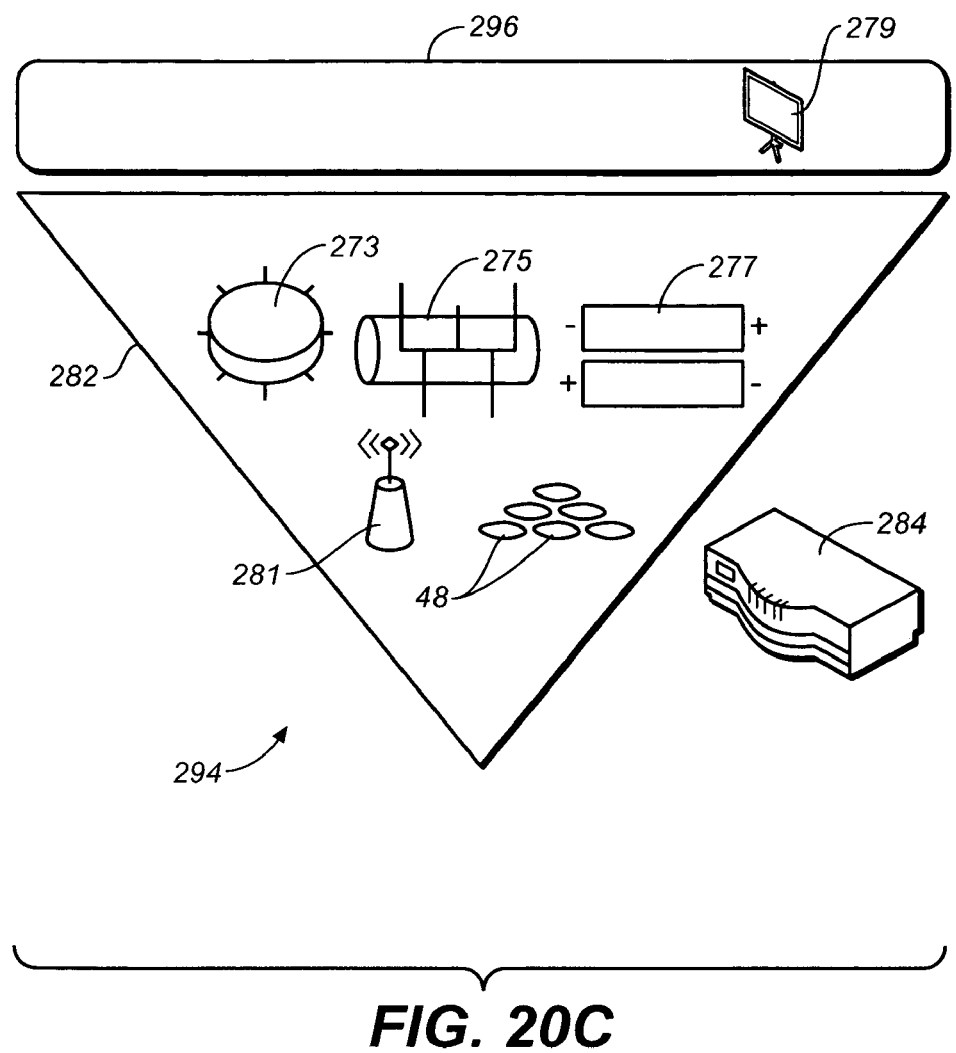
FIG. 20C is a schematic depiction of an exemplary architecture having a disposible body, portable docking station (fob), and a recharge station.

FIG. 20C is a schematic depiction of an exemplary architecture 294 having a disposable body containing an actuator 273, a PCB 275, a power supply 277, a user identification means 281, and a drug dosage cartridge containing drug dosage forms 48, a portable docking fob 296 containing a user interface 279, and a recharge station 284. The reusable option includes the following: a disposable body 282 with the portable docking fob 296, and a recharge station 284 for recharging the fob.

Figure 20D:
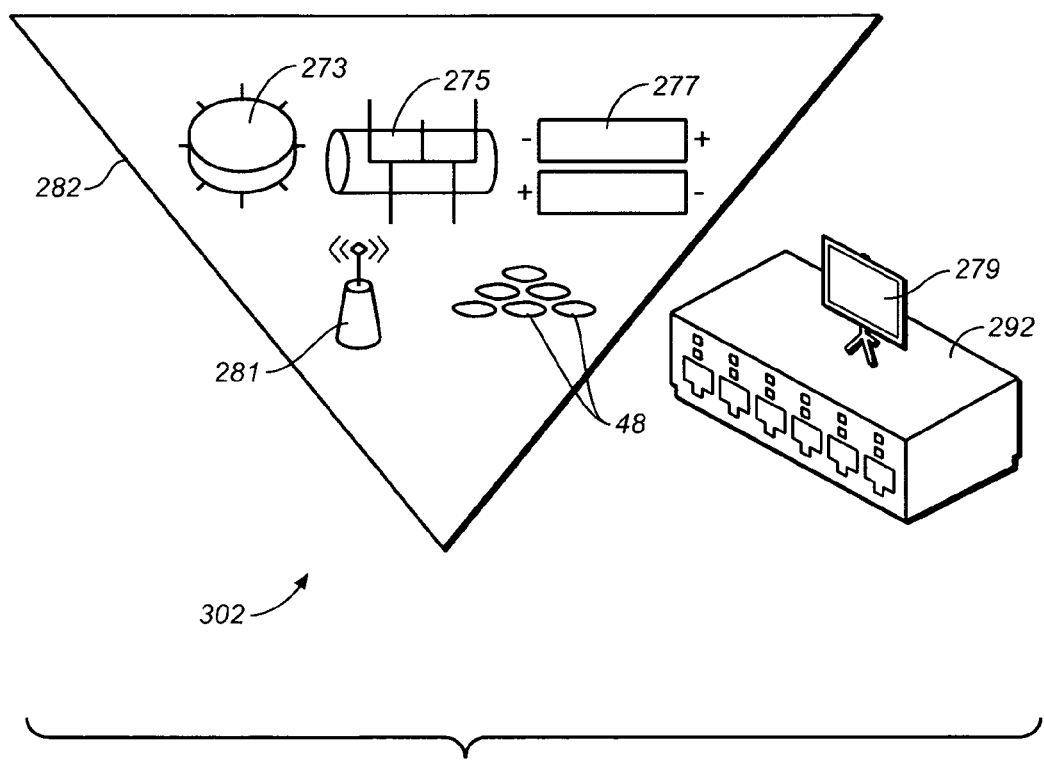
FIG. 20D is a schematic depiction of an exemplary architecture having a disposable body and a docking station.

FIG. 20D is a schematic depiction of an exemplary architecture 302 having a disposable body 282 with dockability. The reusable option includes the following: a disposable body 282 containing an actuator 273, a PCB 275, a power supply 277, a user identification means 281, and a drug dosage cartridge with drug dosage forms 48, and a docking station 292 containing a user interface 279. The reusable option includes the following: disposable body with a docking station.

Figure 20E:
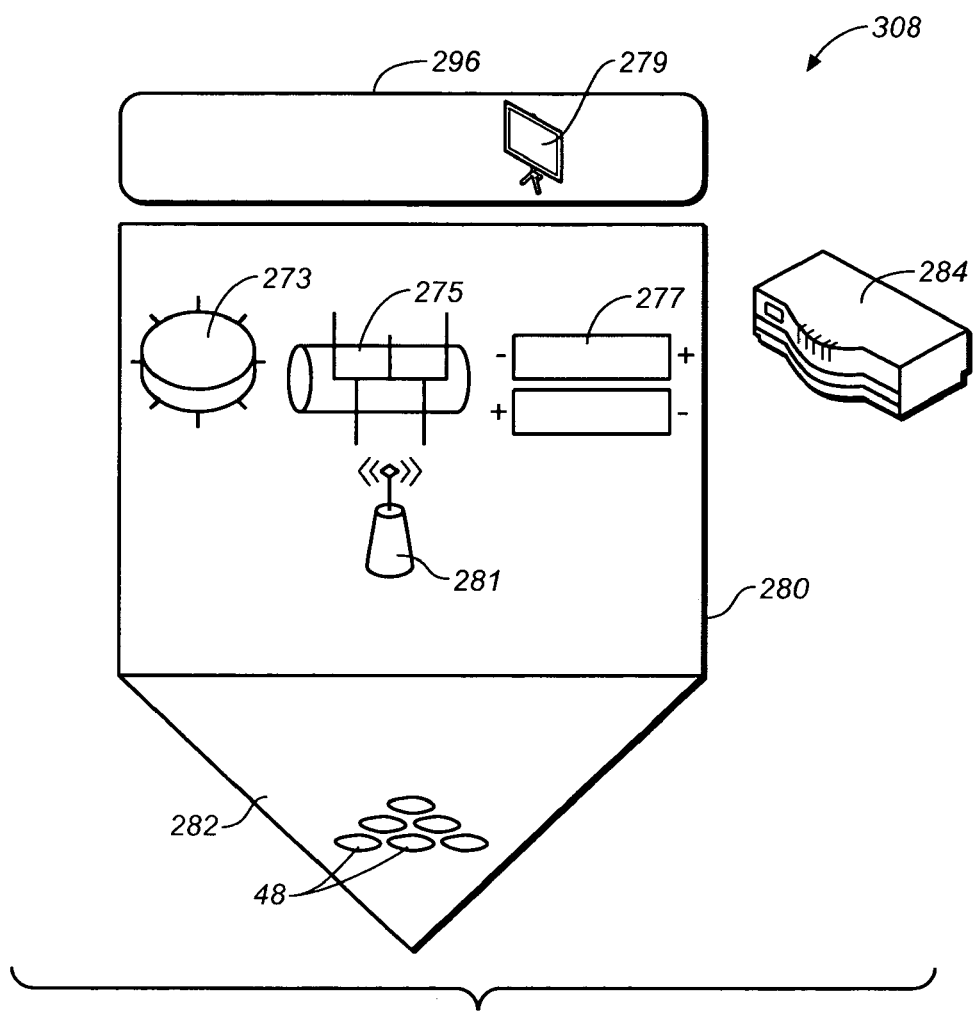
FIG. 20E is a schematic depiction of an exemplary architecture having a reusable head, disposible body, portable docking station, and recharge station.

FIG. 20E is a schematic depiction of an exemplary architecture 308 having a reusable head 280 containing a power supply 277, a microprocessor and printed circuit board (PCB) 275, an actuator 273, and a user identification means 281, a disposable body containing a drug dosage cartridge with drug dosage forms 48, a portable docking fob 296 containing a user interface 279, and a recharge station for the head and fob. The reusable option includes the following: the reusable head 280 with the fob 296, a disposable body 282, and a recharge station 284.

Figure 20F:
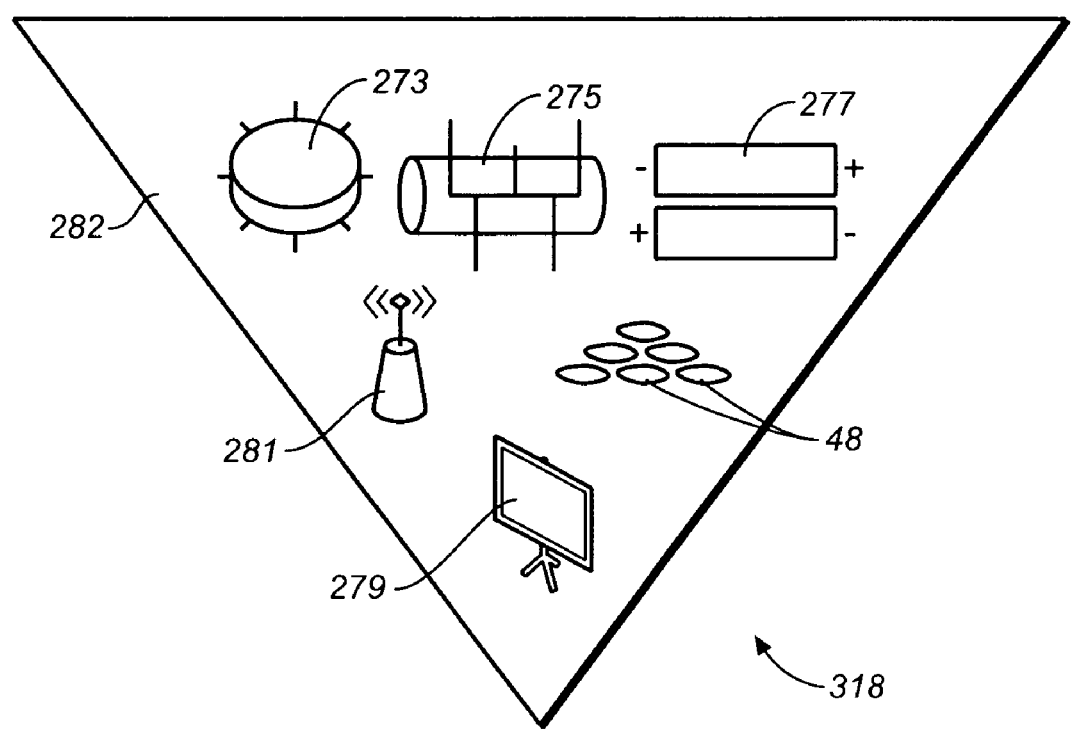
FIG. 20F is a schematic depiction of an exemplary architecture, wherein a fully disposable device is shown.

In one embodiment, the present invention further provides a fully disposable device. The device is one-piece incorporating all components necessary for drug dispensing and disposable after use, including a power supply 277, a microprocessor and printed circuit board (PCB) 275, an actuator 273, and a user identification means 281, a drug dosage cartridge with drug dosage forms 48, and a user interface 279. FIG. 20F is a schematic depiction of an exemplary architecture 318, wherein a fully disposable body 282 is shown.

The present invention further provides a dispensing device with a locking feature including movable push rod; non-returning push rod; electromechanical regulator; optical sensor pair; magnetic clutch; lockout on actuator; rack and pinion; safety button latch; solenoid; collet on shaft; keyed hubs; coupling; and cams.

System For Administration of Dosage Forms to a Patient

A system for administration of dosage forms to a patient using a drug dispensing device of the invention includes the drug dispensing device, drug dosage forms and a patient. Additional features which may be included in the system are a docking station or other docking means, a means of communication with a computer network such as a bidirectional communication link with a local or remote computer system (wired or wireless), a pharmaceutical network monitoring and control apparatus, a computer network that stores, records and transits information about drug delivery from the device and one or more user interfaces.

In one approach, the computer network of the dosage form dispensing system of the present invention may comprise one or more of: a means to store, record, receive, and transit information about drug delivery from the drug delivery device; an internal clock to track time and date, a means to reset or modify memory, a non-invasive means to measure respiratory rate, temperature, pulse rate, or blood pressure wherein the results are stored and transmitted via the computer network; a means to change the lock-out time of the drug delivery device or dispenser. A docking station that finds utility in practicing the present invention may function to retrieve, store, communicate data to another device, peripheral, or computer, and/or recharge a battery. The system further comprises one or more user interfaces and a graphic display such as an LCD display.

Figure 21:
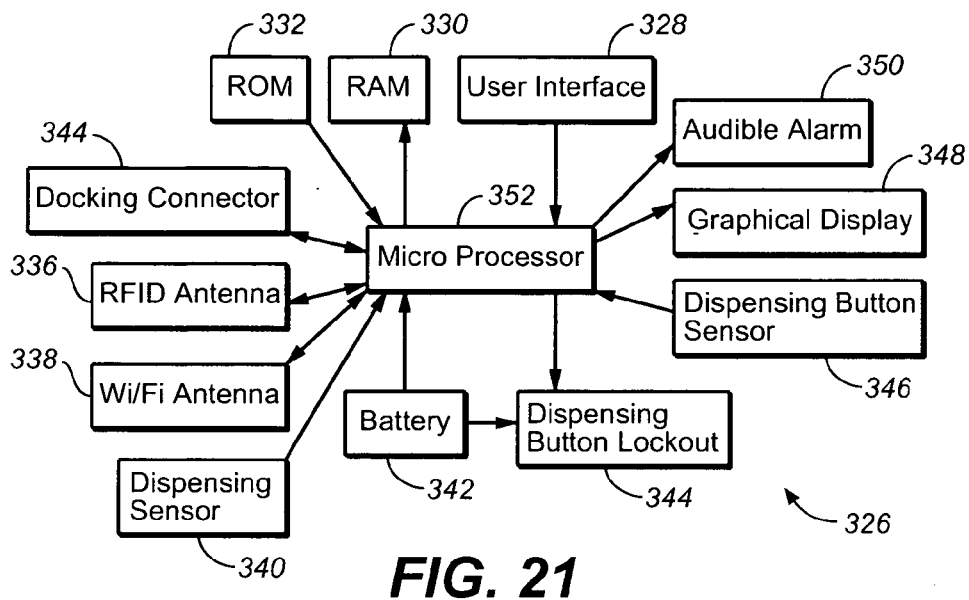
FIG. 21 is a schematic depiction of the functional elements of the drug dispensing system of the invention, including a drug dispensing device and pharmaceutical network with a monitoring and control apparatus coupled via a wireless or other bi-directional communication network. The system includes a battery powered microprocessor which comprises RAM and ROM, is operably connected to a docking connector, and communicates in a bi-directional manner with an RFID antenna, a WI/FI antenna, wherein the drug dispensing device and pharmaceutical network further comprises, a user interface, an audible alarm, a graphic display, a dispensing button and sensor, and a dispensing button lockout.

FIG. 21 is a schematic depiction of the functional elements of the drug dispensing system 326, including a drug dispensing device and pharmaceutical network with a monitoring and control apparatus coupled via a wireless or other bi-directional communication network. The system 326 includes a battery 342 controlled microprocessor 352 which comprises RAM 330 and ROM 332, is operably connected to a docking connector 334, and communicates in a bi-directional manner with an RFID antenna 336, a WI/FI antenna 338, wherein the drug dispensing device and pharmaceutical network further comprises, a user interface 328, an audible alarm 350, a graphic display 348, a dispensing button and sensor 346, and a dispensing button lockout 344. The device or dispensing device of the present invention may have a bidirectional communication link with a local or remote computer system, wherein the computer system provides a signal that allows the device to dispense a small-volume drug delivery dosage form. The drug delivery device can store and dispense many doses of a small, oral transmucosal drug formulation. The device/system 326 includes a memory means such as RAM 330 and/or ROM 332, the micro processor 352 or a central processing unit (CPU) for processing information and controlling various functional elements of the device 326 and a battery 342, the docking connector 334 that can allow the device 326 to connect to another device, peripheral, or computer to retrieve, store, communicate data to the another device, peripheral, or computer, and recharge the battery 342, the RFID Antenna 336 or other unique tag that allows easy identification of each individual device 326, the Wi/Fi Antenna 338 that allows information be communicated bi-directionally via a wireless system, a dispensing sensor located on the exit port to detect the successful dispensing of a dosage form.

Figure 22A:
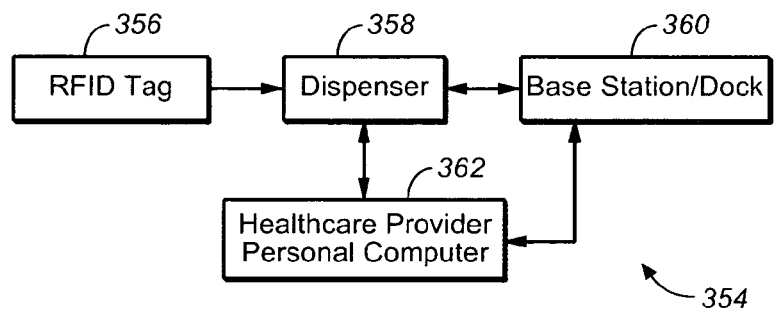
FIGS. 22A and 22B are block diagrams illustrating communication associated with a drug dispensing system of the invention.

FIG. 22A is a block diagram illustrating a system communication diagram 354, comprising an RFID tag 356, a dispensing device 358, a base station/dock 360 and a healthcare provider personal computer 362. The drug dispensing device 358 may communicate with the physician or care giver, via the dock 360, by means of a wired or wireless communication method to provide usage information and information regarding the respiratory status or blood pressure of the patient to the physician at regular intervals.

Figure 22B:
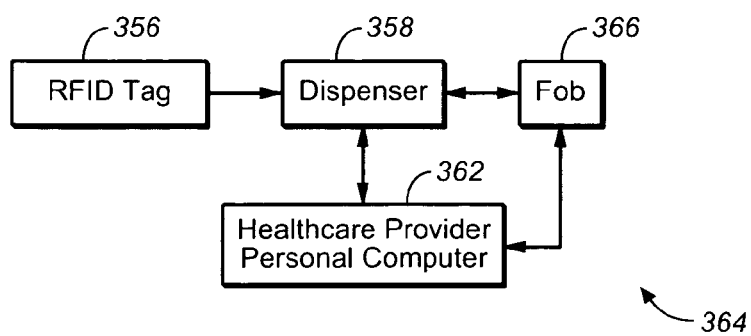

FIG. 22B is a block diagram illustrating a system communication diagram 364, comprising an RFID tag 356, a dispensing device 358, a fob 366 and a healthcare provider personal computer 362. The drug dispensing device 358 may communicate with the physician or care giver, via the fob 366, by means of a wired or wireless communication method to provide usage information and information regarding the respiratory status or blood pressure of the patient to the physician at regular intervals. The fob 366 can be adapted to attach to a cord so as to allow the fob 366 to hang from the neck of the physician or caregiver. This would help avoid misplacing the fob 366 or theft of the fob 366, such as in the hospital setting.

The present invention provides a drug dispensing system including a drug dispensing device and a detecting means for detecting the identity of a patient. The dispensing system may further include a computer, a docking station, an access control means, and small volume drug dosage forms. The system further comprises a docking station, wherein the docking station is electrically connected to a computer network and information is transmitted from the drug delivery device or dispensing device to the computer network. The computer network is wireless and information is transmitted from the drug delivery device or dispensing device to the computer network via the wireless network. The computer network stores, records and transits information about drug delivery from the drug delivery device. The system may further comprise a non-invasive means to measure respiratory rate, pulse rate, temperature or blood pressure wherein the results of the measurements are stored and transmitted via the computer network. In one embodiment, the system further comprises a means to change the lock-out time of the drug delivery device. In another embodiment, the system may comprise a drug delivery device with an antagonist reservoir that allows the antagonist and drug to combine in the event of a system or power failure, device damage or tampering. In addition, a means that uses a sensor to detect blood chemistry, breath chemistry, saliva chemistry and on the like is also provided Further embodiments of the device include the ability to store historical use information and the ability of the device to communicate with another device or computer to transmit such information. For example, such a bidirectional exchange of information may be accomplished by downloading stored information to a computer through a physically wired interface, such as a USB or any other communication connection. Alternatively, information may be communicated via a wireless system. Such information may include historical use information, for example the number of dosages stored and dispensed, and the times of dispensing.

In certain embodiments, the device includes a docking station that may query the device, reset it between dosing, lock it when not properly accessed, and control the dosing regimen. The drug dispensing device may communicate with a physician or care giver, via the dock, by means of a wired or wireless communication method to provide usage information and information regarding the respiratory status, blood pressure or other biometric measurement of the patient's status to the physician at regular intervals. The dispensing device may lock out at regular intervals or time periods, e.g., each day or week or two weeks, requiring the patient to dock the dispensing device and communicate with the physician or care giver to unlock the device for the next fixed period. In this way the device and dock enable greater physician oversight and care management.

In other embodiments, the docking station may load single or multiple doses into the device each time it is docked and properly accessed.

In certain embodiments, the device may be adapted to receive a cartridge of individually packaged single dose applicators each containing a single dose of the drug.

A drug dosage dispenser of the invention may be used to administer a drug dosage forms that is sensitive to moisture and/or humidity. In such cases, there is a need for a drug dosage form cartridge that protects the drug dosage form from humidity, moisture, saliva, mucus, etc. The cartridge may be cylindrical, disk-shaped, helical, rectilinear, non-ordered, or may take the form of any assemblage of drug dosage forms that allows the dispenser to dispense them in a controlled manner. To prevent the unused drug dosage forms from absorbing moisture or otherwise becoming exposed to moisture prior to use, the cartridge may provide a means of sealing the drug dosage forms from exposure to moisture. This may accomplished by use of a cartridge that contains individually packaged drug dosage forms separated by a thin impermeable foil or impermeable material such that when one drug dosage form is dispensed from the cartridge, the seal protecting the remaining dosage forms remains unbroken. Alternatively, the dosage forms may be packaged in such a manner within the cartridge that two or more dosage forms are packaged together in each separate sealed compartment. In some embodiments, all of the dosage forms in a cartridge may be packaged together in a foil sealed compartment.

The drug dosage form cartridge may afford a seal against moisture by means of a septum, an elastomeric seal or valve, a sliding, translating, hinged door or valve, or by means of sealing against another component of the dispenser when loaded. In this manner, a single re-sealable seal may be opened either independently or by means of the passage of a dosage out of the cartridge. Once the dosage form is delivered from the cartridge, the re-sealable seal on the cartridge may be re-sealed to prevent moisture or other contaminants from damaging the remaining drug dosage forms within the cartridge. The cartridge may further have a non-re-sealable seal that is broken when it is loaded into the dispenser or upon delivery of the first dosage form from the cartridge.

In other embodiments, the cartridge contains a desiccant or other absorbent or adsorbent material to absorb or adsorb moisture that penetrates the cartridge either prior to use or during normal use. A cartridge for use in a dispensing device of the invention may contain any combination of individually sealed dosage forms, multiply sealed dosage forms, re-sealable seals, non-re-sealable seals, desiccants, absorbents, or adsorbents.

In one exemplary embodiment a stack of solid tablet dosage forms is packaged in a cylindrical cartridge with a sliding seal at the distal end and a spring pre-loading the tablets toward this distal end. When the drug cartridge is loaded into the dispenser, the sliding seal remains in place, protecting the drugs within the cartridge from moisture and humidity. Upon dispensing of a dosage form, the sliding seal slides out of the way, allowing the spring to advance the stack so that a single tablet dosage form is dispensed. Once this tablet is dispensed, the sliding seal moves back into place to continue to seal the remaining tablets from moisture and humidity.

In a second exemplary embodiment, a stack of solid tablet dosage forms is packaged in a cylindrical cartridge with a foil seal at the distal end, a spring pre-loading the tablets toward this distal end, and a sealing surface that will seal against a component internal to the dispenser once it is loaded into the dispenser. When the cartridge is loaded into the dispenser, the foil seal is broken, and the distal end of the cartridge seals against a component of the dispenser so as to protect the tablet dosage forms from humidity and moisture. When a tablet is dispensed, a component of the dispenser that provides a seal to the cartridge is moved out of the way, allowing a single dosage form to be dispensed. Once the dosage form is dispensed, the dispenser re-seals the cartridge, protecting the remaining dosage forms from moisture and humidity.

In a third exemplary embodiment, a disk shaped cartridge with individual spaces for individual solid tablet dosage forms arranged around the periphery of the disk is loaded with solid tablet dosage forms and sealed on both faces with a metal foil to protect the tablets from moisture and humidity. When loaded into the dispenser and when a dosage form is dispensed, push rod breaks through the foil on one face at the location of one of the individual compartments, contacting the tablet dosage form, and pushing it through the second seal on the opposite face of the disk cartridge, breaking through the second foil, and dispensing the tablet. In this manner, only a single tablet is dispensed, and the seals for the remaining tablets remain intact, protecting them from moisture and humidity. After the dispensing of the tablet, the disk indexes one location so that the next compartment containing the next tablet is in position to be dispensed next. FIGS. 11A and 11B depict one such exemplary embodiment.

Dosage Forms Delivered with the Dispensing Device of the Invention

Oral transmucosal drug delivery is effective, easy to deliver, non-invasive, and can be administered by the caregiver or the patient with minimal discomfort. Generally, oral transmucosal delivery of pharmaceuticals is achieved using solid dosage forms such as lozenges or dosage forms, however, liquids, sprays, gels, powders, gums, foams, patches, and films may also be used. A drug dispensing device of the present invention provides a means to deliver a small-volume drug dosage form that is adapted for delivery of the drug via the oral mucosa.

In one embodiment, a drug dispensing device of the invention provides a means to deliver dosage forms for oral transmucosal delivery of pharmaceutically active substances. The dosage forms may be solid or non-solid and may serve as a delivery vehicle for any medication, e.g., a pain-relieving drug such as an opioid or an opioid agonists, or drugs for treating angina, anxiety, insomnia, ADHD, addiction, nausea, and so on. Solid dosage forms, such as sublingual dosage forms, troches, lozenges, powders, and films that can be used to deliver drugs via the oral mucosal tissue are considered to be within the scope of the invention.

The invention also encompasses drug dispensing devices for delivery of other non-solid dosage forms such as gels, salves, pastes, mists, liquids, aerosols, gases, vapors, foams, emulsions, sprays, suspensions and the like.

In one embodiment, a drug dispensing device of the invention provides a means to deliver small-volume drug delivery dosage forms, exemplified herein for the treatment of pain. In this embodiment, the dosage form is designed to remain in the sublingual area, adhering to the oral mucosa, and is small enough to elicit little or no saliva response from the patient. Although the dosage form is intended to remain in the sublingual space, it will be effective when absorbed through any oral transmucosal route.

In one embodiment, a drug dispensing device of the invention is used for administration of a small-volume drug delivery dosage form for oral transmucosal delivery of drugs, wherein the dosage form is prepackaged and is self-administered. The invention also encompasses use of the device to deliver a small-volume drug delivery dosage form for oral transmucosal delivery of drugs that are not prepackaged.

A means for minimizing saliva influx into a dispensing device for oral transmucosal administration of a drug dosage form comprises seals, wipers, absorbants, air gaps, desiccants, and multiple stage delivery systems. The dispensing device dispenses the drug dosage form one at a time without adversely affecting other drug dosage forms contained in a cartridge filled with the drug dosage form.

In one preferred embodiment, a drug dispensing device of the invention provides a means to deliver a drug dosage form that is generally very small, e.g., a NanoTab®. The NanoTabs® may be used to deliver any drug that may be administered by the oral transmucosal route in an amount amenable to administration via the small size of the NanoTabs®, i.e. about 0.1 mg to about 99.9 mg. In one preferred embodiment, the NanoTab® is adhered sublingually. The nanotab formulation described herein is generally very small. Its volume for example may be from 0.1 to 50 microliters, from 0.5 to 10 microliters, from 1.0 to 25 microliters or more preferably from 3 to 15 microliters. The dimensions of the nanotab may be, for example, from about 0.5 mm to 3 mm in thickness, and from about 1.0 mm to 10 mm in diameter. This small size allows the formulation to easily and comfortably adhere to the oral mucosa, and to deliver the drug while provoking a minimal saliva response. In a preferred embodiment, the formulation is adhered sublingually. The drug dispensing device of the present invention is easily handled, portable, relatively inexpensive and allows for timed lock-out periods to avoid overdosing, child-proof and theft-proof safety features, in addition to multi-unit dosing, such that days, weeks or months of medication can be housed in the device. The initial timed lock-out period may be from about 1 minute to 60 minutes, preferably 3 minutes to 40 minutes or 5 minutes to 30 minutes, and in particular cases is set at any one minute interval from 1 to 60 minutes, e.g., 5, 6, 7, 8, 9, 10, 11, 12, 13, 14, 15, 16, 17, 18, 19, 20, 21, 22, 23, 24, 25, 26, 27, 28, 29 or 30 minutes. The dispensing device may consist of any combination of the following: fully disposable or reusable tip portion, fully disposable or reusable cartridge portion, fully disposable or reusable head portion, fully disposable or reusable head and tip combination, a fixed or portable dock for access and data transfer, a recharge station, a diagnostic station, and a keyed assembly and disassembly station. The dispensing device affords mechanical protection for the tablets contained therein, preventing breakage, chipping, etc., thereby allowing for dispensing of the small fragile and friable nanotabs of the inventions to be dispensed.

The dosage form will typically comprise 0.01%-99% w/w of the active ingredient(s) percent by weight of the active ingredient or "drug". The term "drug" as used herein means any "drug", "active agent", "active", "medication" or "therapeutically active agent". In some embodiments, the dosage form is a NanoTab®, which may be used to deliver any drug that may be administered by the oral transmucosal route in an amount amenable to administration via the small size of the dosage form, e.g., up to 99.9 mg of drug, for example, 0.25 µg to 99.9 mg, 1 µg to 50 mg or 1 µg to 10 mg of drug. In one exemplary aspect, the invention relates to oral transmucosal delivery of pain-relieving drugs such as opioids or opioid agonists, for the treatment of acute or break-through pain. Such dosage forms or nanotabs for use in a method for the treatment of acute pain may comprise from about 0.25 to about 200 mcg of sufentanil, from about 0.25 to about 120 mcg of sufentanil, from about 2.5 to about 40 mcg of sufentanil, from about 5.0 to about 15.0 mcg of sufentanil, from about 2.0 to about 1500 mcg of fentanyl, from about 2.0 to about 900 mcg of fentanyl, from about 7.5 to about 300 mcg of fentanyl, or form comprises from about 20 to about 100 mcg of fentanyl. The small-volume drug delivery dosage forms or nanotabs contain from about 0.25 to about 200 mcg of sufentanil per tablet for oral transmucosal delivery. In one preferred embodiment, the drug is sufentanil, provided alone or in combination with an additional drug effective to treat pain. Exemplary nanotabs for administration to children (pediatric patients) contain from about 0.25 to about 120 mcg of sufentanil per tablet. For example, a nanotab of the invention for administration to children may contain about 0.25, 0.5, 1, 2.5, 4, 5, 6, 8, 10, 15, 20, 40, 60 or 120 mcg of sufentanil for oral transmucosal delivery. It follows that for pediatric patients, an exemplary dose range is from at least about 0.02 mcg/kg to about 0.5 mcg/kg with a preferable range of from about 0.05 to about 0.1 mcg/kg. Exemplary nanotabs for administration to adults contain from about 2.5 to about 200 mcg of sufentanil per tablet per tablet. For example, a nanotab for administration to adults may contain about 2.5, 3, 5, 7.5, 10, 15, 20, 40, 60, 80, 100, 120, 140, 180 or 200 mcg or more of sufentanil for oral transmucosal delivery. In one exemplary situation, the initial lock-out time is set from about 15-20 minutes for a nanotab containing from about 5-20 mcg of sufentanil.

The shape of a drug dosage form for use in practicing the invention is preferably approximately disc-shaped, but may be rectangular, square, polygonal, oval or spherical, any combination of these, or may be non-symmetric. When disc-shaped, the flattened surface provides an increased surface area for adhesion and drug elution. The drug dosage form may be formed in any geometry that may be delivered using a drug dispensing device of the invention. Optimally the drug dosage forms are formed as round discs with flat, concave, or convex faces. Alternately, they may be ellipsoids with flat, concave, or convex faces, or polygons with 3 or more edges and flat, concave, or convex faces. The drug dosage forms may also be spherical, ellipsoidal, or have the shape of any other curved solid body. The drug dosage forms may also be any non-symmetrical shape and may enable specific handling and orientation in the dispenser device and during placement.

FIGS. 23A and 23B provide depictions of exemplary drug shapes. FIG. 23A is a schematic depiction of symmetric drug dosage forms 368 including round discs with flat, concave, or convex faces, ellipsoids with flat, concave, or convex faces, spherical, polygons with 3 or more edges and flat, concave, or convex faces. or any other curved solid body. FIG. 23B is a schematic depiction of other drug shapes 370 in asymmetric dosage forms.

In one exemplary formulation, the dosage form is approximately disc-shaped, the volume of the drug dosage form is about 5 microliters, and the dimensions of the drug dosage forms are approximately 0.85 mm in thickness, and 3.0 mm in diameter. The invention encompasses a small-volume drug delivery dosage form or nanotab for oral transmucosal delivery of drugs, exemplified herein for the treatment of pain. The nanotab is designed to remain in the sublingual area, adhering to the oral mucosa, and is small enough to elicit little or no saliva response from the patient. The small size of the formulation, and its ability to adhere to the oral mucosa while in use, minimizes the saliva response and thereby minimizes undesired delivery of the drug to the gastrointestinal (GI) tract, ensuring that the majority of drug is delivered across the oral mucosa, and not via the gut. Minimizing the saliva response produces a delivery profile that is consistent and predictable from patient to patient, which is not the case with oral lozenge formulations that produce a significant saliva response. A reduced saliva response is particularly important for drugs with poor bioavailability in the GI tract, such as opioids. The nanotab formulation described herein is generally very small. Its volume for example may be from 0.1 to 50 microliters, from 0.5 to 10 microliters, from 1.0 to 25 microliters, or more preferably from 3.0 to 15 microliters. The dimensions of the nanotab may be, for example, from about 0.5 mm to 3 mm in thickness, and from about 1.0 mm to 10 mm in diameter. This small size allows the formulation to easily and comfortably adhere to the oral mucosa, and to deliver the drug while provoking a minimal saliva response. In a preferred embodiment, the formulation is adhered sublingually.

A drug dispensing device of the invention will provide a number of dosage forms that will vary according the nature and amount of active ingredients while maintaining the size and features appropriate for efficacious delivery.

A device of the invention can be loaded with many days worth of medication (e.g., 30 days or more) at one time, and may require no special packaging for the medication. Alternatively, the medication may be provided in the form of a pre-filled cartridge.

The present invention provides the advantage that the drug is delivered via a dispensing device which provides for the dispensing of multiple dosages of a small-volume oral transmucosal drug delivery dosage form such that the appropriate dose and frequency for therapeutic efficacy may be obtained, while simultaneously providing a timed lock-out feature to prevent accidental overdosing. The dose and corresponding lock-out time may be adjusted dependent upon the size of the subject and the intended therapeutic goal.

As set forth above, a drug dispensing device of the invention comprises a means for minimizing saliva influx into the device when used for oral administration. In this embodiment, he dispensing device dispenses the drug dosage form one at a time without adversely affecting other drug dosage forms contained in a cartridge filled with additional drug dosage forms. A means for trapping or otherwise isolating saliva or moisture once it has entered the device may include but is not limited to a hydrophilic wicking material or component, an absorbent or adsorbent material or component, or a desiccant material or component, or any combination of these materials or components.

Types of Drugs Delivered with the Dispenser and Therapeutic Indications

Any drug that can be administered in a dosage form that fits a drug dispensing device of the invention may be used in the methods and systems of the invention.

Similarly, a drug dispensing device of the invention may be used to treat any condition wherein the appropriate dosage form can e delivered using the device.

In one exemplary aspect, a drug dispensing device of the invention may be used for oral transmucosal delivery of pain-relieving drugs such as opioids or opioid agonists, for the treatment of acute pain and acute break-through pain. In this embodiment, a drug dispensing device of the invention finds utility in the hospital setting for use in place of IV opioids for treatment of acute pain and also in the outpatient setting for treatment of acute breakthrough pain. Examples include, the in-patient (hospital setting), wherein the need for rapid treatment of acute pain occurs in many different clinical situations, including post-operative recuperation, rheumatoid arthritis, failed back, end-stage cancer, and so on. Post-operatively, for example, patients suffer from severe pain for the first few days followed by days of mild to moderate levels of pain for several more days.

The drug dispensing devices of the invention allow patients to self-administer pain and other medication, redosing as needed to titrate their dosing and achieve a desired level of therapeutic efficacy.

To effectively operate in the inpatient setting, a patient controlled dispensing device should allow the patient to self dose as needed, prevent the patient from over dosing, record the dosing history, allow for the dosing history to be read, downloaded, or otherwise transferred to a patient's records, deliver the drug dosage form to the appropriate location (e.g. sublingual, buccal, oral gastro-intestinal, rectal, ocular, nasal, inhalation, aural, transdermal or any other route of administration) and prevent or deter unauthorized individuals from gaining access to the drugs. The dispensing devices of the invention may be used to dispense any medication in the inpatient setting affording the desired combination of the above-described features.

Another exemplary use for a drug dispensing device of the invention, is in the treatment of acute pain which is necessary for patients in an outpatient setting, e.g., after outpatient surgical procedures, as a result of a chronic condition, or as a result of an accidental injury. Many patients use opioids on a weekly or daily basis to treat their pain. While they may have a long-acting oral or transdermal opioid preparations to treat their chronic underlying pain levels, they often need short-acting potent opioids to treat their severe breakthrough pain levels. These breakthrough pain events may last from minutes to hours, days or weeks.

Treatment of acute pain is also necessary "in the field" under highly sub-optimal conditions. First responders, such as paramedics or military field medics often are required to treat severe acute pain in non-sterile situations, where needles used for IV or IM administration can result in unintended risks, such as infection, and so on. Oral opioid dosage forms often take well over 30 minutes to provide relief which is too long for someone in severe pain. A drug dispensing device of the invention, finds utility in such situations as well as for other indications such as treatment of angina, often treated with nitroglycerine dosage forms.

When used in the outpatient chronic (home, office, field, etc.) setting, a drug dispensing device of the invention offers several features and advantages over the state of the art in outpatient drug administration. The dispensing device allows individuals to self administer drugs in accordance with physician, healthcare provider, or drug label guidelines.

In the above clinical settings, there is clearly a need for a drug dispensing device which t may be used safely and conveniently, and provides for efficacious drug delivery while preventing abuse and diversion of the drug.

Those of skill in the art will appreciate that by controlling the amount of drug delivered over time and the delivery route, the dose can be optimized while generally consuming less active ingredient, thus reducing side effects.

Methods of Use of a Drug Dispensing Device of the Invention for Oral Transmucosal Drug Delivery Delivery of a single dosage form using a drug dispensing device of the invention may be accomplished as detailed in the figures described below.

Figure 24:
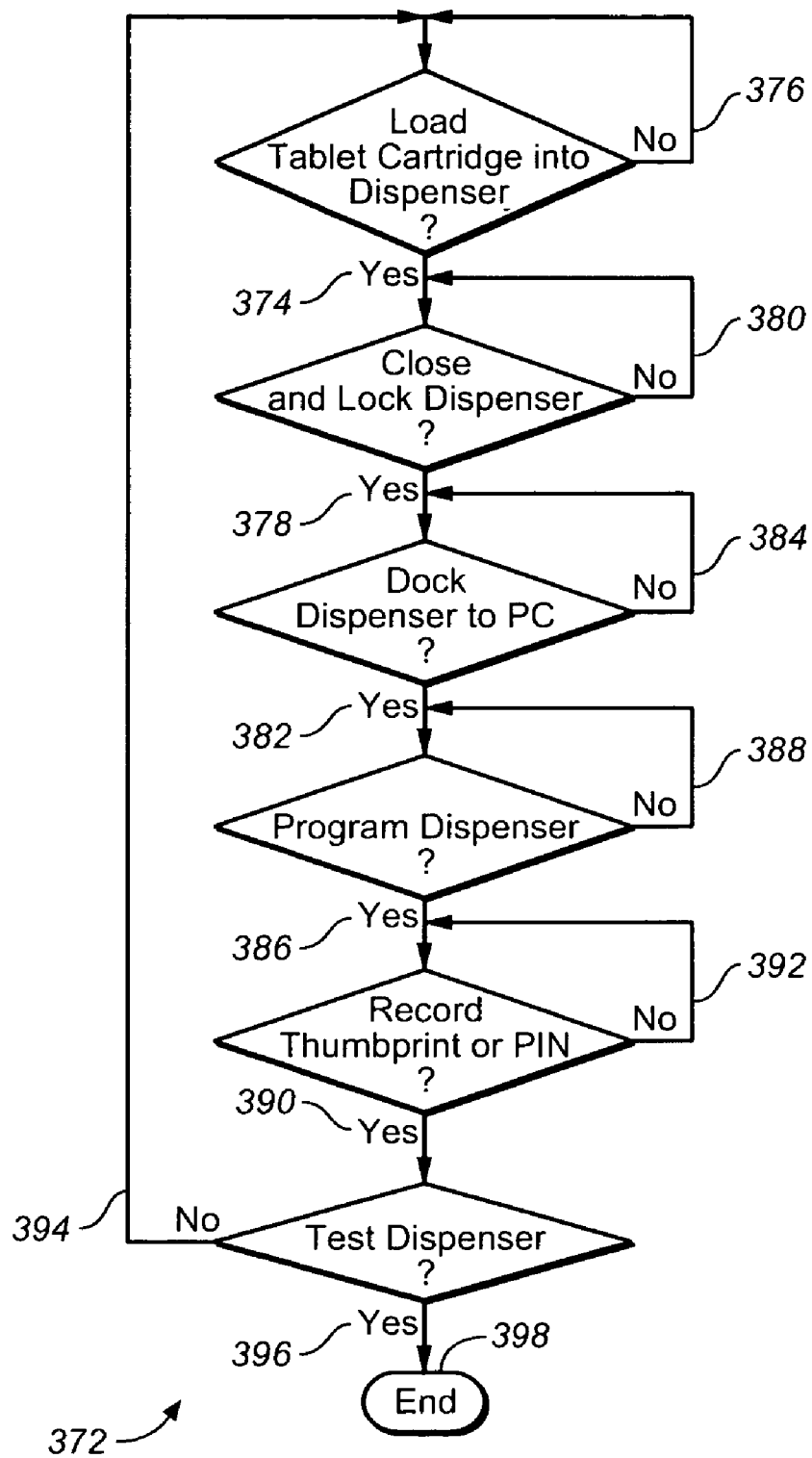
FIG. 24 is a block diagram of a setup and programming flow chart for a drug dispending system of the invention, wherein the process involves the steps of: loading a dosage form cartridge into the dispensing device; closing and locking the dispensing device; docking the dispensing device into the PC; programming the dispensing device; recording a thumbprint or PIN to identify the appropriate user; and testing the dispensing device.

FIG. 24 is a block diagram illustrating a dispensing device programming flow chart 372, wherein the process involves the steps of: loading a dosage form cartridge into the dispensing device. If loading is successful 374, the process goes to the next step. If unsuccessful 376, the process goes back to the first step of loading a dosage form cartridge into the dispensing device; closing and locking the dispensing device. If successful 378, the process goes to the next step. If unsuccessful 380, the process goes back to the previous step of closing and locking the dispensing device; docking the dispensing device into the PC. If successful 382, the process goes to the next step. If unsuccessful 384, the process goes back to the previous step; programming the dispensing device. If successful 386, the process goes to the next step. If unsuccessful 388, the process goes back to the previous step; recording a thumbprint or PIN to identify the appropriate user. If successful 390, the process goes to the next step. If unsuccessful 392, the process goes back to the previous step; and testing the dispensing device if a dispensing works properly. If successful 396, the programming ends 398. If unsuccessful 394, the process goes back to the first step to correct the programming.

Figure 25:
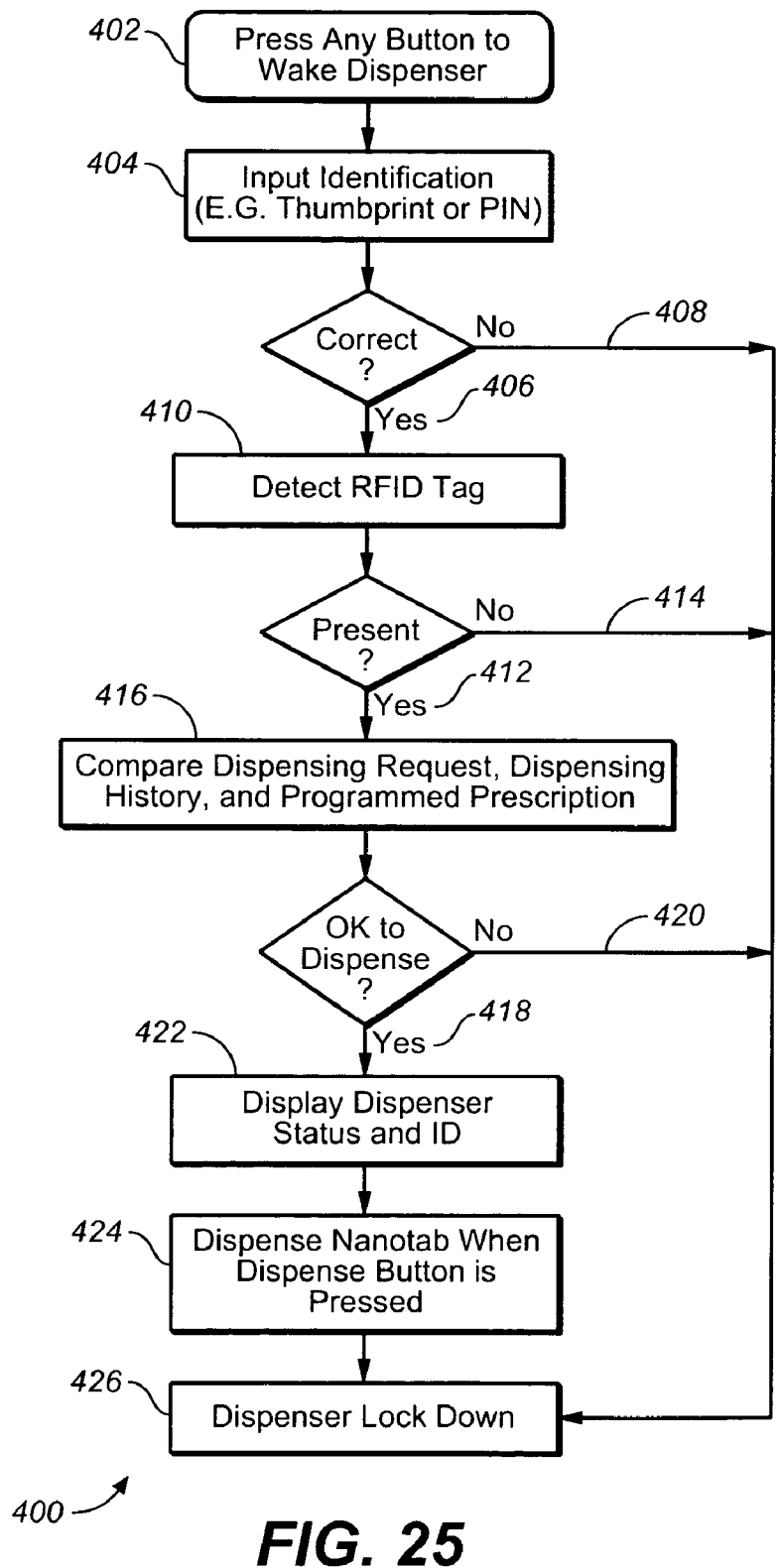
FIG. 25 is a block diagram illustrating a dispensing device operation flow chart, wherein one example of stepwise operation of a drug dispensing device of the invention is provided.

FIG. 25 is a block diagram illustrating a dispensing device operation flow chart 400, wherein an example of stepwise operation of a drug dispensing device of the invention is provided. The detailed steps include: pressing any button to wake-up the dispensing device 402. The user verifies if a preprogrammed lock-out time is over. If the preprogrammed lock-out time is not over yet, the user goes back to the prior step of waking up the dispensing device and repeats the process. If the verification is satisfied, the dispensing device is unlocked for dispensing a drug dosage form. Inputting patient identification 404 using e.g., a thumbprint, RFID, or PIN, is performed. If the patient identification is correct 406, the process goes to the next step: detecting an RFID tag 410. If incorrect 414, it results in lock-down of the drug dispensing device. If detecting an RFID tag is successful 412, the user proceeds to the next step by which the user verifies if a lock-out device is not blocking delivery and dispensing is fine. Then a comparison is made of the (a) dispensing request, (b) dispensing history, and (c) programmed prescription 416. If (a), (b) and (c) are consistent with permission to dispense a dosage form from the drug dispensing device of the invention, dispensing is ready 418. If not ready, lock-down of the dispensing device is resulted in 420. Displaying dispensing device status and ID which indicates the drug dispensing device is ready 422. Dispensing a dosage form when the dispense button is pressed 424. The dispensing device begins to dispense the drug dosage form to a patient. Upon completion of dispensing the dosage form, the dispensing device lock-out is locked down for a preprogrammed period 426. The steps are repeated for a future dispensing of the drug dosage form.

Figure 26:
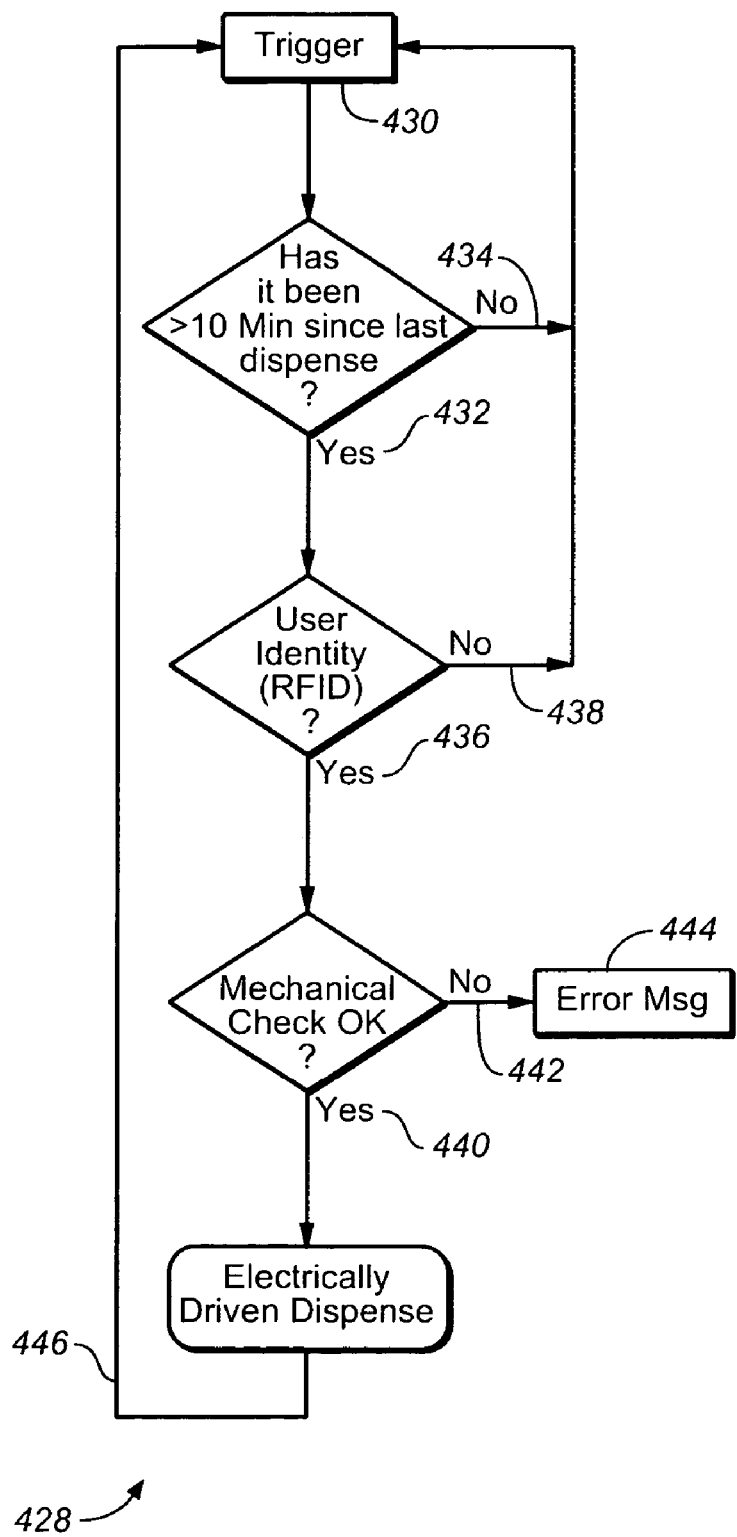
FIG. 26 is a block diagram illustrating another exemplary dispensing device operation flow chart, wherein a second example of stepwise operation of a drug dispensing device of the invention is provided.

FIG. 26 is a block diagram illustrating another exemplary dispensing device operation flow chart 428, wherein an example of stepwise operation of a drug dispensing device of the invention is provided. The method comprises the following steps: a user may press any button to wake-up the dispensing device 430. Then the device verifies if a preprogrammed lock-out time, such as 10 min, is over. If the preprogrammed lock-out time is over, patient identification is attempted, i.e. using 432, detecting an RFID tag is performed. If the preprogrammed lock-out time is not over yet 434, the user goes back to the prior step of waking up the dispensing device and repeats the process. If detecting an RFID tag is successful 436, the device proceeds to the next step and verifies that it is the mechanical dispensing is in functional condition. If detecting an RFID tag is unsuccessful 438, the user goes back to the first step. If the verification is satisfied 440, the dispensing device is unlocked for dispensing a drug dosage form. If the verification is not satisfied 442, an error message indicating a failure of the mechanical check is prompted 444. If the mechanical check is ok, then the motor-driven dispensing of a drug dosage form to a patient is performed. Upon completion of dispensing, the dosage form, the dispensing device lock-out is locked down for a preprogrammed period. The steps are repeated for a future dispensing of the dosage form 446.

In another example of the process of dispensing drug dosage forms using a drug delivery device of the present invention, the process includes the steps of: (1) load; (2) check; (3) position; and (4) deliver. This process comprises the following steps: (1) loading the drug dispensing device with a plurality of drug dosage forms; (2) checking the delivery status and verifying, for example, by a green light indicating that the lock-out mechanism is not blocking delivery and the device is armed with a drug dosage form; (3) positioning the device to deliver a dosage form of the invention under the tongue of the appropriate patient; and (4) delivering the dosage form to the patient by activating the device. The red light or other indicator is always visible when the device is not ready for delivery. The drug dispensing information is communicated to health care personnel such that the dosing regimen is adjusted to ensure that the patient is receiving the appropriate drug dose at the appropriate frequency to provide therapeutic efficacy.

Figure 27:
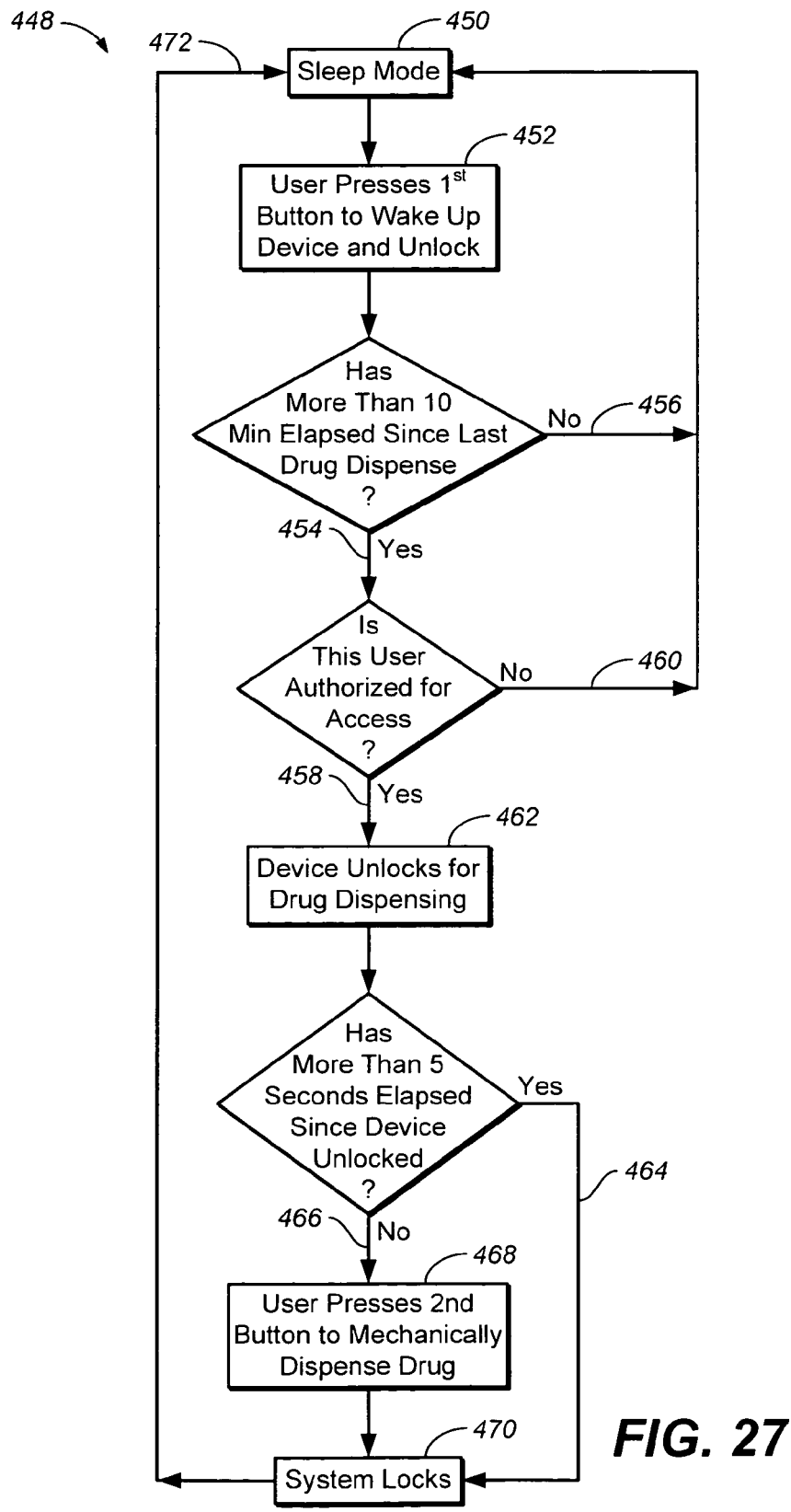
FIG. 27 is a block diagram illustrating another exemplary dispensing device operation flow chart, wherein a third example of stepwise operation of a drug dispensing device of the invention is provided.

FIG. 27 is a block diagram illustrating another exemplary dispenser operation flow chart 448, wherein an example of stepwise operation of a drug dispensing device of the invention is provided. The method comprises the following steps: a user presses any button to wake-up and unlock the dispenser 452 in sleep mode 450. Then the user verifies if a preprogrammed lock-out time, such as 10 min, is over. the preprogrammed lock-out time is over 454, the system verifies that the user is authorized for access, such as detecting a user identity (e.g. an RFID tag, fingerprint, etc.), is performed 458. If the preprogrammed lock-out time has not expired 456, the system returns to the first step of waking up the dispenser and repeats the process. If the user identity is detected and authorized 458, the system proceeds to the next step in which the system is unlocked for delivery 462. If the user identity is not detected or not authorized 460, the system returns to the first step of waking up the dispenser and repeats the process. Once the system is unlocked, it remains unlocked for 5 seconds before re-locking 464. If the user presses the second button before the 5 seconds has elapsed 466, the button will dispense a dosage form 468. Once the dispensing is completed, the system is locked 470 until the next dispensing attempt is made. The steps are repeated for a future dispensing of the dosage form 472.

Figure 28:
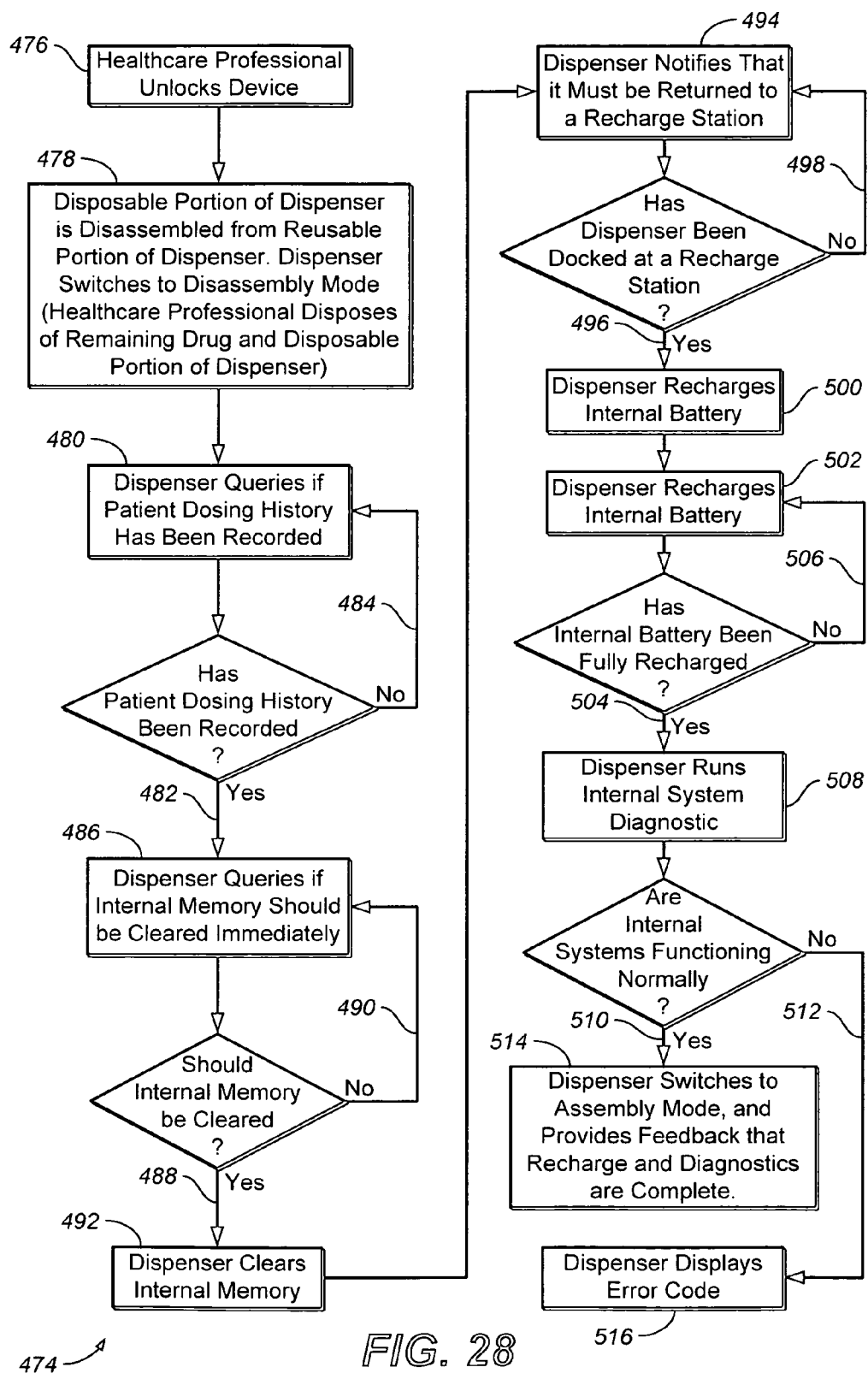
FIG. 28 is a block diagram illustrating exemplary dispensing device disassembly flow chart by a healthcare professional, wherein an example of stepwise disassembly of a drug dispensing device of the invention, following use, is provided.

FIG. 28 is a block diagram illustrating an exemplary dispenser disassembly flow chart by a healthcare professional 474, wherein an example of stepwise disassembly of a drug dispensing device of the invention is provided. As exemplified in FIG. 28, a healthcare professional may disassemble and dispose of the dispenser in a secure, controlled manner.

Figure 29:
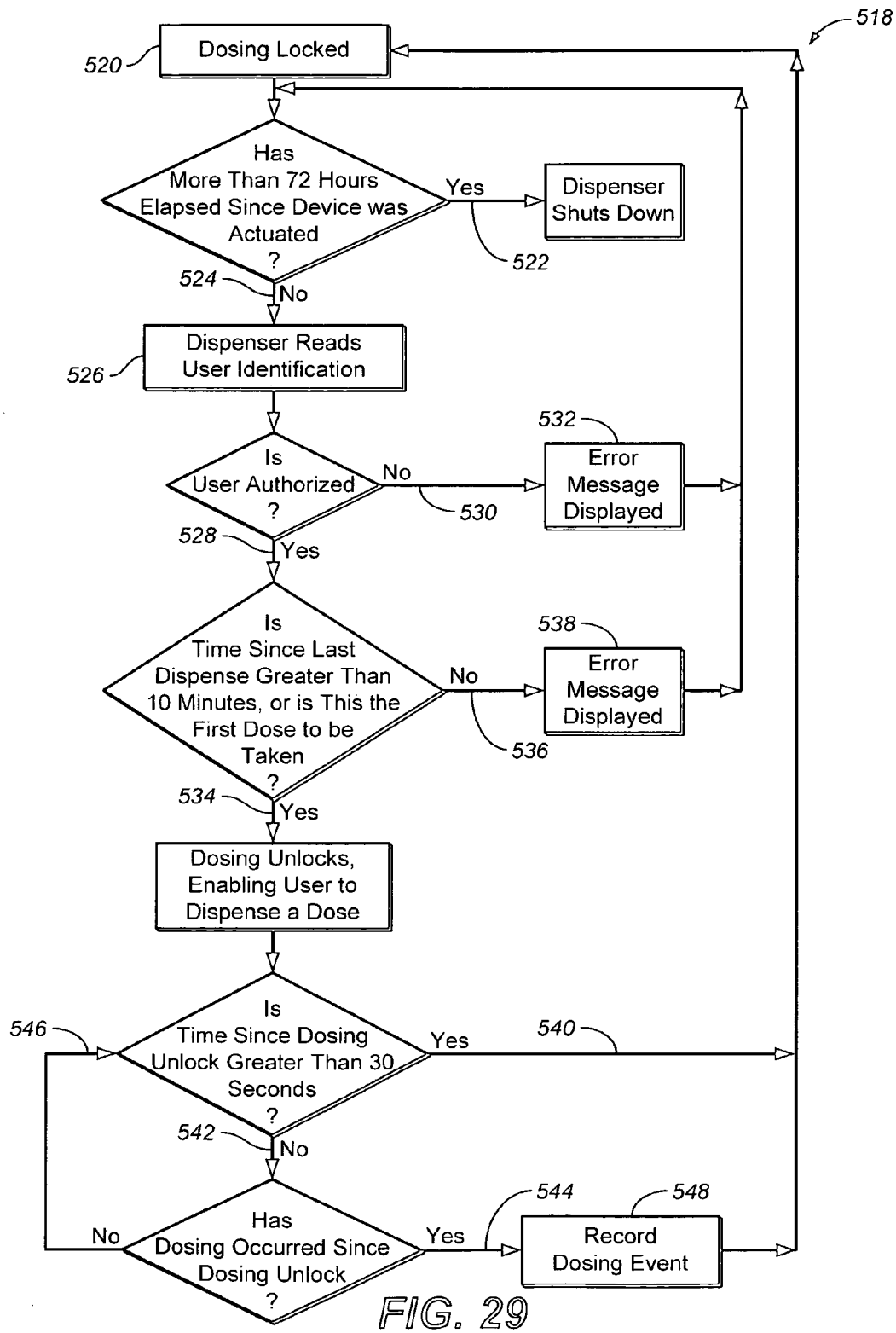
FIG. 29 is a block diagram illustrating an exemplary outpatient acute dispensing device operation flow chart, wherein an example of stepwise operation of a drug dispensing device of the invention is provided.

FIG. 29 is a block diagram illustrating an exemplary outpatient acute dispensing device operation flow chart 518, wherein an example of stepwise operation of a drug dispensing device of the invention is provided. FIG. 29 depicts a stepwise operation of an exemplary outpatient acute dispensing device.

Figure 30:
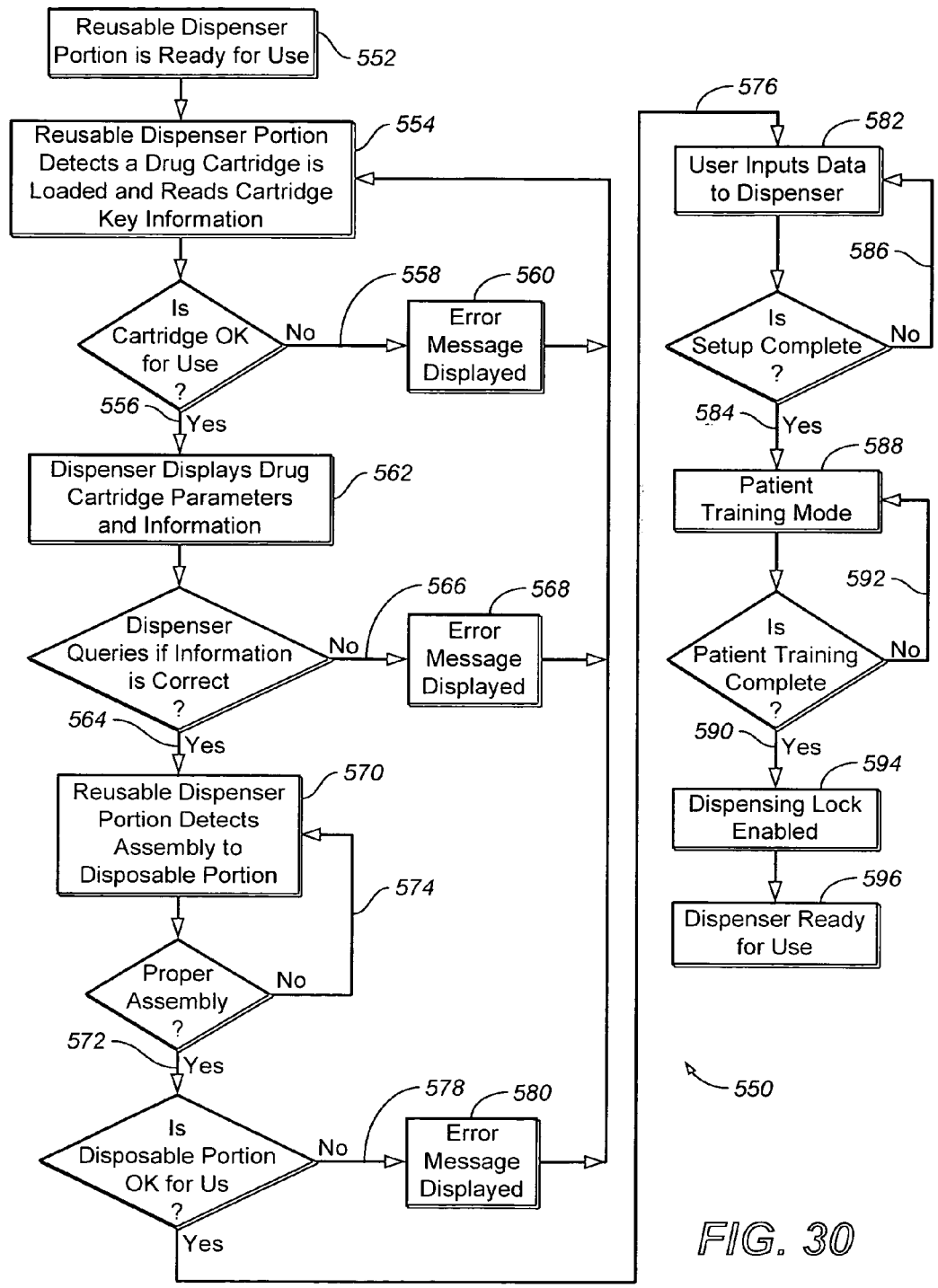
FIG. 30 is a block diagram illustrating an exemplary inpatient dispensing device setup and assembly flow chart, wherein an example of stepwise setup and assembly of a drug dispensing device of the invention, prior to use, is provided.

FIG. 30 is a block diagram illustrating an exemplary inpatient dispenser assembly and preparation flow chart 550, wherein an example of stepwise assembly and preparation of a drug dispensing device of the invention is provided. FIG. 30 depicts a stepwise assembly and preparation of the inpatient dispenser.

Figure 31:
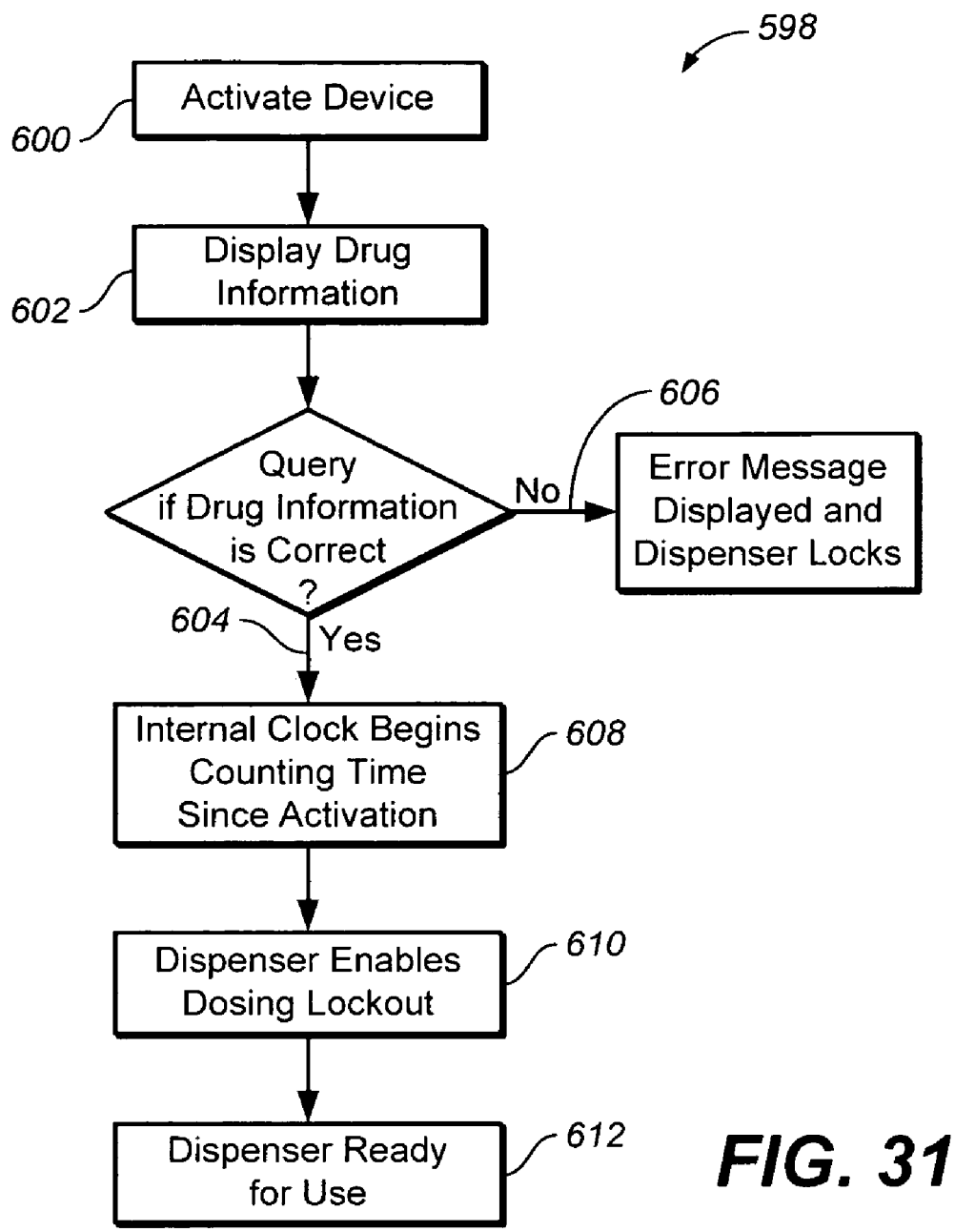
FIG. 31 is a block diagram illustrating an exemplary outpatient chronic dispensing device setup and assembly flow chart, wherein an example of setup and assembly operation of a drug dispensing device of the invention is provided.

FIG. 31 is a block diagram illustrating an exemplary outpatient chronic dispensing device operation flow chart 598, wherein an example of stepwise operation of a drug dispensing device of the invention is provided. FIG. 31 depicts a stepwise operation of the outpatient chronic dispensing device.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

Example 1

A physician determines that a patient requires acute pain management therapy. A pharmacist loads a drug dispensing device with a cartridge which includes the desired strength dosage form. Each cartridge has two colored placebo dosage forms arranged to be the first two dosage forms dispensed. The device has a means for loading the cartridge, which is either a port, hatch, or door that is secure and inaccessible to unauthorized users. Once the pharmacist has loaded the cartridge into the device, he locks the device access port, hatch or door. The pharmacist then docks the dispensing device for the first time to a dock that is connected to a personal or other computer, using the docking connector, and then programs the device. Programming involves uploading the dosage strength of the dosage forms, the number of dosage forms loaded in the device, the prescribed frequency of dosage form usage, the number of dosage forms to be used per day, the current date and time, the preferred language, a valid thumbprint or other identification for identifying the patient, and the physician's identification information, in case the device is lost and found.

Once the dispensing device is programmed, the pharmacist demonstrates proper usage and tests the device by dispensing a single blue placebo dosage form. The pharmacist then gives the dispensing device to the patient and observes the patient dispense a placebo dosage form to ensure proper usage and functionality. Along with the dispensing device, the pharmacist provides the user with a radio frequency identification (RFID) key that must be within approximately 5 inches of the device to allow the dispensing device to operate.

When the patient wants to administer a dose of the drug, he or she will hold the dispensing device, and push any button to wake the device up from its sleep mode. The device will query the user for either a thumbprint reading or a personal identification number (PIN). The device will then search for a validated RFID key within range. Once these conditions are met, the dispensing device will query its internal memory and clock to make sure that the dosage regimen programmed by the pharmacist is not being violated by the current usage request. At this point the device displays status information, such as the date and time, the number of doses left, the last time a dosage was used, the patient's name, etc., and the pharmacist informs the patient that the device is ready to dispense the dosage forms by a visual and/or audible signal.

The patient will hold the dispensing end of the device under his or her tongue and press the dispensing lever. When the dosage form is dispensed a tone will sound to inform the patient that the dosage form was properly delivered. At this point the device will lock down to prevent further dispensing until the preprogrammed lock-out time has passed, at which time the device will be ready to use again.

Example 2

In a hospital environment, where a patient is under more direct supervision, a drug dispensing device wherein access and identification is limited to the detection of an RFID key, and does not require a thumbprint or PIN is provided. A post operative or otherwise incapacitated patient can operate the device without undue physical exertion. Alternatively, an attending nurse or physician can dispense a dose to the patent. The use of the RFID key prevents the possibility of accidentally or intentionally switching devices with another patient.

The dosage form dispensing device is in periodic contact with the nurse's station via wired or wireless communication (WI-FI). This will allow the healthcare staff to monitor the use of the dosage form dispensing device and the number of remaining doses. The WI-FI communication allows the nurse to fully query the dispensing device at any time to see the use history and device status, including battery life, doses used, when the doses were used, doses remaining, etc. The components of the dispensing device are related in a drug dispensing system.

Although the foregoing invention has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

What is claimed is:

1. An apparatus for sublingual administration of a drug-containing tablet, comprising:
   a housing defining a delivery passage through which the tablet can be passed, the delivery passage having an S-shape, a distal end portion of the housing defining an exit port; and
   a push rod, at least a portion of the push rod being disposed in the delivery passage, the push rod being movable within the delivery passage between a first position in which an end portion of the push rod is disposed within the delivery passage and a second position in which the end portion is extended from the exit port, at least a portion of the push rod being sufficiently flexible to assume the S-shape of the delivery passage as the push rod is moved from the first position to the second position.

2. The apparatus of claim 1, further comprising:
   a seal disposed over the exit port, the end portion of the push rod is configured to extend through the seal when the push rod is in the second position.

3. The apparatus of claim 1, further comprising:
   a hydrophilic material disposed to minimize saliva influx into the delivery passage.

4. The apparatus of claim 1, wherein the push rod is configured to advance the tablet through the exit port when the push rod is moved from its first position to its second position.

5. The apparatus of claim 1, wherein the end portion of the push rod is configured to engage the tablet and move the tablet through the S shape of the delivery passage.

6. The apparatus of claim 1, wherein at least a portion of the proboscis being housing is curved to facilitate positioning at least the distal end portion of the housing beneath a tongue of a patient for sublingual administration of the tablet, the curved portion of the housing defining the shape of the delivery passage.

7. The apparatus of claim 1, wherein the end portion of the push rod is a first end portion, the apparatus further comprising:
   a hub coupled to a second end portion of the push rod such that rotation of the hub moves the push rod from the first position to the second position.

8. The apparatus of claim 1, further comprising:
   a hub coupled to the housing, the hub configured to be rotated by a motor to move the push rod from the first position to the second position.

9. The method of claim 1, wherein the tablet includes a dosage of sufentanil.

10. An apparatus, comprising:
    a housing defining a nonlinear passage and an exit port;
    a seal disposed to cover the exit port;
    a shaft, at least a portion of the shaft being disposed in the nonlinear passage and being flexible such that a first end portion of the shaft can be moved within the nonlinear passage, the first end portion of the shaft configured to move a tablet through at least a portion of the nonlinear passage to the exit port, the first end portion of the shaft configured to push the tablet through the seal; and
    a rotary actuator coupled to a second end portion of the shaft, the rotary actuator configured to rotate the second end portion of the shaft to move the first end portion of the shaft from a first position to a second position.

11. The apparatus of claim 10, wherein the first end portion of the shaft is configured to be retracted into the nonlinear passage after pushing the tablet through the seal.

12. The apparatus of claim 10, wherein the housing being removably couplable to a tablet delivery device, the tablet delivery device configured to produce an indication of the status of the assembly of the housing and the tablet delivery device.

13. The apparatus of claim 10, wherein the nonlinear passage defined by the housing is S-shaped, the flexible portion of the shaft being moveable within the S-shaped portion of the nonlinear passage.

14. The apparatus of claim 10, further comprising:
    a hydrophilic material disposed to minimize saliva influx into the passage.

15. The apparatus of claim 10, wherein the rotary actuator is a hub disposed at least partially within the housing.

16. The apparatus of claim 10, wherein the rotary actuator is a hub disposed at least partially within the housing, the hub configured to be driven by a motor.

17. The apparatus of claim 10, wherein the housing is curved to facilitate positioning of at least a portion of the housing beneath a tongue of a patient.

18. The method of claim 10, wherein the tablet includes a dosage of sufentanil.

19. An apparatus for sublingual administration of a drug-containing tablet, comprising:
    a housing defining a delivery passage through which the tablet can be passed, the delivery passage having a nonlinear shape, a distal end portion of the housing defining an exit port;
    a seal disposed to cover the exit port;
    a flexible delivery member, at least a first end portion of the delivery member being movably disposed within the delivery passage such that the first end portion can be moved through the nonlinear shape of the delivery passage, the first end portion of the delivery member configured to move the tablet through at least a portion of the delivery passage to the exit port, the first end portion of the delivery member configured to push the tablet through the seal when the first end portion of the delivery member is moved within the delivery passage; and a hub coupled to a second end portion of the delivery member such that rotation of the hub moves the first end portion of the delivery member within the delivery passage.

20. The apparatus of claim 19, wherein the delivery passage has an S-shape and the delivery member is sufficiently flexible to assume the S-shape of the delivery passage.

21. The apparatus of claim 19, further comprising:
a shroud defining a cavity, the seal is disposed in the cavity defined by the shroud.

22. The apparatus of claim 19, wherein at least a portion of the housing is curved to facilitate positioning at least the distal end portion of the housing beneath a tongue of a patient for sublingual administration of the tablet.

23. The apparatus of claim 19, wherein the hub is configured to be rotated by a motor to move the delivery member between a first position and a second position.

24. The method of claim 19, wherein the hub is disposed at least partially within the housing, the hub configured to be driven by a motor.

25. The method of claim 19, wherein the tablet includes a dosage of sufentanil.

26. An apparatus for administration of a drug-containing tablet, comprising:
a housing defining a delivery passage through which the tablet can be passed, the delivery passage having a first curved portion and a second curved portion, the first curved portion being curved about a first axis, the second curved portion being curved about a second axis, a portion of the delivery passage being disposed between the first axis and the second axis, a distal end portion of the housing defining an exit port; and
a push rod, at least a portion of the push rod being disposed within the delivery passage, the push rod being movable within the delivery passage between a first position in which an end portion of the push rod is disposed within the delivery passage and a second position in which the end portion is extended from the exit port, the push rod configured to advance the tablet through the exit port upon movement from the first position to the second position, at least a portion of the push rod being sufficiently flexible to assume the shape of the first curved portion and the second curved portion when the push rod is moved from the first position to the second position.

27. The apparatus of claim 26, further comprising:
a seal disposed about the exit port, the end portion of the push rod being configured to extend through the seal when the push rod is in the second position.

28. The apparatus of claim 26, further comprising:
a hydrophilic material disposed to minimize saliva influx into the delivery passage.

29. The apparatus of claim 26, wherein the end portion of the push rod is configured to engage the tablet and move the tablet through the first curved portion of the delivery passage and the second curved portion of the delivery passage.

30. The apparatus of claim 26, wherein the housing is removably couplable to a tablet delivery device, the tablet delivery device configured to produce an indication of the status of the assembly of the housing and the tablet delivery device.

31. The apparatus of claim 26, wherein the end portion of the push rod is a first end portion, the apparatus further comprising:
a hub coupled to a second end portion of the push rod such that rotation of the hub moves the push rod from the first position to the second position.

32. The apparatus of claim 26, further comprising:
a hub coupled to the housing, the hub configured to be rotated by a motor to move the push rod from the first position to the second position.

33. The method of claim 26, wherein the tablet includes a dosage of sufentanil.

* * * * *

UNITED STATES PATENT AND TRADEMARK OFFICE
CERTIFICATE OF CORRECTION

Page 1 of 1

PATENT NO. : 8,357,114 B2
APPLICATION NO. : 11/650230
DATED : January 22, 2013
INVENTOR(S) : Andrew I. Poutiatine et al.

It is certified that error appears in the above-identified patent and that said Letters Patent is hereby corrected as shown below:

In the Claims

Column 47, line 60 (Claim 6), delete "proboscis being".

Column 48, line 8 (Claim 9), "method" should be --apparatus--.

Column 48, line 49 (Claim 18), "method" should be --apparatus--.

Column 49, line 18 (Claim 24), "method" should be --apparatus--.

Column 49, line 21 (Claim 25), "method" should be --apparatus--.

Column 50, line 34 (Claim 33), "method" should be --apparatus--.

Signed and Sealed this
Thirtieth Day of September, 2014

Michelle K. Lee
*Deputy Director of the United States Patent and Trademark Office*